(12) United States Patent
Jen et al.

(10) Patent No.: US 12,408,548 B2
(45) Date of Patent: Sep. 2, 2025

(54) PEROVSKITE LAYER, FABRICATION METHOD AND USE THE SAME

(71) Applicant: City University of Hong Kong, Kowloon (HK)

(72) Inventors: Alex Kwan Yue Jen, Kowloon (HK); Shengfan Wu, Kowloon (HK); Yichao Yan, Kowloon (HK)

(73) Assignee: City University of Hong Kong, Kowloon (HK)

( * ) Notice: Subject to any disclaimer, the term of this patent is extended or adjusted under 35 U.S.C. 154(b) by 43 days.

(21) Appl. No.: 18/499,651

(22) Filed: Nov. 1, 2023

(65) Prior Publication Data
US 2025/0143173 A1    May 1, 2025

(51) Int. Cl.
| | | |
|---|---|---|
| H10K 85/60 | (2023.01) | |
| C07C 211/63 | (2006.01) | |
| C07C 309/44 | (2006.01) | |
| H10K 30/40 | (2023.01) | |
| H10K 30/57 | (2023.01) | |
| H10K 85/20 | (2023.01) | |
| H10K 85/50 | (2023.01) | |

(52) U.S. Cl.
CPC .......... *H10K 85/615* (2023.02); *C07C 211/63* (2013.01); *C07C 309/44* (2013.01); *H10K 30/40* (2023.02); *H10K 30/57* (2023.02); *H10K 85/215* (2023.02); *H10K 85/50* (2023.02); *C07C 2603/24* (2017.05)

(58) Field of Classification Search
CPC ...... H10K 85/615; H10K 30/40; H10K 30/57; H10K 85/215; H10K 85/50; C07C 211/63; C07C 309/44; C07C 2603/24
See application file for complete search history.

(56) References Cited

U.S. PATENT DOCUMENTS

| | | | | |
|---|---|---|---|---|
| 2020/0402728 A1* | 12/2020 | Liao | ................. | H10K 71/15 |
| 2021/0319957 A1* | 10/2021 | Nishimura | ............ | C07C 211/54 |
| 2022/0025195 A1* | 1/2022 | Huang | ................. | C09D 11/037 |

OTHER PUBLICATIONS

Xin Wu "Improved stability and efficiency of perovskite/organic tandem solar cells with an all-inorganic perovskite layer" J. Mater. Chem. A, 2021, 9, 19778-19787 (Year: 2021).*

Alexander J. Bett "Semi-Transparent Perovskite Solar Cells with ITO Directly Sputtered on Spiro-OMeTAD for Tandem Applications" ACS Appl. Mater. Interfaces 2019, 11, 45796-45804 (Year: 2019).*

Fengzhu Li "Hydrogen-bond-bridged intermediate for perovskite solar cells with enhanced efficiency and stability" Nature Photonics | vol. 17 | Jun. 2023 | 478-484 (Year: 2023).*

Congping Li "Monoammonium Porphyrin for Blade-Coating Stable Large-Area Perovskite Solar Cells with >18% Efficiency" J. Am. Chem. Soc. 2019, 141, 6345-6351 (Year: 2019).*

Ziyan Jia "19.34 cm2 large-area quaternary organic photovoltaic module with 12.36% certified efficiency" vol. 9, No. 3 / Mar. 2021 / Photonics Research (Year: 2021).*

(Continued)

*Primary Examiner* — Michael Y Sun

(74) *Attorney, Agent, or Firm* — Renner, Kenner, Greive, Bobak, Taylor & Weber

(57) ABSTRACT

A perovskite layer for use in a solar cell includes a mixture of a halide perovskite and a sulfonyl naphthoquinone-based compound having a structure of Formula (I). Methods for fabricating the perovskite layer and a solar cell including a first active layer of the perovskite layer are also addressed.

39 Claims, 77 Drawing Sheets

(56) References Cited

OTHER PUBLICATIONS

Sies M. van der Kerk "Conformational Structure of 5,15-Bis[2-[(anthraquinone-2-sulfonyl)oxy]phenyl]-2,8,12,18-tetra-/i-butyl-3,7,13,17-tetramethylporphyrin. A NMR and Calculational Study" J. Phys. Chem. 1994, 98, 5408-5415 (Year: 1994).*
Zhimin Fang "Perovskite-based tandem solar cells" Science Bulletin 66 (2021) 621-636 (Year: 2021).*
J. Y. Kim et al., Efficient Tandem Polymer Solar Cells Fabricated by All-Solution Processing. Science 317, 222-225 (2007).
W. Shockley, H. J. Queisser, Detailed Balance Limit of Efficiency of p-n Junction Solar Cells. J. Appl. Phys. 32, 510-519 (1961).
D. P. McMeekin et al., A mixed-cation lead mixed-halide perovskite absorber for tandem solar cells. Science 351, 151-155 (2016).
P. Tockhorn et al., Nano-optical designs for high-efficiency monolithic perovskite-silicon tandem solar cells. Nat. Nanotechnol. 17, 1214-1221 (2022).
H. Chen et al., Regulating surface potential maximizes voltage in all-perovskite tandems. Nature 613, 676-681 (2023).
K. O. Brinkmann et al., Perovskite-organic tandem solar cells with indium oxide interconnect. Nature 604, 280-286 (2022).
A. Kojima, K. Teshima, Y. Shirai, T. Miyasaka, Organometal Halide Perovskites as Visible-Light Sensitizers for Photovoltaic Cells. J. Am. Chem. Soc. 131, 6050-6051 (2009).
E. T. Hoke et al., Reversible photo-induced trap formation in mixed-halide hybrid perovskites for photovoltaics. Chem. Sci. 6, 613-617 (2015).
A. J. Barker et al., Defect-Assisted Photoinduced Halide Segregation in Mixed-Halide Perovskite Thin Films. ACS Energy Lett. 2, 1416-1424 (2017).
D. J. Slotcavage, H. I. Karunadasa, M. D. McGehee, Light-Induced Phase Segregation in Halide-Perovskite Absorbers. ACS Energy Lett. 1, 1199-1205 (2016).
A. J. Knight, L. M. Herz, Preventing phase segregation in mixed-halide perovskites: a perspective. Energy Environ. Sci. 13, 2024-2046 (2020).
M. Abdi-Jalebi et al., Maximizing and stabilizing luminescence from halide perovskites with potassium passivation. Nature 555, 497-501 (2018).
J. Xu et al., Triple-halide wide-band gap perovskites with suppressed phase segregation for efficient tandems. Science 367, 1097-1104 (2020).
A. Al-Ashouri et al., Monolithic perovskite/silicon tandem solar cell with >29% efficiency by enhanced hole extraction. Science 370, 1300-1309 (2020).
Y. Zhao et al., Strain-activated light-induced halide segregation in mixed-halide perovskite solids. Nat. Commun. 11, 6328 (2020).
L. Tian, J. Xue, R. Wang, Halide Segregation in Mixed Halide Perovskites: Visualization and Mechanisms. Electronics 11, 700 (2022).
S. Draguta et al., Rationalizing the light-induced phase separation of mixed halide organic-inorganic perovskites. Nat. Commun. 8, 200 (2017).
C. G. Bischak et al., Tunable Polaron Distortions Control the Extent of Halide Demixing in Lead Halide Perovskites. J. Phys. Chem. 9, 3998-4005 (2018).
A. J. Knight et al., Electronic Traps and Phase Segregation in Lead Mixed-Halide Perovskite. ACS Energy Lett. 4, 75-84 (2019).
R. A. Kerner, Z. Xu, B. W. Larson, B. P. Rand, The role of halide oxidation in perovskite halide phase separation. Joule 5, 2273-2295 (2021).
G. F. Samu et al., Electrochemical Hole Injection Selectively Expels Iodide from Mixed Halide Perovskite Films. J. Am. Chem. Soc. 141, 10812-10820 (2019).
L. A. Frolova et al., Reversible Pb2+/Pb0 and I−/I3− Redox Chemistry Drives the Light-Induced Phase Segregation in All-Inorganic Mixed Halide Perovskites. Adv. Energy Mater. 11, 2002934 (2021).
Z. Xu et al., Halogen Redox Shuttle Explains Voltage-Induced Halide Redistribution in Mixed-Halide Perovskite Devices. ACS Energy Lett. 8, 513-520 (2023).
L. Wang et al., A Eu3+-Eu2+ ion redox shuttle imparts operational durability to Pb—I perovskite solar cells. Science 363, 265-270 (2019).
K. X. Steirer et al., Defect Tolerance in Methylammonium Lead Triiodide Perovskite. ACS Energy Lett. 1, 360-366 (2016).
M. Grätzel, Dye-sensitized solar cells. J. Photochem. Photobiol. 4, 145-153 (2003).
Q. Jiang et al., Surface passivation of perovskite film for efficient solar cells. Nat. Photon. 13, 460-466 (2019).
B. Chen, P. N. Rudd, S. Yang, Y. Yuan, J. Huang, Imperfections and their passivation in halide perovskite solar cells. Chem. Soc. Rev. 48, 3842-3867 (2019).
B. Huskinson et al., A metal-free organic-inorganic aqueous flow battery. Nature 505, 195-198 (2014).
E. Mourad et al., Biredox ionic liquids with solid-like redox density in the liquid state for high-energy supercapacitors. Nat. Mater. 16, 446-453 (2017).
C.-Y. Cai et al., Photoelectrochemical asymmetric catalysis enables site- and enantioselective cyanation of benzylic C—H bonds. Nat. Catal. 5, 943-951 (2022).
K. Lin et al., Alkaline quinone flow battery. Science 349, 1529-1532 (2015).
P. Vanysek, Electrochemical series. CRC Handb. Chem. Phys. 8, 8-33 (2000).
Y.-H. Lin et al., A piperidinium salt stabilizes efficient metal-halide perovskite solar cells. Science 369, 96-102 (2020).
Y. Jo et al., High Performance of Planar Perovskite Solar Cells Produced from PbI2(DMSO) and PbI2(NMP) Complexes by Intramolecular Exchange. Adv. Mater. Interfaces 3, 1500768 (2016).
K. Xiao et al., Scalable processing for realizing 21.7%-efficient all-perovskite tandem solar modules. Science 376, 762-767 (2022).
K. Xiao et al., All-perovskite tandem solar cells with 24.2% certified efficiency and area over 1 cm2 using surface-anchoring zwitterionic antioxidant. Nat. Energy 5, 870-880 (2020).
R. E. Beal et al., Structural origins of light-induced phase segregation in organic-inorganic halide perovskite photovoltaic materials. Matter 2, 207-219 (2020).
S. Tan et al., Surface reconstruction of halide perovskites during post-treatment. J. Am. Chem. Soc. 143, 6781-6786 (2021).
L. Zhao et al., Redox Chemistry Dominates the Degradation and Decomposition of Metal Halide Perovskite Optoelectronic Devices. ACS Energy Lett. 1, 595-602 (2016).
Y. Guo et al., Phenylalkylammonium passivation enables perovskite light emitting diodes with record high-radiance operational lifetime: the chain length matters. Nat. Commun. 12, 644 (2021).
M. I. Saidaminov et al., Multi-cation perovskites prevent carrier reflection from grain surfaces. Nat. Mater. 19, 412-418 (2020).
Q. Jiang et al., Compositional texture engineering for highly stable wide-bandgap perovskite solar cells. Science 378, 1295-1300 (2022).
X. Deng et al., Co-assembled Monolayers as Hole-Selective Contact for High-Performance Inverted Perovskite Solar Cells with Optimized Recombination Loss and Long-Term Stability. Angew. Chem. Int. Ed. 61, e202203088 (2022).
F. Li et al., Regulating surface termination for efficient inverted perovskite solar cells with greater than 23% efficiency. J. Am. Chem. Soc. 142, 20134-20142 (2020).
O. Almora et al., Quantifying the Absorption Onset in the Quantum Efficiency of Emerging Photovoltaic Devices. Adv. Energy Mater. 11, 2100022 (2021).
S. Wu, M. Liu, A. K.-Y. Jen, Prospects and challenges for perovskite-organic tandem solar cells. Joule 7, 484-502 (2023).
X. Wu, B. Li, Z. Zhu, C.-C. Chueh, A. K. Y. Jen, Designs from single junctions, heterojunctions to multijunctions for high-performance perovskite solar cells. Chem. Soc. Rev. 50, 13090-13128 (2021).
B. Abdollahi Nejand et al., Scalable two-terminal all-perovskite tandem solar modules with a 19.1% efficiency. Nat. Energy 7, 620-630 (2022).
Q. Jiang et al., Surface reaction for efficient and stable inverted perovskite solar cells. Nature 611, 278-283 (2022).

(56) References Cited

OTHER PUBLICATIONS

Lee, M. M.; Teuscher, J.; Miyasaka, T.; Murakami, T. N.; Snaith, H. J. Efficient Hybrid Solar Cells Based on Meso-Superstructured Organometal Halide Perovskites. Science 2012, 338 (6107), 643-647. https://doi.org/10.1126/science.1228604.

Stranks, S. D.; Eperon, G. E.; Grancini, G.; Menelaou, C.; Alcocer, M. J. P.; Leijtens, T.; Herz, L. M.; Petrozza, A.; Snaith, H. J. Electron-Hole Diffusion Lengths Exceeding 1 Micrometer in an Organometal Trihalide Perovskite Absorber. Science 2013, 342 (6156), 341-344. https://doi.org/10.1126/science.1243982.

Park, N.-G. Perovskite Solar Cells: An Emerging Photovoltaic Technology. Materials Today 2015, 18 (2), 65-72. https://doi.org/10.1016/j.mattod.2014.07.007.

De Wolf, S.; Holovsky, J.; Moon, S.-J.; Löper, P.; Niesen, B.; Ledinsky, M.; Haug, F.-J.; Yum, J.-H.; Ballif, C. Organometallic Halide Perovskites: Sharp Optical Absorption Edge and Its Relation to Photovoltaic Performance. J. Phys. Chem. Lett. 2014, 5 (6), 1035-1039. https://doi.org/10.1021/jz500279b.

Kagan, C. R.; Mitzi, D. B.; Dimitrakopoulos, C. D. Organic-Inorganic Hybrid Materials as Semiconducting Channels in Thin-Film Field-Effect Transistors. Science 1999, 286 (5441), 945-947. https://doi.org/10.1126/science.286.5441.945.

Wilson, G. M.; Al-Jassim, M.; Metzger, W. K.; Glunz, S. W.; Verlinden, P.; Xiong, G.; Mansfield, L. M.; Stanbery, B. J.; Zhu, K.; Yan, Y.; Berry, J. J.; Ptak, A. J.; Dimroth, F.; Kayes, B. M.; Tamboli, A. C.; Peibst, R.; Catchpole, K.; Reese, M. O.; Klinga, C. S.; Denholm, P.; Morjaria, M.; Deceglie, M. G.; Freeman, J. M.; Mikofski, M. A.; Jordan, D. C.; TamizhMani, G.; Sulas-Kern, D. B. The 2020 Photovoltaic Technologies Roadmap. J. Phys. D: Appl. Phys. 2020, 53 (49), 493001. https://doi.org/10.1088/1361-6463/ab9c6a.

Eperon, G. E.; Hörantner, M. T.; Snaith, H. J. Metal Halide Perovskite Tandem and Multiple-Junction Photovoltaics. Nat Rev Chem 2017, 1 (12), 1-18. https://doi.org/10.1038/s41570-017-0095.

Bush, K. A.; Manzoor, S.; Frohna, K.; Yu, Z. J.; Raiford, J. A.; Palmstrom, A. F.; Wang, H.-P.; Prasanna, R.; Bent, S. F.; Holman, Z. C.; McGehee, M. D. Minimizing Current and Voltage Losses to Reach 25% Efficient Monolithic Two-Terminal Perovskite-Silicon Tandem Solar Cells. ACS Energy Lett. 2018, 3 (9), 2173-2180. https://doi.org/10.1021/acsenergylett.8b01201.

Gharibzadeh, S.; Hossain, I. M.; Fassl, P.; Nejand, B. A.; Abzieher, T.; Schultes, M.; Ahlswede, E.; Jackson, P.; Powalla, M.; Schäfer, S.; Rienäcker, M.; Wietler, T.; Peibst, R.; Lemmer, U.; Richards, B. S.; Paetzold, U. W. 2D/3D Heterostructure for Semitransparent Perovskite Solar Cells with Engineered Bandgap Enables Efficiencies Exceeding 25% in Four-Terminal Tandems with Silicon and CIGS. Advanced Functional Materials 2020, 30 (19), 1909919. https://doi.org/10.1002/adfm.201909919.

Jaysankar, M.; Raul, B. A. L.; Bastos, J.; Burgess, C.; Weijtens, C.; Creatore, M.; Aernouts, T.; Kuang, Y.; Gehlhaar, R.; Hadipour, A.; Poortmans, J. Minimizing Voltage Loss in Wide-Bandgap Perovskites for Tandem Solar Cells. ACS Energy Lett. 2019, 4 (1), 259-264. https://doi.org/10.1021/acsenergylett.8b02179.

Hou, Y.; Aydin, E.; De Bastiani, M.; Xiao, C.; Isikgor, F. H.; Xue, D.-J.; Chen, B.; Chen, H.; Bahrami, B.; Chowdhury, A. H.; Johnston, A.; Baek, S.-W.; Huang, Z.; Wei, M.; Dong, Y.; Troughton, J.; Jalmood, R.; Mirabelli, A. J.; Allen, T. G.; Van Kerschaver, E.; Saidaminov, M. I.; Baran, D.; Qiao, Q.; Zhu, K.; De Wolf, S.; Sargent, E. H. Efficient Tandem Solar Cells with Solution-Processed Perovskite on Textured Crystalline Silicon. Science 2020, 367 (6482), 1135-1140. https://doi.org/10.1126/science.aaz3691.

Han, Q.; Hsieh, Y.-T.; Meng, L.; Wu, J.-L.; Sun, P.; Yao, E.-P.; Chang, S.-Y.; Bae, S.-H.; Kato, T.; Bermudez, V.; Yang, Y. High-Performance Perovskite/Cu(In,Ga)Se2 Monolithic Tandem Solar Cells. Science 2018, 361 (6405), 904-908. https://doi.org/10.1126/science.aat5055.

Kim, D.; Jung, H. J.; Park, I. J.; Larson, B. W.; Dunfield, S. P.; Xiao, C.; Kim, J.; Tong, J.; Boonmongkolras, P.; Ji, S. G.; Zhang, F.; Pae, S. R.; Kim, M.; Kang, S. B.; Dravid, V.; Berry, J. J.; Kim, J. Y.; Zhu, K.; Kim, D. H.; Shin, B. Efficient, Stable Silicon Tandem Cells Enabled by Anion-Engineered Wide-Bandgap Perovskites. Science 2020, 368 (6487), 155-160. https://doi.org/10.1126/science.aba3433.

Lin, R.; Xiao, K.; Qin, Z.; Han, Q.; Zhang, C.; Wei, M.; Saidaminov, M. I.; Gao, Y.; Xu, J.; Xiao, M.; Li, A.; Zhu, J.; Sargent, E. H.; Tan, H. Monolithic All-Perovskite Tandem Solar Cells with 24.8% Efficiency Exploiting Comproportionation to Suppress Sn(II) Oxidation in Precursor Ink. Nat Energy 2019, 4 (10), 864-873. https://doi.org/10.1038/s41560-019-0466-3.

Tong, J.; Song, Z.; Kim, D. H.; Chen, X.; Chen, C.; Palmstrom, A. F.; Ndione, P. F.; Reese, M. O.; Dunfield, S. P.; Reid, O. G.; Liu, J.; Zhang, F.; Harvey, S. P.; Li, Z.; Christensen, S. T.; Teeter, G.; Zhao, D.; Al-Jassim, M. M.; van Hest, M. F. A. M.; Beard, M. C.; Shaheen, S. E.; Berry, J. J.; Yan, Y.; Zhu, K. Carrier Lifetimes of >1 Ms in Sn—Pb Perovskites Enable Efficient All-Perovskite Tandem Solar Cells. Science 2019, 364 (6439), 475-479. https://doi.org/10.1126/science.aav7911.

Zhao, D.; Yu, Y.; Wang, C.; Liao, W.; Shrestha, N.; Grice, C. R.; Cimaroli, A. J.; Guan, L.; Ellingson, R. J.; Zhu, K.; Zhao, X.; Xiong, R.-G.; Yan, Y. Low-Bandgap Mixed Tin-Lead Iodide Perovskite Absorbers with Long Carrier Lifetimes for All-Perovskite Tandem Solar Cells. Nat Energy 2017, 2 (4), 1-7. https://doi.org/10.1038/nenergy.2017.18.

Raga, S. R.; Jung, M.-C.; Lee, M. V.; Leyden, M. R.; Kato, Y.; Qi, Y. Influence of Air Annealing on High Efficiency Planar Structure Perovskite Solar Cells. Chem. Mater. 2015, 27 (5), 1597-1603. https://doi.org/10.1021/cm5041997.

Li, Y.; Xu, X.; Wang, C.; Ecker, B.; Yang, J.; Huang, J.; Gao, Y. Light-Induced Degradation of CH3NH3PbI3 Hybrid Perovskite Thin Film. J. Phys. Chem. C 2017, 121 (7), 3904-3910. https://doi.org/10.1021/acs.jpcc.6b11853.

Bischak, C. G.; Hetherington, C. L.; Wu, H.; Aloni, S.; Ogletree, D. F.; Limmer, D. T.; Ginsberg, N. S. Origin of Reversible Photoinduced Phase Separation in Hybrid Perovskites. Nano Lett. 2017, 17 (2), 1028-1033. https://doi.org/10.1021/acs.nanolett.6b04453.

Brennan, M. C.; Ruth, A.; Kamat, P. V.; Kuno, M. Photoinduced Anion Segregation in Mixed Halide Perovskites. Trends in Chemistry 2020, 2 (4), 282-301. https://doi.org/10.1016/j.trechm.2020.01.010.

Zhou, Y.; Jia, Y.-H.; Fang, H.-H.; Loi, M. A.; Xie, F.-Y.; Gong, L.; Qin, M.-C.; Lu, X.-H.; Wong, C.-P.; Zhao, N. Composition-Tuned Wide Bandgap Perovskites: From Grain Engineering to Stability and Performance Improvement. Advanced Functional Materials 2018, 28 (35), 1803130. https://doi.org/10.1002/adfm.201803130.

Kim, J.; Saidaminov, M. I.; Tan, H.; Zhao, Y.; Kim, Y.; Choi, J.; Jo, J. W.; Fan, J.; Quintero-Bermudez, R.; Yang, Z.; Quan, L. N.; Wei, M.; Voznyy, O.; Sargent, E. H. Amide-Catalyzed Phase-Selective Crystallization Reduces Defect Density in Wide-Bandgap Perovskites. Advanced Materials 2018, 30 (13), 1706275. https://doi.org/10.1002/adma.201706275.

\* cited by examiner

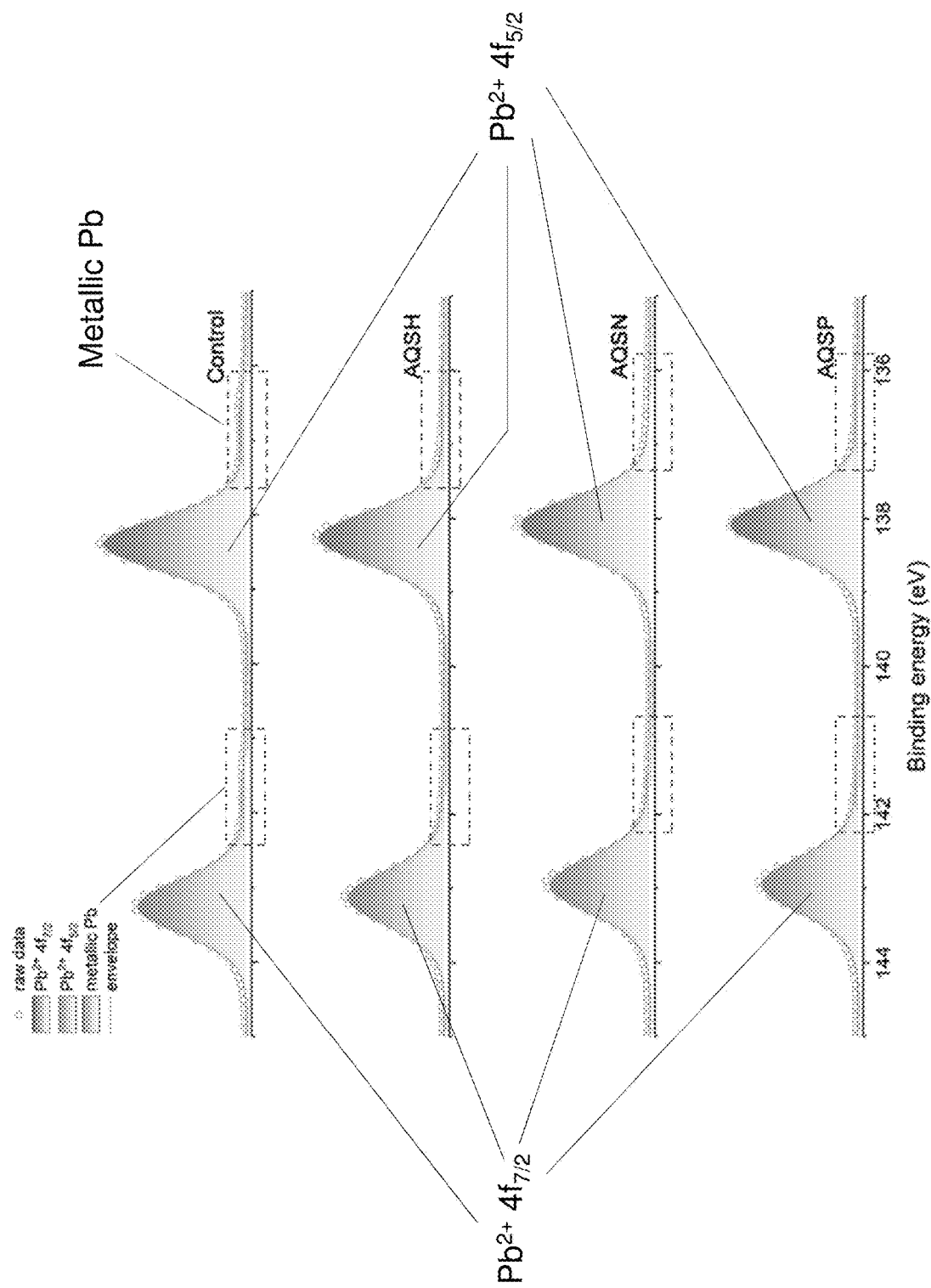

| | $\tau_1$ (ns) | $A_1$ (%) | $\tau_2$ (ns) | $A_2$ (%) | $\tau_{avg}$ (ns) |
|---|---|---|---|---|---|
| Control | 148.64 | 8.56 | 923.23 | 148.64 | 911.73 |
| AQSH | 111.49 | 5.04 | 1074.80 | 94.96 | 1069.53 |
| AQSN | 149.18 | 2.58 | 1407.69 | 97.42 | 1404.17 |
| AQSP | 140.93 | 2.36 | 1507.95 | 97.64 | 1504.87 |

Note: the average carrier lifetime is calculated with the equation of: $\tau_{avg} = (A_1\tau_1^2 + A_2\tau_2^2)/(A_1\tau_1 + A_2\tau_2)$, where the parameters $A_1$ and $A_2$ are the amplitude fraction for each decay component, and $\tau_1$ and $\tau_2$ represent the time constant of the two types of decay.

Fig. 35B

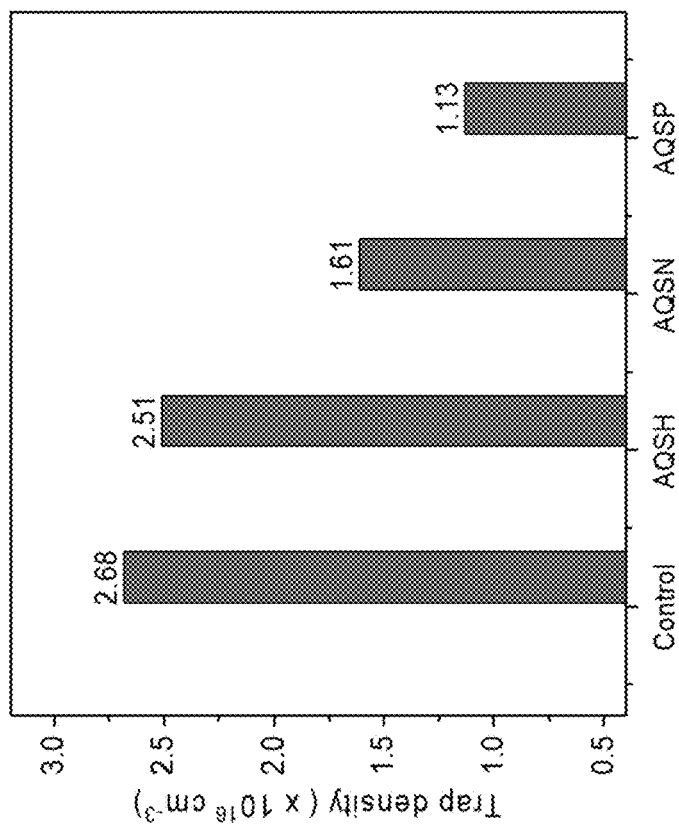
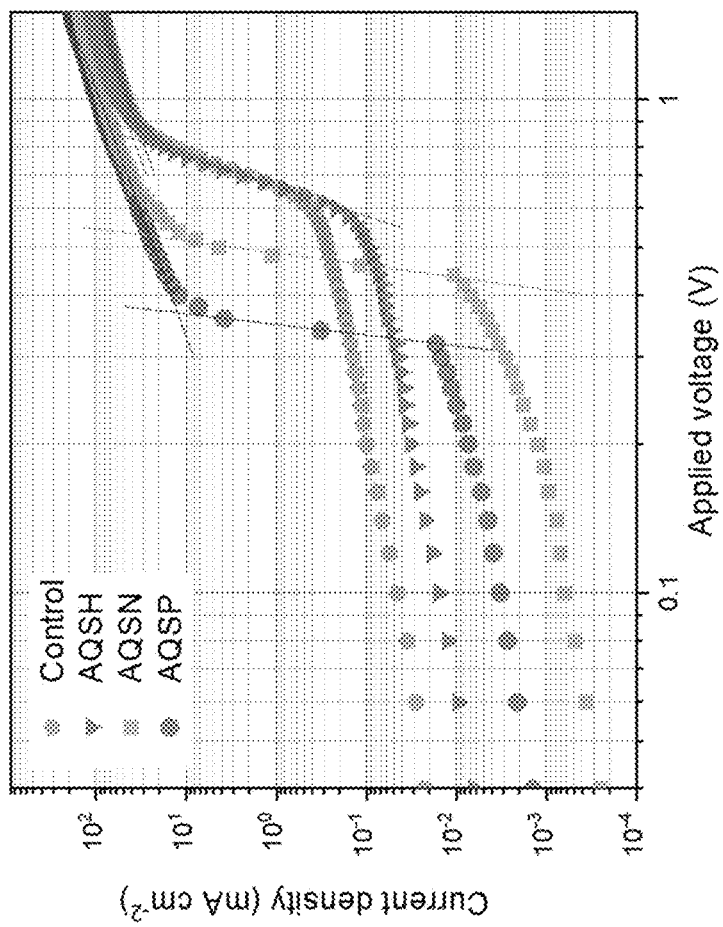
Fig. 36A
Fig. 36B

| Device | $V_{oc}$ (V) | $J_{sc}$ (mA cm$^{-2}$) | FF (%) | PCE (%) |
|---|---|---|---|---|
| Control | 1.309 | 17.49 | 81.58 | 18.68 |
| AQSH | 1.311 | 17.39 | 82.04 | 18.70 |
| AQSN | 1.329 | 17.34 | 82.65 | 19.05 |
| AQSP (Target) | 1.351 | 17.52 | 82.74 | 19.58 |

Fig. 39B

| Reference | $E_g$ (eV) | $V_{oc}$ (V) |
|---|---|---|
| Energy Environ. Sci., 2016, 9, 1706-1724 | 1.85 | 1.11 |
| | 1.85 | 1.09 |
| | 1.85 | 1.13 |
| ACS Appl. Mater. Interfaces 2016, 8, 2232-2237. | 1.77 | 1.08 |
| Nano Lett. 2016, 16, 7739-7747. | 1.80 | 1.05 |
| Science. 2016, 354, 861-865. | 1.80 | 1.12 |
| Adv. Mater. 2017, 29, 1702140. | 1.82 | 1.22 |
| Nano Lett. 2017, 17, 6863-6869. | 1.79 | 1.04 |
| Adv. Energy Mater. 2018, 8, 1701543. | 1.78 | 1.12 |
| | 1.81 | 1.17 |
| ACS Energy Lett. 2018, 3, 214-219. | 1.87 | 1.21 |
| Nature 2018, 555, 497-501. | 1.78 | 1.23 |
| Nano Lett. 2018, 18, 6, 3985 | 1.82 | 1.30 |
| | 1.83 | 1.33 |
| | 1.84 | 1.35 |
| J. Phys. Chem. Lett. 2018, 9, 12, 3779 | 1.82 | 1.29 |
| Adv. Mater. 2017, 29, 34, 172140 | 1.82 | 1.2 |
| Sol. RRL 2020, 4, 7, 2000098 | 1.8 | 1.25 |
| ACS Energy. Lett. 2020, 5, 8, 2728 | 1.8 | 1.17 |
| Science 2016, 354, 861-865 | 1.8 | 1.12 |
| Adv. Energy Mater. 2019, 10, 1903085 | 1.82 | 1.2 |
| Nat. Energy 2019, 4, 864-873 | 1.77 | 1.216 |
| Nat. Commun. 2019, 10, 4498 | 1.8 | 1.22 |
| Joule 2020, 4, 1594-1606 | 1.77 | 1.113 |
| Nat. Energy 2020, 5, 870-880 | 1.77 | 1.206 |
| Nat. Energy 2020, 5, 657-665 | 1.78 | 1.23 |
| Adv. Mater. 2022, 34, 2110356 | 1.80 | 1.263 |
| Nature 2022, 604, 280-286 | 1.85 | 1.34 |
| Nat. Energy 2022, 7, 229-237 | 1.79 | 1.26 |
| Adv. Mater. 2022, 34, 2108829 | 1.79 | 1.25 |
| Nature 2023, 613, 676-681 | 1.79 | 1.33 |
| Science 2022, 378, 1295-1300 | 1.75 | 1.33 |
| Nature 2023, https://doi.org/10.1038/s41586-023-05992-y | 1.77 | 1.31 |
| This work | 1.81 | 1.351 |

Fig. 42B

| Scan direction | PCE (%) | $V_{oc}$ (V) | $J_{sc}$ (mA cm$^{-2}$) | FF [%] |
| --- | --- | --- | --- | --- |
| Reverse | 25.22 | 2.151 | 14.36 | 81.65 |
| Forward | 25.04 | 2.150 | 14.25 | 81.74 |

Fig. 46B

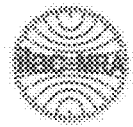

Test and Calibration Center of New Energy Device and Module,
Shanghai Institute of Microsystem and Information Technology,
Chinese Academy of Sciences (SIMIT)

Measurement Report

Report No. 22TR121101

| | |
|---|---|
| Client Name | Prof. Alex K.-Y. Jen's Research Group |
| Client Address | City University of Hong Kong, Kowloon Tong, Hong Kong SAR |
| Sample | Perovskite/organic tandem solar cell |
| Manufacturer | City University of Hong Kong |
| Measurement Date | 11th December, 2022 |

Performed by: Qiang Shi   Date: 11/12/2022

Reviewed by: Wenjie Zhao   Date: 11/14/2022

Approved by: Zhengxin Liu   Date: 18/12/2022

Address: No.235 Chengbei Road, Jiading, Shanghai   Post Code: 201800
E-mail: solarcell@mail.sim.ac.cn   Tel: +86-021-69976921

The measurement report without signature and seal are not valid.
This report shall not be reproduced, except in full, without the approval of SIMIT.

Fig. 52A

Report No. 22TR121101

Sample Information

| Sample Type | Perovskite/organic tandem solar cell |
|---|---|
| Serial No. | S-A# |
| Lab Internal No. | 22121101-1# |
| Measurement Item | I-V characteristic |
| Measurement Environment | 24.4±2.0°C, 35.6±5.0%R.H |

Measurement of I-V characteristic

| Reference cell | AK-200(Serial No.:2000041) |
|---|---|
| Reference cell Type | mono-Si, WPVS, calibrated by National Institute of Metrology, China (Certificate No. GXgf2022-01035) |
| Calibration Value/Date of Calibration for Reference cell | 128.1mA/ Apr. 2022 |
| Measurement Conditions | Standard Test Condition (STC): Spectral Distribution: AM1.5 according to IEC 60904-3 Ed.3, Irradiance: 1000±50W/m², Temperature: 25±2°C |
| Measurement Equipment/ Date of Calibration | AAA Steady State Solar Simulator (YSS-T155-2M) / July.2022<br>IV test system (ADCMT 6246) / June. 2022<br>Measuring Microscope (MF-B2017C) /July.2022<br>SR Measurement system (CEP-25ML-CAS) / April.2022 |
| Measurement Method | I-V Measurement:<br>Logarithmic sweep in both directions (Voc to Isc and Isc to Voc) during one flash based on IEC 60904-1:2006;<br>Spectral Mismatch factor was calculated according to IEC 60904-7 and I-V correction was performed according to IEC 60891. |
| Measurement Uncertainty | Area: 1.1%(k=2); Isc: 1.9%(k=2); Voc: 1.0%(k=2); Pmax: 2.7%(k=2); Eff: 2.9%(k=2) |

====Measurement Results====

| Wavelength (nm) | TOP | Bottom | Wavelength (nm) | TOP | Bottom | Wavelength (nm) | TOP | Bottom |
|---|---|---|---|---|---|---|---|---|
| 300 | 0.094 | 0.007 | 540 | 0.926 | 0.126 | 780 | 0.013 | 0.983 |
| 310 | 0.199 | 0.002 | 550 | 0.913 | 0.151 | 790 | 0.019 | 0.983 |
| 320 | 0.370 | 0.000 | 560 | 0.886 | 0.178 | 800 | 0.009 | 0.983 |
| 330 | 0.556 | 0.000 | 570 | 0.861 | 0.183 | 810 | 0.013 | 0.987 |
| 340 | 0.730 | 0.006 | 580 | 0.830 | 0.219 | 820 | 0.010 | 0.992 |
| 350 | 0.848 | 0.006 | 590 | 0.801 | 0.237 | 830 | 0.011 | 0.997 |
| 360 | 0.935 | 0.009 | 600 | 0.777 | 0.261 | 840 | 0.022 | 1.000 |
| 370 | 0.962 | 0.005 | 610 | 0.767 | 0.275 | 850 | 0.023 | 0.977 |
| 380 | 0.983 | 0.010 | 620 | 0.754 | 0.298 | 860 | 0.012 | 0.921 |
| 390 | 0.987 | 0.014 | 630 | 0.739 | 0.314 | 870 | 0.020 | 0.803 |
| 400 | 0.986 | 0.007 | 640 | 0.727 | 0.332 | 880 | 0.013 | 0.643 |
| 410 | 1.000 | 0.017 | 650 | 0.713 | 0.334 | 890 | 0.011 | 0.453 |
| 420 | 0.988 | 0.009 | 660 | 0.676 | 0.371 | 900 | 0.013 | 0.291 |
| 430 | 0.980 | 0.014 | 670 | 0.561 | 0.436 | 910 | 0.009 | 0.175 |
| 440 | 0.993 | 0.013 | 680 | 0.400 | 0.561 | 920 | 0.011 | 0.094 |
| 450 | 0.984 | 0.012 | 690 | 0.225 | 0.706 | 930 | 0.008 | 0.055 |
| 460 | 0.996 | 0.020 | 700 | 0.090 | 0.804 | 940 | 0.001 | 0.029 |
| 470 | 0.989 | 0.015 | 710 | 0.031 | 0.864 | 950 | 0.007 | 0.020 |
| 480 | 0.990 | 0.019 | 720 | 0.030 | 0.911 | 960 | 0.009 | 0.018 |
| 490 | 0.989 | 0.033 | 730 | 0.022 | 0.937 | 970 | 0.008 | 0.012 |
| 500 | 0.987 | 0.043 | 740 | 0.030 | 0.945 | 980 | 0.003 | 0.009 |
| 510 | 0.979 | 0.061 | 750 | 0.022 | 0.965 | 990 | 0.000 | 0.012 |
| 520 | 0.967 | 0.071 | 760 | 0.017 | 0.978 | 1000 | 0.012 | 0.005 |
| 530 | 0.950 | 0.094 | 770 | 0.018 | 0.984 | - | - | - |

| Reference | PCE (%) | $V_{oc}$ (V) | $J_{sc}$ (mA cm$^{-2}$) | FF [%] |
|---|---|---|---|---|
| Science Bulletin 64, 885-887 (2019) | 15.04 | 1.71 | 11.98 | 73.4 |
| J. Phys. Chem. Lett. 11, 9596-9604 (2020) | 17.24 | 1.82 | 13.2 | 71.68 |
| Adv. Energy Mater. 10, 2000361 (2020) | 15.13 | 1.85 | 11.52 | 70.98 |
| Joule 4, 1594-1606 (2020) | 20.6 | 1.902 | 13.05 | 83.1 |
| Nano Lett. 21, 7845-7854 (2021) | 21.1 | 1.96 | 13.3 | 80.8 |
| Adv. Mater. 34, 2108829 (2022) | 22.0 | 1.88 | 15.7 | 74.6 |
| Nat. Energy 7, 229-237 (2022) | 23.60 (certified 22.95) | 2.06 | 14.83 | 77.2 |
| Nature 604, 280-286 (2022) | 24.0 (certified 23.10) | 2.15 | 14.0 | 80 |
| Adv. Mater. 35, 2208604 (2023) | 23.17 | 2.15 | 13.43 | 80.25 |
| This work | 25.22 (certified 24.27%) | 2.151 | 14.36 | 81.65 |

Fig. 53

PEROVSKITE LAYER, FABRICATION METHOD AND USE THE SAME

TECHNICAL FIELD

The present invention relates to a perovskite layer for example particularly, but not exclusively, a perovskite layer comprising a mixture of a halide perovskite and a sulfonyl naphthoquinone-based compound; and a method for fabricating the perovskite layer. Also pertaining to the present invention is a solar cell comprising a first active layer of the perovskite layer.

BACKGROUND OF THE INVENTION

Metal halide perovskite solar cells (PSCs) are promising photovoltaic (PV) technologies owing to their high absorption coefficient, low exciton binding energy, high carrier mobility, long carrier diffusion length and ambipolar charge transport. PSCs may generally be configured as single-junction solar cells and multi-junction (or tandem) solar cells (i.e., solar cells consisting of two or more sub-cells). In particular, since tandem configurations would allow combination of sub-cells with different properties (such as the combination of a wide-bandgap and a low-bandgap subcells that could cater both high-energy and low-energy photons upon operation), it is believed that PSCs with tandem configurations would have a higher power conversion efficiency (PCE) as compared with those having single-junction configurations. For example, in perovskite-organic tandem solar cells (PO-TSCs) with a front sub-cell having a desired bandgap ($E_g$) of about 1.8 to 1.9 eV, its PCE may be increased from about 15% to about 24%, particularly when employing I/Br mixed perovskites (FIG. 1A).

However, the perovskite layer of PSCs usually suffers from severe halide phase segregation during device operation, which is believed to be a result of halide migration through halide vacancies within the perovskite film, posing a significant obstacle to the long-term stability of perovskite-based PSCs. In addition, under continuous illumination and/or heating, $Pb^{2+}$ ions in perovskites are also prone to be reduced to metallic $Pb^0$, which is detrimental to device efficiency and stability.

Whilst there are reports on suppressing halide segregation by, for example, crystallization control, defect passivation, surface modulation, and strain engineering, it is believed that none of these strategies could address the facile reduction of $Pb^{2+}$ to $Pb^0$ at the same time. In addition, the additives used in the reported strategies are either inorganic compounds, which are believed to be hard to tune their properties synthetically; or sacrificial agents that are believed to diminish soon after taking effects. That said, it remains a challenge to have an additive that is facile to tailor its properties for elimination different defects and can function in a sustainable manner without introducing additional deep-level defects.

The invention seeks to eliminate or at least to mitigate such shortcomings by providing a new or otherwise improved solar cell active layer, particularly an active perovskite layer that is capable of enabling selective iodine ($I_2$) reduction and metallic lead ($Pb^0$) oxidation in a sustainable manner.

SUMMARY OF THE INVENTION

In a first aspect of the present invention, there is provided a perovskite layer for use in a solar cell comprising a mixture of a halide perovskite and a sulfonyl naphthoquinone-based compound having a structure of Formula (I):

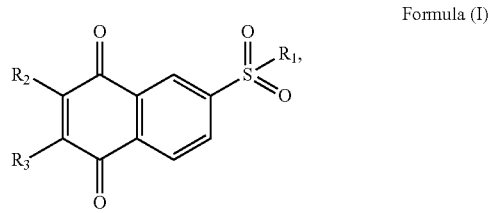

Formula (I)

wherein:

$R_1$ is independently selected from one of OM, $OR_4$, and $NR_5R_6$, with M being a cation, $R_4$, $R_5$ and $R_6$ being independently selected from a hydrogen and a substituent; and $R_2$ and $R_3$ are independently selected from a hydrogen and a substituent, or $R_2$ and $R_3$ may form a fused ring.

Optionally, M is selected from the group consisting of $H^+$, $Na^+$, $K^+$, $Cs^+$, $Rb^+$, $Sr^{2+}$, $Ca^{2+}$, $Ni^{2+}$, $Cu^{2+}$, $Co^{2+}$, $Zn^{2+}$, $Mg^{2+}$, $Ba^{2+}$, $Li^+$, ammonium ion, and aminum ion; $R_2$, $R_3$, $R_4$, $R_5$ and $R_6$ are independently selected from the group consisting of hydrogen, substituted or unsubstituted C1 to C4 alkyl, substituted or unsubstituted C2 to C6 alkenyl, substituted or unsubstituted C2 to C6 alkynyl, halogen, substituted or unsubstituted C6 to C10 aryl, —CN, —C(=O)OH, —C(=O)H, —C(=O)$R_7$, —O$R_7$, —SH, —S$R_7$, —NH$_2$, —NH$R_6$, —N($R_7$)$_2$, —Si($R_7$)$_3$, —OSi($R_7$)$_3$, —S(O)OH and —P(O)(OH)$_2$ where $R_7$ is an alkyl or a phenyl; and when $R_2$ and $R_3$ form a fused ring, it comprises a substituted or unsubstituted 6-membered to 14-membered ring.

In an optional embodiment, the sulfonyl naphthoquinone-based compound is any one of Formula (II), (III), (IV), (V), (VI), or (VII):

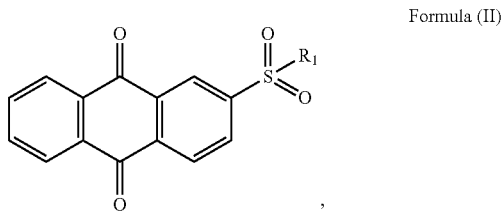

Formula (II)

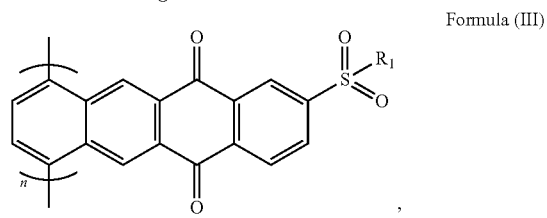

Formula (III)

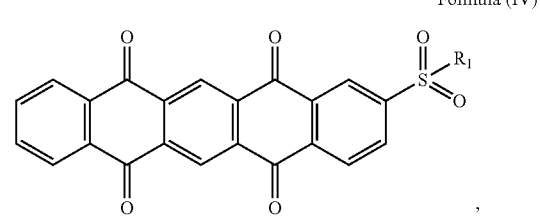

Formula (IV)

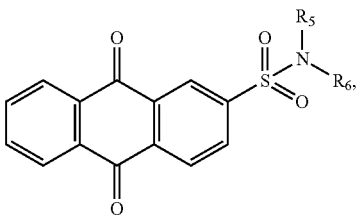

Formula (V)

,

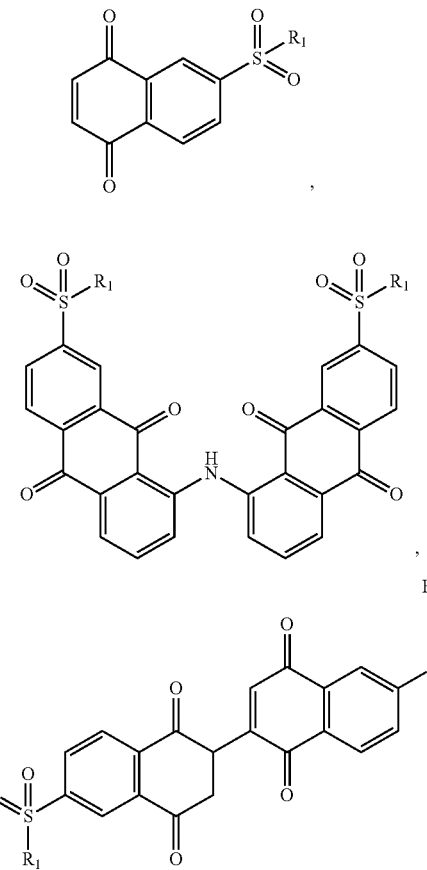

Formula (VI)

, or

Formula (VII)

with $R_1$ as defined above; and n being 1-1000.

It is optional that the sulfonyl naphthoquinone-based compound of Formula (II) is selected form any one of Formula (VIII), Formula (IX), or Formula (X):

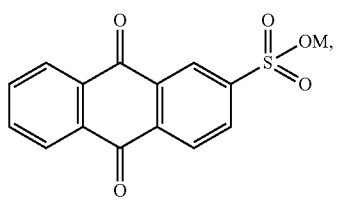

Formula (VIII)

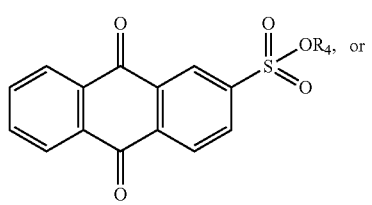

Formula (IX)

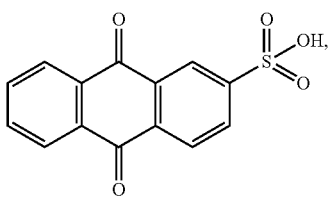

Formula (X)

with M being $H^+$, ammonium ion or aminum ion; $R_4$ being C1 to C4 alkyl; $R_5$ and $R_6$ being independently selected from hydrogen and C1 to C4 alkyl.

In an embodiment of the invention, the sulfonyl naphthoquinone-based compound of Formula (VIII) is selected from any one of the Formula (VIIIa), (VIIIb), and (VIIIc):

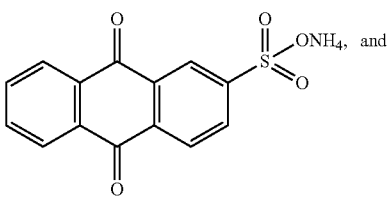

Formula (VIIIa)

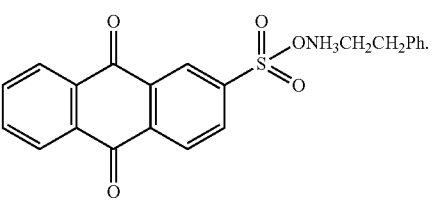

Formula (VIIIb)

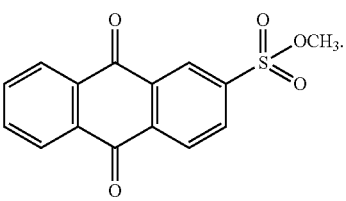

Formula (VIIIc)

In an optional embodiment, the sulfonyl naphthoquinone-based compound comprises a structure of Formula (IXa):

Formula (IXa)

In an optional embodiment, the sulfonyl naphthoquinone-based compound comprises a structure of Formula (Xa):

Formula (Xa)

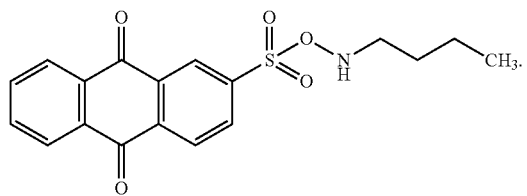

Optionally, the halide perovskite comprises a crystal grain structure of $[A^{+1}B^{+2}X^{-1}{}_3]$, with $A^{+1}$ being an A-site monovalent cation, $B^{+2}$ being a B-site divalent cation, and $X^{-1}$ being a halide anion.

It is optional that the A-site monovalent cation is selected from the group consisting of formamidinium ($FA^+$), methylammonium ($MA^+$), ethylammonium ($EA^+$), guanidinium ($GA^+$), $Cs^+$, $Rb^+$ and a combination thereof; the B-site divalent cation is selected from the group consisting of $Pb^{2+}$, $Sn^{2+}$, $Ge^{2+}$ and a combination thereof; and the halide anion is selected from the group consisting of $I^-$, $Br^-$, $Cl^-$ and a combination thereof.

In an optional embodiment, the halide perovskite is selected from any one of $CsPb_{0.5}Sn_{0.5}I_3$, $FAPbI_3$, $MA_{0.25}FA_{0.75}PbI_{2.2}Br_{0.6}Cl_{0.2}$, $Cs_{0.02}FA_{0.96}MA_{0.02}PbI_{0.99}Cl_{0.01}$, $MAPb_{0.92}Sn_{0.08}I_3$, $(FA_{0.95}MA_{0.05})_{0.95}Cs_{0.05}Pb(I_{0.96}Br_{0.04})_3$, $Rb_{0.1}FA_{0.8}GA_{0.1}Pb_{0.6}Ge_{0.4}I_3$, and $(FA_{0.92}MA_{0.05})_{0.9}Cs_{0.1}Pb(I_{0.92}Br_{0.08})_3$, and $Cs_{0.2}FA_{0.8}Pb(I_{0.6}Br_{0.4})_3$.

Optionally, the crystal grain structure of $[A^{+1}B^{+2}X^{-1}{}_3]$ includes grain boundaries at which the sulfonyl naphthoquinone-based compound accommodates.

It is optional that the perovskite layer contains about 0.3 mol % to about 1 mol % of the sulfonyl naphthoquinone-based compound.

In an optional embodiment, the perovskite layer further comprises about 3 mol % of $MAPbCl_3$ and 5 mol % of 4-guanidinobenzoic acid.

Optionally, the perovskite layer has a thickness of about 260 nm.

In a second aspect of the present invention, there is provided a method for fabricating the perovskite layer in accordance with the first aspect, comprising the steps of:
a) providing a solution mixture including a halide perovskite precursor and the sulfonyl naphthoquinone-based compound in accordance with the first aspect; b) spin-coating the solution mixture on a substrate; and c) annealing the spin-coated solution mixture to form the perovskite layer.

Optionally, step a) comprises the steps of: a1) providing a first reaction mixture including halides of formamidinium, methylammonium, and cesium; and a2) mixing the first reaction mixture with about 0.3 mol % to about 1 mol % of the sulfonyl naphthoquinone-based compound to form a second reaction mixture.

In an optional embodiment, the halides comprises CsI, CsBr, FAI, FABr, $PbI_2$, and $PbBr_2$.

It is optional that the first reaction mixture further comprises about 3 mol % of $MAPbCl_3$ and about 5 mol % of 4-guanidinobenzoic acid.

Optionally, step a) further comprises step a3) converting sodium anthraquinone-2-sulfonate to the sulfonyl naphthoquinone-based compound.

It is optional that step b) comprises step b1) adding an anti-solvent agent of chlorobenzene onto the center of the spin-coated solution mixture about 10 seconds before completing the spin-coating process.

Optionally, the spin-coating is performed at about 4000 rpm to about 6500 rpm with a ramping rate of about 1500 rpm si.

In an optional embodiment, the method, after step c), further comprises the steps of: spin-coating a surface passivating agent of piperazinium iodide (PI) on the perovskite layer; and annealing the PI-coated perovskite layer.

In a third aspect of the present invention, there is provided a solar cell including: a first hole transport layer; a first electron transport layer; and a first active layer of the perovskite layer in accordance with the first aspect that is disposed between the first hole transport layer and the first electron transport layer.

Optionally, the first active layer is in direct contact with the first hole transport layer and the first electron transport layer.

In an optional embodiment, the first hole transport layer is disposed on a transparent conductive layer that is disposed on a transparent substrate and the first electron transport layer is disposed on a first blocking layer that is disposed on a first metal layer.

In an embodiment of the invention, the first hole transport layer is in direct contact with a transparent conductive layer and the first electron transport layer is in direct contact with the first blocking layer.

It is optional that the transparent substrate is selected from the group consisting of glass, polymethyl methacrylate (PMMA), polycarbonate (PC), general-purpose polystyrene (GPPS), polyethylene glycol terephthalate (PET), polyethylene naphthalate (PEN), polydimethylsiloxane (PDMS), styrene-ethylene-butylene-styrene (SEBS), ethylene terephthalateco-1,4-cylclohexylenedimethylene terephthalate (PETG), acrylonitrile butadiene styrene copolymers (ABS), polypropylene (PP), polyamide (PA), acrylonitrile-styrene copolymer (AS), and a combination thereof.

Optionally, the transparent conductive layer is selected from the group consisting of Indium Tin Oxide (ITO), Aluminum Zinc Oxide (AZO), Fluorine Tin Oxide (FTO), graphene, poly(3,4-ethylenedioxythiophene):poly(styrene sulfonate) (PEDOT:PSS), Ag nanowire, Cu nanowire and a combination thereof.

It is optional that the first hole transport layer is selected from the group consisting of poly(triaryl amine) (PTAA), PEDOT:PSS, $NiO_x$, 2,2',7,7'-Tetrakis[N,N-di(4-methoxyphenyl)amino]-9,9'-spirobifluorene (Spiro-OMeTAD), DC-PA, $MoO_x$ and a combination thereof.

Optionally, the first electron transport layer is selected from the group consisting of $PC_{61}BM$, $C_{60}$, $SnO_2$, PNDIT-F3N and a combination thereof.

It is optional that the first blocking layer is selected from the group consisting of bathocuproine (BCP), bis-$C_{60}$, $SnO_x$, $Zr(acac)_2$, $MoO_x$ and a combination thereof.

Optionally, the first metal layer is selected from the group consisting of Ag, Cu, Au, Al, W, Fe, Pt and a combination thereof.

In an optional embodiment, the solar cell comprises a band gap of about 1.81 eV.

Optionally, the solar cell comprises a power conversion efficiency of about 18.98% to about 19.58%.

It is optional that the solar cell comprises a power conversion efficiency of 95% of its initial value upon AM1.5G illumination for 500 hours at about 45° C.

In an optional embodiment, the solar cell further comprises a subcell disposed on and in direct contact with the first metal layer.

It is optional that the solar cell further includes an anti-reflection layer to which the transparent conductive layer and the transparent substrate are disposed on and in direct contact therewith.

Optionally, the anti-reflection layer is selected from the group consisting of $MgF_2$, LiF, PDMS and a combination thereof.

It is optional that the subcell comprises: a second hole transport layer; a second electron transport layer; and a second active layer that is disposed between the second hole transport layer and the second electron transport layer.

In an optional embodiment, the second active layer is in direct contact with the second hole transport layer and the second electron transport layer.

Optionally, the second active layer is selected from the group consisting of a perovskite photovoltaic material, a Si photovoltaic material, a CIGS photovoltaic material, a CdTe photovoltaic material, an organic photovoltaic material and a combination thereof.

It is optional that the second hole transport layer is disposed on the first metal layer and the second electron transport layer is disposed on a second metal layer.

Optionally, the second hole transport layer is in direct contact with the first metal layer and the second electron transport layer is in direct contact with the second metal layer.

In an optional embodiment, the second hole transport layer is disposed on the first metal layer and the second electron transport layer is disposed on the second metal layer.

Optionally, the second hole transport layer is in direct contact with the first metal layer and the second electron transport layer is in direct contact with the second blocking layer.

In an optional embodiment, the solar cell comprises a perovskite-organic tandem solar cell.

Optionally, the perovskite-organic tandem solar cell comprises the first active layer of $Cs_{0.2}FA_{0.8}Pb(I_{0.6}Br_{0.4})_3$ and the second active layer of $PM6:Y6:P_{71}BM$.

It is optional that the perovskite-organic tandem solar cell has a power conversion efficiency of about 24.27% to about 25.22%.

Optionally, the perovskite-organic tandem solar cell has a power conversion efficiency of 92% of its initial value upon AM1.5G illumination for 500 hours at about 45° C.

BRIEF DESCRIPTION OF DRAWINGS

The invention will now be more particularly described, by way of example only, with reference to the accompanying drawings, in which:

FIG. 20A shows the high-resolution XPS spectra of metallic Pb ($Pb^0$) in total Pb ($Pb^{2+}+Pb^0$) element of the pristine perovskite films with different AQS derivatives;

FIG. 35B shows a table summarizing the parameters used for calculating the average carrier lifetime of I/Br mixed-halide perovskites in FIG. 35A;

FIG. 36A shows space-charge-limited current (SCLC) curves of the hole-only devices with the device structure of glass/ITO/DC-PA/perovskite (with and without AQS derivatives)/$MoO_3$/Ag);

FIG. 36B shows the corresponding calculated trap density in the perovskite films of FIG. 36A;

FIG. 39B is a table summarizing the solar cell performance for the single-junction PSCs under reverse scan (extracted from the J-V curves of FIG. 39A);

FIG. 42B is a table summarizing the reported $V_{oc}$ values for the PSCs with the bandgap of approximately 1.80 eV corresponding to FIG. 42A;

FIG. 46B is a table summarizing the device performance of the champion PO-TSC under reverse and forward scans;

FIG. 52A to 52E show the certified results of the tandem solar cell measured at SIMIT (CNAS). The certified PCE is 24.3% with a certified aperture area of 0.0419 $cm^2$;

FIG. 53 is table summarizing the device performance of the reported PO-TSCs and the PO-TSC of the present invention.

DETAILED DESCRIPTION OF OPTIONAL EMBODIMENT

Figure 1A:
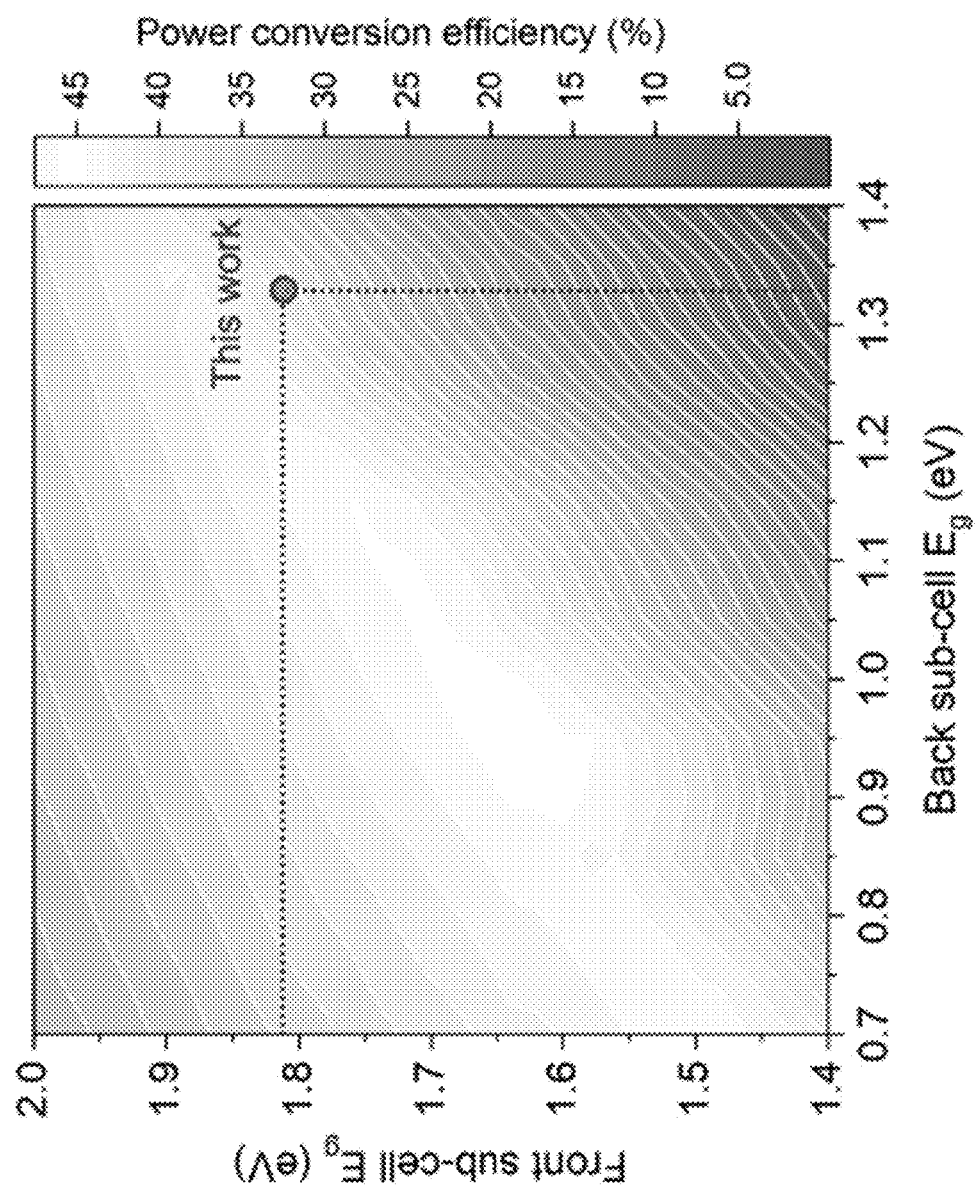
FIG. 1A shows the theoretically achievable efficiency for two-junction solar cells with a 2-terminal configuration.

As used herein, the forms "a", "an", and "the" are intended to include the singular and plural forms unless the context clearly indicates otherwise.

The words "example" or "exemplary" used in this invention are intended to serve as an example, instance, or illustration. Any aspect or design described in this disclosure as "exemplary" is not necessarily to be construed as preferred or advantageous over other aspects or designs. Rather, use of the words "example" or "exemplary" is intended to present concepts in a concrete fashion. As used in this application, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances.

As used herein, the phrase "about" is intended to refer to a value that is slightly deviated from the value stated herein. In one example, the expression "about 10 seconds" encompasses any values from 9.5 seconds to 10.5 seconds, such as 9.5, 9.55, 9.85, 10.0, 10.02, 10.2 . . . 10.5 seconds. In another example, the expression "about 1 mol %" encompasses any value from 0.8 mol % to 1.2 mol % such as 0.8, 0.85, 0.88, 0.95 . . . 1 . . . 1.05 . . . 1.2 mol %. In still another example, the expression of "about 0.3 mol %" encompasses any value from 0.28 mol % to 0.32 mol %, such as 0.28, 0.285, 0.29, 0.292 . . . 0.3 . . . 0.305, 0.31 . . . 0.32 mol %. In a further example, the expression of "about 260 nm" encompasses any value from 255 nm to 265 nm, such as 255, 255.5, 256, 256.2 . . . 260 . . . 262, 263.5, 264 . . . 265 nm. In a still further example, the expression of "about 4000 rpm" encompasses any value from 3900 rpm to 4100 rpm, such as 3900, 3910, 3955 . . . 0.4000, 4005, 4050 . . . 4100 rpm.

The halide oxidation mechanism is considered as the one of the models that may rationalize the halide segregation behavior in perovskites. In particular, it is believed that upon illumination, preferential iodide oxidation occurs in I/Br mixed perovskites, leading to local concentration gradients of its oxidized products (e.g., $I_2$ and HI), which in turn drive halide migration. Furthermore, it is also believed that $Pb^{2+}$ ions in perovskites are prone to be reduced to metallic $Pb^0$ under continuous illumination, which is detrimental to device efficiency and stability.

Without intending to be limited by theory, the inventors have, through their own research, trials, and experiments, devised an active layer for solar cell, particularly a perovskite layer comprising a mixture of a halide perovskite and a sulfonyl naphthoquinone-based compound (or in other words a perovskite layer formed by mixing a halide perovskite and a sulfonyl naphthoquinone-based compound), that may be capable of effectively suppressing halide segregation of the active layer. In particular, in an example embodiment, it is found that the PSC equipped with the perovskite layer of the present invention may obtain a power conversion efficiency (PCE) of 19.58% with an open-circuit voltage ($V_{oc}$) of 1.351 V, while showing significantly improved long-term stability ($T_{95}$~500 hours under maximum power point (MPP) tracking. In another example embodiment, the monolithic perovskite-organic tandem solar cell (PO-TSC) containing the perovskite layer of the present invention may have a PCE of 25.22% (certified 24.27%) and 92% of its initial PCE retained after operation for 500 hours.

According to the present invention, there is provided a perovskite layer for use in a solar cell comprising a mixture of a halide perovskite and a sulfonyl naphthoquinone-based compound having a structure of Formula (I):

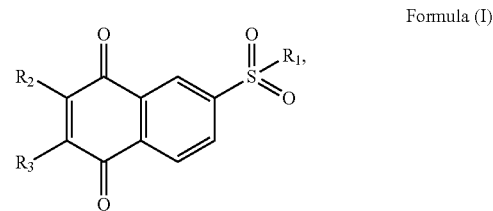

Formula (I)

wherein:

$R_1$ is independently selected from one of OM, $OR_4$, and $NR_5R_6$, with M being a cation, $R_4$, $R_5$ and $R_6$ being independently selected from a hydrogen and a substituent; $R_2$ and $R_3$ are independently selected from a hydrogen and a substituent, or $R_2$ and $R_3$ may form a fused ring.

In an embodiment, M is selected from the group consisting of $H^+$, $Na^+$, $K^+$, $Cs^+$, $Rb^+$, $Sr^{2+}$, $Ca^{2+}$, $Ni^{2+}$, $Cu^{2+}$, $Co^{2+}$, $Zn^{2+}$, $Mg^{2+}$, $Ba^{2+}$, $Li^+$, ammonium ion, and aminum ion; $R_2$, $R_3$, $R_4$, $R_5$ and $R_6$ are independently selected from the group consisting of hydrogen, substituted or unsubstituted C1 to C4 alkyl, substituted or unsubstituted C2 to C6 alkenyl, substituted or unsubstituted C2 to C6 alkynyl, halogen, substituted or unsubstituted C6 to C10 aryl, —CN, —C(=O)OH, —C(=O)H, —C(=O)$R_7$, —$OR_7$, —SH, —SR₇, —NH₂, —NHR₆, —N(R₇)₂, —Si(R₇)₃, —OSi(R₇)₃, —S(O)OH and —P(O)(OH)₂ where R₇ is an alkyl or a phenyl; and when R₂ and R₃ form a fused ring, it comprises a substituted or unsubstituted 6-membered to 14-membered ring.

In an embodiment, the unsubstituted C1 to C4 alkyl may include methyl, ethyl, propyl, butyl, isopropyl, isobutyl, t-butyl, n-butyl and the like. In an embodiment, the unsubstituted C2 to C6 alkenyl may include ethenyl, 1-propenyl, 2-propenyl (allyl), isopropenyl, 2-methyl-1-propenyl, 1-butenyl, 2-butenyl and the like. In an embodiment, the unsubstituted C2 to C6 alkynyl may include ethynyl, propynyl, but-1-ynyl, but-2-ynyl, pent-1-ynyl, pent-2-ynyl, hex-1ynyl, hex-2ynyl, hex-3ynyl and the like. In an embodiment, the unsubstituted C6 to C10 aryl may include unsubstituted C6 to C10 homoaryl such as phenyl, naphthyl, tetrahydronaphthyl, indanyl and the like. In an embodiment, the unsubstituted C6 to C10 aryl may include unsubstituted C6 to C10 heteroaryl such as pyridyl, pyrazinyl, pyrimidinyl, pyridazinyl, quinolyl, isoquinolyl, benzothienyl, benzofuryl, indolyl, pyridine, pyrimidone, pyrazinone, pyrimidinone and the like.

In an embodiment, one or more hydrogen of the above substituents, i.e., C1 to C4 alkyl, C2 to C6 alkenyl, C2 to C6 alkynyl, and C6 to C10 aryl, may be substituted by one or more of the following moiety such as halogen (e.g. F, Cl, Br), —CN, —CF₃, alkenyl (e.g., —CH=CH₂, —CH=C(CH₃)₂, and the like), alkynyl (e.g., —C≡CH, —C≡CCH₃, and the like), —C(=O)OH, —C(=O)H, —C(=O)R₈, —OR₈, —SH, —SR₈, —NH₂, —NHR₈, —N(R₇)₈, —Si(R₈)₃, —OSi(R₈)₃, —S(O)OH and —P(O)(OH)₂, where R₈ is C1 to C4 alkyl as defined herein or a phenyl.

In an embodiment where R₂ and R₃ form a fused ring, it may comprise a unsubstituted 6-membered to 14-membered ring such as phenyl, anthracene, tetrahydronaphthyl, indanyl and the like or substituted 6-membered to 14-membered ring in which one or more hydrogen of the unsubstituted 6-membered to 14-membered ring is substituted with, for example, phenyl, carbonyl, primary amine, secondary amine and the like.

In an embodiment, the sulfonyl naphthoquinone-based compound may be any one of Formula (II), (III), (IV), (V), (VI), or (VII):

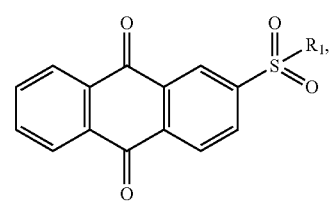

Formula (II)

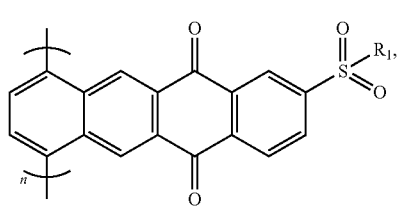

Formula (III)

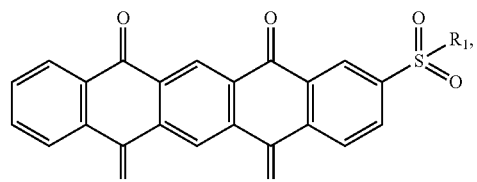

Formula (IV)

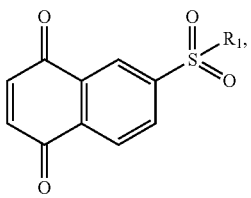

Formula (V)

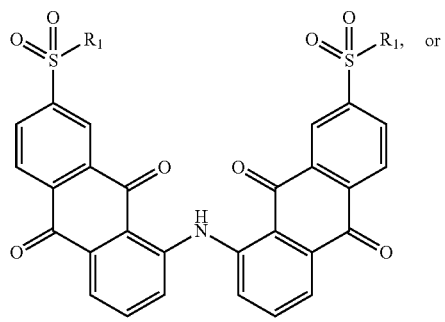

Formula (VI)

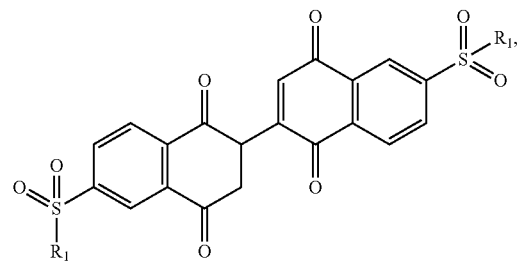

Formula (VII)

with R₁ as defined above; and n being 1-1000.

In a particular embodiment where the sulfonyl naphthoquinone-based compound has a structure of Formula (II), it may be selected from any one of Formula (VIII), Formula (IX), or Formula (X):

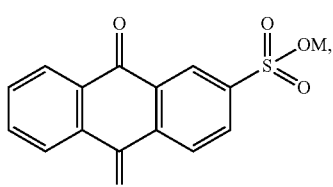

Formula (VIII)

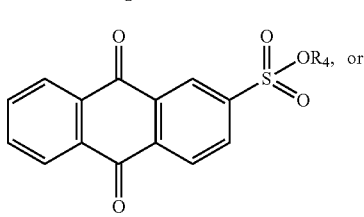

Formula (IX)

Formula (X)

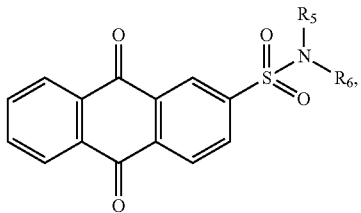

with M being $H^+$, ammonium ion or aminum ion; $R_4$ being C1 to C4 alkyl; $R_5$ and $R_6$ being independently selected from hydrogen and C1 to C4 alkyl. The term "aminum ion" generally denotes a substituted ammonium ion formed by substituting one or more hydrogen atom in the ammonium ion with one or more organic groups such as an alkyl group (e.g. methyl, ethyl, propyl, phenylethyl, t-butyl, etc.), a benzyl group, a phenyl group and the like. C1 to C4 alkyl may include aliphatic hydrocarbons with straight chains and branched chains, and having 1 to 4 carbon atoms, such as methyl, ethyl, propyl, butyl, isopropyl, isobutyl, t-butyl, n-butyl and the like.

Preferably, the sulfonyl naphthoquinone-based compound of Formula (VIII) is selected from any one of Formula (VIIIa), (VIIIb), and (VIIIc):

Formula (VIIIa)

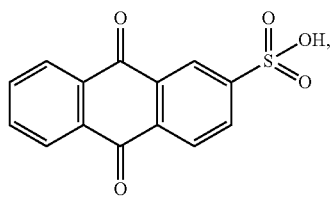

Formula (VIIIb)

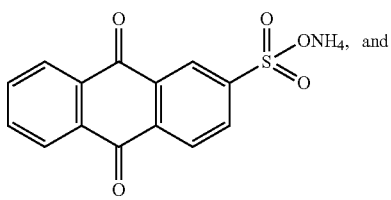

Formula (VIIIc)

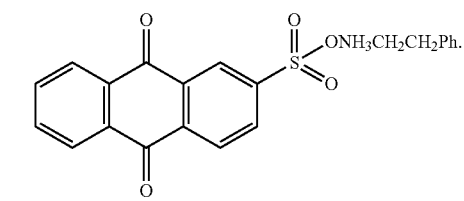

In particular, it is found that upon changing the cation M from $H^+$ to $NH_4^+$ and phenylammonium (PEA) ion ($PhCH_2CH_2NH_3^+$), it may enhance the passivation effect of the sulfonyl naphthoquinone-based compound, which in turn enhancing its ability to stabilize the perovskite upon operation, such as showing a stronger binding (e.g. higher binding energy) toward the redox components of the perovskite (e.g. $Pb^{2+}$) upon operation. As a result, it may further facilitate the long-term operation of the perovskite. Details of the stabilization effect of the sulfonyl naphthoquinone-based compound will be discussed in the later part of the present disclosure.

In an optional embodiment, the sulfonyl naphthoquinone-based compound may comprise a structure of Formula (IXa):

Formula (IXa)

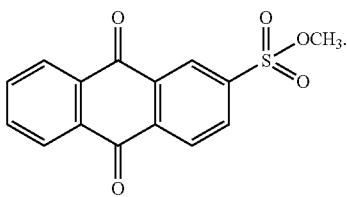

In another optional embodiment, the sulfonyl naphthoquinone-based compound may comprise a structure of Formula (Xa):

Formula (Xa)

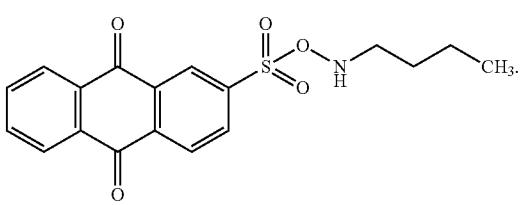

The halide perovskite of the perovskite layer may comprise a crystal grain structure of $[A^{+1}B^{+2}X^{-1}{}_3]$, with $A^{+1}$ being an A-site monovalent cation, $B^{+2}$ being a B-site divalent cation, and $X^{-1}$ being a halide anion.

In an embodiment, the A-site monovalent cation is selected from the group consisting of formamidinium ($FA^+$), methylammonium ($MA^+$), ethylammonium ($EA^+$), guanidinium ($GA^+$), $Cs^+$, $Rb^+$ and a combination thereof; the B-site divalent cation is selected from the group consisting of $Pb^{2+}$, $Sn^{2+}$, $Ge^{2+}$ and a combination thereof; and the halide anion is selected from the group consisting of $I^-$, $Br^-$, $Cl^-$ and a combination thereof.

In a particular embodiment, the halide perovskite is selected from any one of $CsPb_{0.5}Sn_{0.5}I_3$, $FAPbI_3$, $MA_{0.25}FA_{0.75}PbI_{2.2}Br_{0.6}Cl_{0.2}$, $Cs_{0.02}FA_{0.96}MA_{0.02}PbI_{0.99}Cl_{0.01}$, $MAPB_{0.92}SN_{0.05}I_3$, $(FA_{0.95}MA_{0.05})_{0.95}CS_{0.05}PB(I_{0.96}BR_{0.04})_3$, $RB_{0.1}FA_{0.8}GA_{0.1}PB_{0.6}GE_{0.4}I_3$, and $(FA_{0.92}MA_{0.05})_{0.9}Cs_{0.1}Pb(I_{0.92}Br_{0.08})_3$, and $Cs_{0.2}FA_{0.8}Pb(I_{0.6}Br_{0.4})_3$. Preferably, the halide perovskite may be an I/Br mixed perovskite. As a specific embodiment, the halide perovskite may be $Cs_{0.2}FA_{0.8}Pb(I_{0.6}Br_{0.4})_3$.

The term "crystal grain" (or crystallite) generally denotes small or microscopic crystals that are oriented/grown in random or no preferred direction, forming grain boundaries at areas/interfaces that the crystallites meet. In an embodiment, the crystal grain structure of $[A^{+1}B^{+2}X^{-1}{}_3]$ may include grain boundaries at which the sulfonyl naphthoquinone-based compound accommodates, and at which the sulfonyl naphthoquinone-based compound acts as a redox mediator which enables selective reduction of $I^0$ and oxidation of $Pb^0$ at the same time though electron shuttling.

The content/concentration of the sulfonyl naphthoquinone-based compound in the perovskite layer may vary/adjust in accordance with practical needs. In an embodiment, the perovskite layer may contain about 0.3 mol % to about 1 mol %, about 0.29 mol % to about 1.1 mol %, about 0.31 mol % to about 1 mol %, about 0.3 mol % to about 0.9 mol %, about 0.3 mol % to about 0.8 mol %, about 0.32 mol % to about 0.75 mol %, about 0.3 mol % to about 0.7 mol %, about 0.31 mol % to about 0.65 mol %, about 0.3 mol % to about 0.6 mol %, about 0.31 mol % to about 0.52 mol % or particularly about 0.3 mol % to about 0.5 mol % of the sulfonyl naphthoquinone-based compound.

In an additional or optional embodiment, the perovskite layer may further comprise about 3 mol % of MAPbCl$_3$ and 5 mol % of 4-guanidinobenzoic acid, which, in particular, act as passivating agents to (in addition to the activity of the redox mediator) further passivate the defect in the perovskite layer as discussed herein. Advantageously, it is appreciated that these passivating agents may be distributed at the grain boundaries of the perovskite layer without disturbing the chemical composition of the perovskite layer (i.e. without leading to substantial change of the chemical composition of the perovskite layer).

In an embodiment, the perovskite layer may have a thickness of about 200 nm to about 280 nm, about 205 nm to about 285 nm, about 210 nm to about 275 nm, about 220 nm to about 270 nm, about 220 nm to about 268 nm, about 240 nm to about 268 nm, about 255 nm to about 268 nm, about 258 nm to about 268 nm, or particularly about 260 nm.

The method for fabricating the perovskite layer as described herein is now disclosed. The method may comprise the steps of:
a) providing a solution mixture including a halide perovskite precursor and the sulfonyl naphthoquinone-based compound as described herein such as the sulfonyl naphthoquinone-based compound having a structure of Formula (VIII), Formula (IX), or Formula (X);
b) spin-coating the solution mixture on a substrate; and
c) annealing the spin-coated solution mixture to form the perovskite layer.

Step a) may comprises the steps of: a1) providing a first reaction mixture including halides of formamidinium, methylammonium, and cesium; and a2) mixing the first reaction mixture with about 0.3 mol % to about 1 mol % of the sulfonyl naphthoquinone-based compound to form a second reaction mixture.

For example, in an embodiment, the halides may comprise CsI, CsBr, FAI, FABr, PbI$_2$, and PbBr$_2$. These halides may be dissolved in a solvent mixture such as DMF/DMSO (e.g., v/v, 4:1) to form the first reaction mixture. Then, about 0.3 mol % to about 1 mol % of the sulfonyl naphthoquinone-based compound such as any one of the sulfonyl naphthoquinone-based compound having a structure of Formula (VIII), Formula (IX), or Formula (X) may be mixed with the first reaction mixture to form a second reaction mixture. Optionally or additionally, the second reaction mixture may be stirred for at least 8 hours to obtain a homogeneous/uniform solution mixture before proceeding to the spin coating step (i.e., step b)).

In an additional or optional embodiment, the first reaction mixture may further comprise about 3 mol % of MAPbCl$_3$ and 5 mol % of 4-guanidinobenzoic acid. For example, the MAPbCl$_3$ and 4-guanidinobenzoic acid may be added to the first reaction mixture comprising halides of formamidinium, methylammonium, and cesium before proceeding to step a2).

It is optional that the sulfonyl naphthoquinone-based compound may be obtained from commerce or by way of synthesis. In an optional embodiment where the sulfonyl naphthoquinone-based compound is obtained by way of synthesis, the method for fabricating the presently claimed perovskite layer may further comprise step a3) which involves converting sodium anthraquinone-2-sulfonate to the sulfonyl naphthoquinone-based compound as described herein.

In an embodiment, the sodium anthraquinone-2-sulfonate may be converted to the sulfonyl naphthoquinone-based compound having a structure of Formula (VIIa) by way of ion-exchange. For example, the sodium anthraquinone-2-sulfonate may be mixed with a aqueous solution of an cation exchange resin such as Amberlite cation exchange resin (IR-120 hydrogen form), followed by stirring for at least 8 hours. The mixture may be further subjected to isolation over a cation exchange column with the Amberlite cation exchange resin.

In another embodiment, the sodium anthraquinone-2-sulfonate may be converted to the sulfonyl naphthoquinone-based compound having a structure of Formula (VIIb) or Formula (VIIc). For example, the sodium anthraquinone-2-sulfonate may be converted to the sulfonyl naphthoquinone-based compound having a structure of Formula (VIIa) as described above. Then, the sulfonyl naphthoquinone-based compound of Formula (VIIa) may be converted to the sulfonyl naphthoquinone-based compounds of Formula (VIIb) and Formula (VIIb) by reacting the sulfonyl naphthoquinone-based compound of Formula (VIIa) with corresponding amine or ammonium salt, such as ammonium hydroxide and phenethylamine, and stirred for at least 8 hours, followed by drying under reduced pressure such as under vacuum.

In an optional embodiment, the sodium anthraquinone-2-sulfonate may be converted to anthraquinone-2-sulfonyl chloride, followed by further converting to the sulfonyl naphthoquinone-based compound having a structure of Formula (IXa) or Formula (Xa). For example, the sodium anthraquinone-2-sulfonate may be mixed with thioyl chloride in DMF to form a reaction mixture, followed by isolating the crude/raw anthraquinone-2-sulfonyl chloride from the reaction mixture by way of precipitation and filtration. The crude/raw anthraquinone-2-sulfonyl chloride may be optionally purified by washing with suitable solvent prior to further reaction.

For converting the anthraquinone-2-sulfonyl chloride to the sulfonyl naphthoquinone-based compound having a structure of Formula (IXa), for example, it may commence with mixing the anthraquinone-2-sulfonyl chloride with methanol under a solvent such as DMF, and stirring the mixture for, e.g., 2 hours at a temperature of about 50° C. to about 60° C., followed by isolating the crude/raw sulfonyl naphthoquinone-based compound of Formula (IXa) by way of precipitation and optionally filtration, and purification over column chromatography with an eluting solvent of, for instance, 0.5% methanol in dichloromethane (DCM).

On the hand, to convert the anthraquinone-2-sulfonyl chloride to the sulfonyl naphthoquinone-based compound having a structure of Formula (Xa), it may, for example, adding butylamine slowly (e.g. dropwise) to a DCM solution of the anthraquinone-2-sulfonyl chloride at a reduced temperature such as at 0° C. The reaction mixture may be stirred for, e.g., 2 hours at room temperature, followed by washing the crude/raw product with suitable solvent and purifying the crude/raw product over column chromatography with an eluting solvent of, for instance, 0.5% methanol in dichloromethane (DCM).

Turning to step b), the solution mixture (of step a)) may be spin-coated onto a substrate, such as a transparent substrate (e.g., glass, PDMS, PET, ITO, FTO, etc.), a hole transport layer, an electron transport layer and the like or a combination thereof at about 300 rpm to about 12000 rpm for about 10 seconds to about 140 seconds. In an embodiment, the spin-coating may be performed at about 4000 rpm to about 6500 rpm with a ramping rate of about 1500 rpm s$^{-1}$. During the spin-coating process and/or before the completion of the spin-coating process, such as prior 3 seconds to about 35 seconds of said completion, an anti-solvent agent may be added onto the spin-coated solution mixture. It is believed that the anti-solvent treatment would increase the nucleus density during the perovskite layer/film formation and thus is beneficial to produce uniform and pinhole-free perovskite layer/film. In an embodiment, the addition of anti-solvent agent may commence in step b1) in which an anti-solvent agent of chlorobenzene is added onto the center of the spin-coated solution mixture about 10 seconds before completing the spin-coating process.

Preferably, unless specified, it is appreciated that the spin coating processes as described herein are performed in an N$_2$-filled glovebox with the contents of O$_2$ and H$_2$O<5 ppm at a controlled temperature of about 20° C.

After that, the method may proceed to step c) annealing the spin-coated solution mixture to form the perovskite layer. For example, the spin-coated solution mixture (including the substrate) may be transferred to a hotplate and subjected to annealing at a temperature of about 65° C. to about 180° C., about 80° C. to about 180° C., about 80° C. to about 150° C., about 90° C. to about 150° C., about 95° C. to about 150° C., about 100° C. to about 120° C., about 100° C. to about 115° C., or about 100° C. to about 110° C. for about 6 min to about 120 min. It is believed that the annealing/heating process may be beneficial to the perovskite crystallization and consequently leading to higher power conversion efficiency upon (solar cell) operation. In an embodiment, the spin-coated solution mixture may be annealed at about 100° C. for about 15 min.

In an additional or optional embodiment, the method for fabricating the perovskite layer as described herein may further comprise the steps of: spin-coating a surface passivating agent of piperazinium iodide (PI) on the perovskite layer; and annealing the PI-coated perovskite layer. For example, a solution of PI such as an IPA (isopropyl alcohol) solution of PI may be spin-coated onto the perovskite layer as formed in step c), at a rate of about 5000 rpm for about 30 seconds. The PI-coated perovskite layer may then be annealed/heated at a temperature of about 100° C. for about 10 min. It is believed that the addition of PI may improve the band alignment and enhance charge extraction at the interface of the perovskite layer and the electron transport layer by creating a positive dipole, which may in turn enhancing the performance of the solar cell as a result.

A further aspect of the present invention pertains to a solar cell, in particular a solar cell including the perovskite layer as described herein. In an embodiment, the solar cell may include: a first hole transport layer; a first electron transport layer; and a first active layer of the perovskite layer as described herein that is disposed between the first hole transport layer and the first electron transport layer, such as the solar cell 100 as exemplified in FIG. 1B.

As shown, the solar cell 100 has a first hole transport layer 104, a first electron transport layer 106, and a first active layer of the perovskite layer 108 as described herein, which is disposed between the first hole transport layer 104 and the first electron transport layer 106. In particular, the first active layer 108 is in direct contact with the first hole transport layer 104 and the first electron transport layer 106, forming a layered/stacked structure.

Figure 1B:
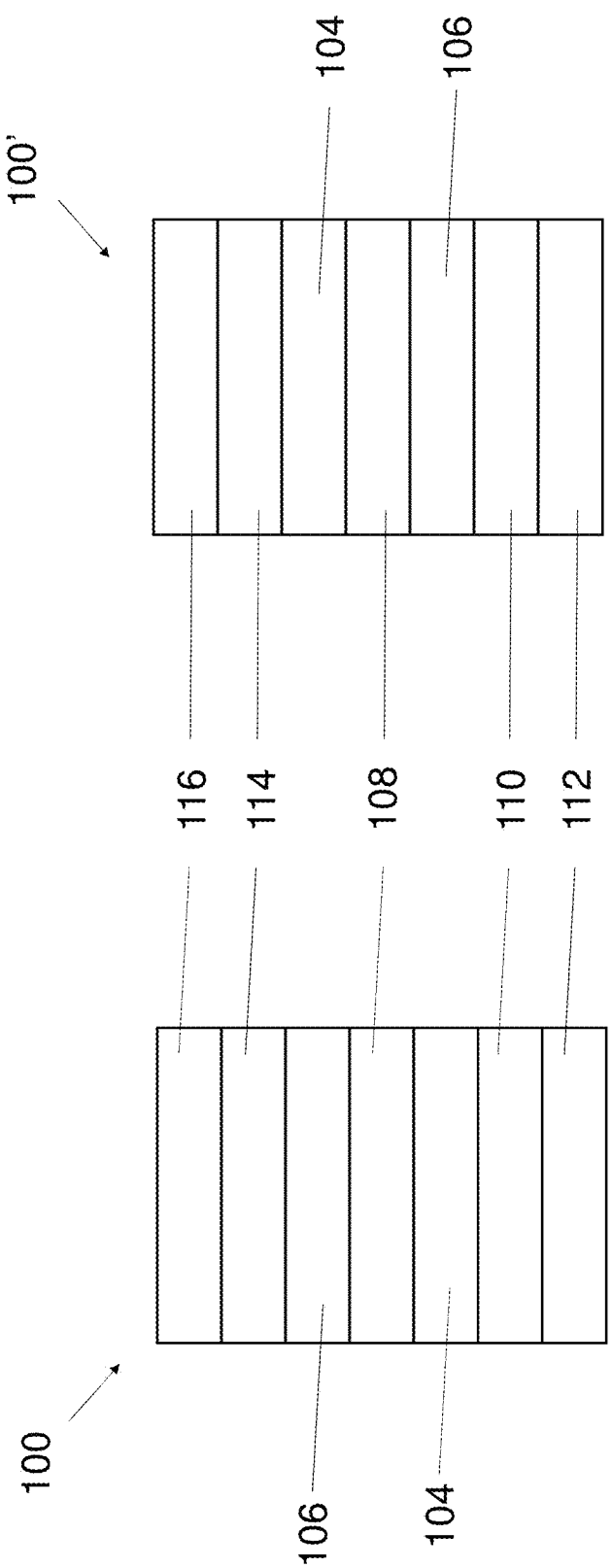
FIG. 1B is a schematic diagram illustrating the exemplary solar cell in accordance with an embodiment of the present invention.

The first hole transport layer may be disposed on a transparent conductive layer that may be disposed on a transparent substrate and the first electron transport layer may be disposed on a first blocking layer that may be disposed on a first metal layer. For example, in this embodiment, the first hole transport layer 104 is in direct contact with the transport conductive layer 110 that is disposed on the transparent substrate 112, and the first electron transport layer 106 is in direct contact with the first blocking layer 114 that is disposed on the first metal layer 116 (FIG. 1B).

In an alternative embodiment, the solar cell 100 may be configured to have the position of the first hole transport layer 104 switched with the first electron transport layer 106, forming a solar cell 100'. That said, in this alternative embodiment, the first electron transport layer 106 is in direct contact with the transport conductive layer 110 that is disposed on the transparent substrate 112, and the first hole transport layer 104 is in direct contact with the first blocking layer 114 that is disposed on the first metal layer 116 (FIG. 1B).

As mentioned herein, the perovskite layer of the present invention is advantageous in enhancing the device (i.e., solar cell) efficiency and stability. For example, in an embodiment where the solar cell 100/100' may be a perovskite solar cell such as a single-junction perovskite solar cell comprising a band gap of, e.g. about 1.81 eV, and may comprise a power conversion efficiency (PCE) of about 18.98% to about 19.58%. In another embodiment, the solar cell may comprise a power conversion efficiency of 95% of its initial value upon AM1.5G illumination for 500 hours at about 45° C. Detailed performance of the solar cell will be discussed in the later part of the present disclosure.

Figure 1C:
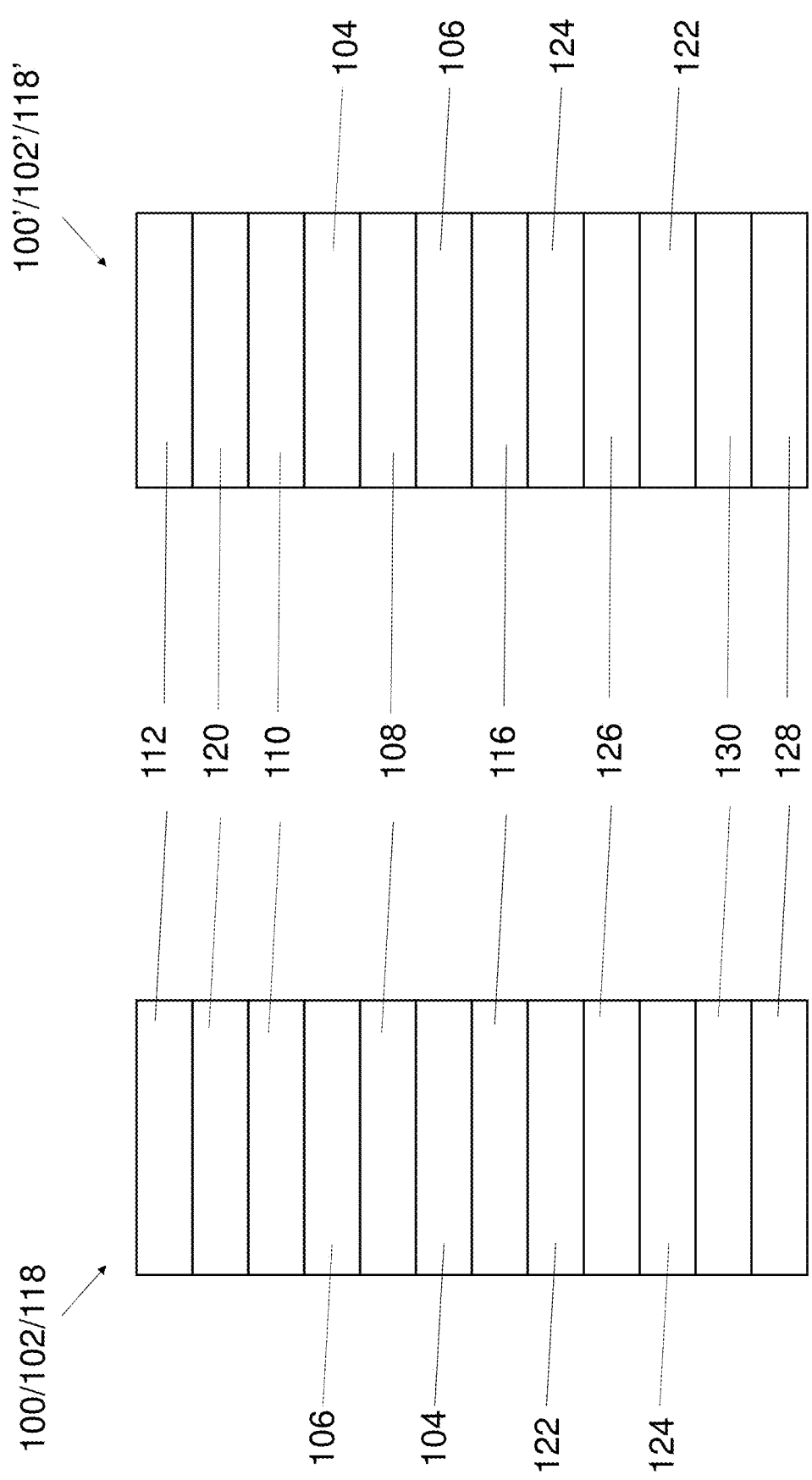
FIG. 1C is a schematic diagram illustrating the exemplary solar cell in accordance with an embodiment of the present invention.

In an embodiment, the solar cell 100 may further comprise a subcell disposed thereon, forming a tandem solar cell. Referring to FIG. 1C, there is provided an exemplary configuration of a tandem solar cell 102. As shown, the tandem solar cell 102 includes the solar cell 100 and a subcell 118 disposed on the solar cell 100, in particular in direct contact with the first metal layer 116. In other words, in this embodiment, the solar cell 100 acts as a first subcell 102 in the tandem solar cell 102. The tandem solar cell 102 further includes an anti-reflection layer 120 to which the transparent conductive layer 110 and the transparent substrate 112 are disposed on and in direct contact therewith.

In this embodiment, the subcell 118 includes a second hole transport layer 122, a second electron transport layer 124, and a second active layer 126 that is disposed between, in particular, in direct contact with the second hole transport layer 122 and the second electron transport layer 124, forming a layered/stacked structure. The second hole transport layer 122 may be disposed on the first metal layer 116 and the second electron transport layer 124 may be disposed on a second metal layer 128.

In particular, it is appreciated that depending on the configuration of the solar cell 100, the second hole transport layer 122 and the second electron transport layer 124 may be configured differently. For example, in this embodiment, the second hole transport layer 122 is in direct contact with the first metal layer 116 and the second electron transport layer 124 is in direct contact with the second metal layer 128.

In an alternative embodiment where the tandem solar cell 102' includes the solar cell 100', the subcell may be a subcell 118' in which the position of second hole transport layer 122 is switched with that of the second electron transport layer 124. That said, in this alternative embodiment, the second electron transport layer 124 is in direct contact with the first metal layer 116 and the second hole transport layer 122 is in direct contact with the second metal layer 128 (FIG. 1C).

In an optional or additional embodiment, the subcell 118/118' may further include a second blocking layer 130 disposed between the second ETL 124/second HTL 122 and the second metal layer 128 (FIG. 1C). Preferably, the second blocking layer 130 is in direct contact with the second ETL 124/second HTL 122 and the second metal layer 128.

In an embodiment, the second active layer may be selected from the group consisting of a perovskite photovoltaic material, a Si photovoltaic material, a CIGS photovoltaic material, a CdTe photovoltaic material, an organic photovoltaic material and a combination thereof.

In an example embodiment, the second active layer may be made of an organic photovoltaic material such as PM6:Y6:$P_{71}$BM. In a particular example embodiment, the subcell which includes the second active layer of PM6:Y6:$P_{71}$BM may be coupled with a solar cell which includes a first active layer of the perovskite layer as described herein, such as $Cs_{0.2}FA_{0.8}Pb(I_{0.6}Br_{0.4})_3$ to form a perovskite-organic tandem solar cell. In that particular embodiment, the tandem solar cell may have a power conversion efficiency of about 24.27% to about 25.22%, and a power conversion efficiency of 92% of its initial value upon AM1.5G illumination for 500 hours at about 45° C. Detailed performance of the tandem solar cell will be discussed in the later part of the present disclosure.

In some embodiments, the transparent substrate 112 may be flexible or rigid, and may have a light transmittance greater than about 80% (at 550 nm). In some particular embodiments, the transparent substrate may be selected from the group consisting of glass, polymethyl methacrylate (PMMA), polycarbonate (PC), general-purpose polystyrene (GPPS), polyethylene glycol terephthalate (PET), polyethylene naphthalate (PEN), polydimethylsiloxane (PDMS), styrene-ethylene-butylene-styrene (SEBS), ethylene terephthalateco-1,4-cylclohexylenedimethylene terephthalate (PETG), acrylonitrile butadiene styrene copolymers (ABS), polypropylene (PP), polyamide (PA), acrylonitrile-styrene copolymer (AS), and a combination thereof. In a more particular embodiment, the transparent substrate may be selected from any one of glass, PET, PEN, PDMS, SEBS, PP and a combination thereof. In a preferred embodiment, the transparent substrate may be selected from any one of glass, PET, PEN PDMS and a combination thereof. As a specific embodiment, the transparent substrate may be glass.

In some embodiments, the transparent conductive layer (TCL) 110 may preferably have a resistance of about 5Ω $sq^{-1}$ to about 70Ω $sq^{-1}$, for example, from about 5Ω $sq^{-1}$ to about 20Ω $sq^{-1}$, or from about 5Ω $sq^{-1}$ to about 15Ω $sq^{-1}$. It is believed that the resistance of less than about 5Ω $sq^{-1}$ may affect the transparency of the conductive layer, whereas the resistance higher than about 70Ω $sq^{-1}$ may affect the charge transfer of the devices. In particular, the TCL may be selected from the group consisting of Indium Tin Oxide (ITO), Aluminum Zinc Oxide (AZO), Fluorine Tin Oxide (FTO), graphene, poly(3,4-ethylenedioxythiophene):poly(styrene sulfonate) (PEDOT:PSS), Ag nanowire, Cu nanowire and a combination thereof. In an embodiment, the TCL may be selected from any one of ITO, FTO, PEDOT:PSS, and a combination thereof. In another embodiment, the TCL may be selected from any one of ITO and FTO. As a specific embodiment, the TCL may be ITO.

In some embodiments, the first hole transport layer (HTL) 104 and the second HTL 122 may be independently selected from the group consisting of poly(triaryl amine) (PTAA), PEDOT:PSS, NiOx, 2,2',7,7'-Tetrakis[N,N-di(4-methoxyphenyl)amino]-9,9'-spirobifluorene (Spiro-OMeTAD), p-type self-assembled monolayer (DC-PA), $MoO_x$ and a combination thereof. In an embodiment, the first and the second HTL may be independently selected from any one of PTAA, NiOx, Spiro-OMeTAD, DC-PA, $MoO_x$ and a combination thereof.

In some embodiments, the first electron transport layer (ETL) 126 and the second ETL 124 may be independently selected from the group consisting of $PC_{61}BM$, $C_{60}$, $SnO_2$, PNDIT-F3N and a combination thereof.

In some embodiments, the first blocking layer 114 and the second blocking layer 130 may be independently selected from the group consisting of bathocuproine (BCP), bis-$C_{60}$, $SnO_x$, $Zr(acac)_2$, $MoO_x$ and a combination thereof. In particular, it is appreciated that when the blocking layer is disposed on top of an ETL, it may be referred as a "hole blocking layer" which is intended to block minority charge carriers such as hole in this case, to cathode. The hole blocking layer may be selected from any one of BCP, Bis-$C_{60}$, $SnO_x$, and $Zr(acac)_2$. In contrast, when the blocking layer is disposed on top of a HTL, it may be referred as an "electron blocking layer" which is intended to block minority charge carrier such as electron in this case to anode. The electron blocking layer may be $MoO_x$.

In some embodiments, the anti-reflection layer 120 may be selected from the group consisting of $MgF_2$, LiF, PDMS and a combination thereof. In a particular embodiment, the anti-reflection layer may be selected from any one of $MgF_2$, PDMS and a combination thereof. As a specific embodiment, the anti-reflection layer may be $MgF_2$.

In some embodiments, the first metal layer 116 and the second metal layer 128 may be independently selected from the group consisting of Ag, Cu, Au, Al, W, Fe, Pt and a combination thereof. In particular, the first metal layer and the second metal layer may be independently selected from any one of Ag, Cu, Au, Al, and a combination thereof. It is appreciated that the metal layers may be referred as an electrode or a charge recombination layer depending on the position/configuration of the metal layer within the solar cell. For example, it is appreciated that when the metal layer is an intermediate layer connecting two solar cells or subcells, such as the first metal layer 116 in the tandem solar cell 102, such metal layer may be referred as a "charge recombination layer". In contrast, when the metal layer is disposed/positioned/configured at the uppermost or lowermost of the solar cell, such as the first metal layer 116 in solar cell 100 and the second metal layer 128 in the tandem solar cell 102, such metal layer may be referred as an "electrode".

The solar cell of the present invention may be fabricated by typical method such as the method as described below.

Typically, the fabrication of solar cell may include the steps of: providing a substrate; depositing the substrate with a transparent conductive layer; optionally cleaning and drying the deposited substrate; spin-coating a hole transport layer onto the transparent conductive layer; spin-coating an active layer onto the hole-transport layer; and thermally evaporating an electron-transport layer and a metal layer.

The substrate deposited with the transparent conductive layer, such as the substrate 112 deposited with the TCL 110, may be sequentially cleaned by sonication with detergent, deionized water, acetone, and isopropyl alcohol for about 15 min to about 90 min, respectively. Then, the substrate may be dried at about 40° C. to about 125° C. in oven for at least about 1 h. The cleaned and dry substrate may be treated with oxygen plasma for about 10 min to about 75 min and then transferred into a $N_2$-filled glovebox before subsequent spin-coating process.

The HTL such as the first HTL 104 and the second HTL 122 may be spin-coated onto the transparent conductive layer at about 1000 rpm to about 10000 rpm for 5 s to about 90 s, followed by annealing at about 75° C. to about 180° C. for about 5 min to about 90 min. It is believed that the spinning rate, times, and annealing temperature may affect the hole-transport layer's formation, thickness and conductivity. In some embodiments, the spin-coating may be performed at about 2000 rpm to about 8000 rpm for about 10 seconds to about 60 seconds, and the annealing temperature may be from about 80° C. to about 150° C.

The active layer such as the first active layer 108 and the second active layer 126 may be spin-coated onto the HTL at about 300 rpm to about 12000 rpm for about 10 s to about 140 s. Additionally or optionally, an anti-solvent agent may be slowly dripped onto the center of the spin-coated active layer at about 3 s to about 35 s before the end of spin-coating. The spin-coated active layer may then be transferred to the hotplate for annealing at about 65° C. to about 180° C. for about 6 min to about 120 min.

The ETL such as the first ETL 106 and the second ETL 124, the blocking layer such as the first blocking layer 114 and the second blocking layer 130, and the metal layer such as the first metal layer 116 and the second metal layer 130 may be deposited by thermal evaporation under high vacuum (e.g., <about $5 \times 10^{-6}$ Torr). It is believed that a high vacuum condition is advantageous in achieving accurate thickness upon deposition. Preferably, the vacuum may be of at least about $1 \times 10^{-5}$ Torr or less.

In an embodiment where the solar cell includes an anti-reflection layer such as the anti-reflection layer 120, the anti-reflection layer may be deposited onto the TCL by thermal evaporation.

Hereinafter, the present invention is described more specifically by way of examples, but the present invention is not limited thereto.

EXAMPLES

Materials and Reagents

The reagents and starting materials for the synthesis of 2-sulfonate anthraquinone (AQS) derivatives were commercially available and used without further purification, if not specified. Cesium iodide (CsI), formamidinium iodide (FAI), and formamidinium bromide (FABr) were purchased from Dysol (Australia). Lead iodide ($PbI_2$, purity of 99.999%), lead bromide ($PbBr_2$, purity of 99.9%), and 1-chloronaphthalene (1-CN) were purchased from TCI (Japan). Lead chloride ($PbCl_2$), methylammonium chloride (MACl), fullerene (C60), and bathocuproine (BCP, purity of 99.9%) were purchased from Xi'an Polymer Light Technology Corporation (China). N,N-dimethylformamide (DMF, purity of 99.99%), dimethyl sulfoxide (DMSO, purity of 99.50%), isopropanol (IPA, purity of 99.50%), and chlorobenzene (CB, purity of 99.90%) were purchased from J&K (China) and used as received. PM6 and Y6 were purchased from Solarmer Materials. $PC_{71}BM$ was purchased from American Dye Source, Inc. Molybdenum oxide ($MoO_x$), chloroform (CF, purity of 99.90%), and methanol (MeOH, purity of 99.90%) were purchased from Sigma-Aldrich. The gold and silver pellets for thermal evaporation use were purchased from commercial sources with high purity. ((2,7-dimethoxy-9H-carbazol-9-yl) methyl) phosphonic acid (DC-PA, hole-selective self-assembled monolayer) and piperazinium iodide (PI, surface passivating agent for perovskite) were synthesized as reported in our previous studies.

Methods and Characterization

Redox Mediator Experiments in Solution State $I^0$ (25 mg, 0.1 mmol) and $Pb^0$ (25 mg, 0.12 mmol) powder dispersed in 2 mL mixed DMF/IPA solvent (volume ratio 1:10) with or without redox mediators (0.025 mmol), and the solutions were stirred at 100° C. for 60 min. The UV-vis absorption spectra of the upper solution (dilute to $1.0 \times 10^{-5}$ M) and XRD patterns of the bottom precipitation from the sample and reference solutions (after 60 min) were measured. The representative solution and the absorption spectra of the bottom layer in which FAI mixed with mediator dissolved in DMF.

Preparation of Perovskite Precursor

The wide-bandgap perovskite precursor ($Cs_{0.2}FA_{0.8}Pb(I_{0.6}Br_{0.4})_3$) with a concentration of 1.2 M was prepared by dissolving CsI (0.144 M), CsBr (0.096 M), FAI (0.576 M), FABr (0.384 M), $PbI_2$ (0.756 M), and $PbBr_2$ (0.48 M) in 1mL mixed solvent of DMF/DMSO (v/v, 4:1). It should be noted that 3.0 mol % of $MAPbCl_3$ and 0.5 mol % of 4-guanidinobenzoic acid hydrochloride were added to the perovskite precursor upon device fabrication. These two chemicals may act as passivating agents to (in addition to the activity of the redox mediator) further passivate the defects in the perovskite layer as discussed herein. Advantageously, it is appreciated that these passivating agents may be distributed at the grain boundaries of the perovskite layer without disturbing the chemical composition of the perovskite layer. For the target devices (solar cells containing the redox mediators of as disclosed herein), 0.3 mol % of the redox mediator (i.e., AQSH, AQSN, or AQSP) was added to the perovskite precursor. The above solutions were stirred overnight at room temperature, and no filtration was required before use.

Fabrication of Single-Junction Wide-Bandgap Perovskite Solar Cells (PSCs)

The pre-patterned indium-doped tin oxide (ITO) glass substrates were sequentially cleaned by sonication with detergent (Decon 90/deionized water with 1:1/v:v), deionized water, acetone, and isopropanol (IPA) for 15 min, respectively. Then, the cleaned ITO glass substrates were transferred into an oven at 100° C. for 24 hours and treated with $O_2$ plasma for 10 min before use. The DC-PA hole-selective SAM (0.75 mg $mL^{-1}$ in IPA) was spin-coated onto ITO glass substrates at 3,000 r.p.m. (with a ramping rate of 2,000 r.p.m. $s^{-1}$) for 25 s, and were subsequently annealed at 110° C. for 15 min. After cooling, the substrates were rinsed with IPA solvent and annealed for another 5 min at 100° C. The perovskite film was then deposited on the DC-PA layer by a one-step spin-coating method. Specifically, 50 μL of the perovskite precursor as described above (with or without the redox mediators) was spin-coated at 4,000-6,500 r.p.m. (with a ramping rate of 1,500 r.p.m. $s^{-1}$) for 30 s. During the spin-coating process, 200 μL of chlorobenzene (CB) anti-solvent was quickly dripped onto the center of perovskite film 10 s before the end of the process and then annealed at 100° C. for 15 min. Next, piperazinium iodide (PI) (0.3 mg $mL^{-1}$ in IPA) was dynamically spin-coated onto the as-formed perovskite at 5,000 r.p.m. for 30 s, followed by annealing at 100° C. for 10 min. All the above spin-coating processes were conducted in an $N_2$-filled glovebox with the contents of $O_2$ and $H_2O$<5 ppm at a controlled temperature of −20° C. Finally, 20 nm C60, 6 nm BCP, and 100 nm Ag were thermally evaporated in a high vacuum chamber (<2×10$^{-6}$ Torr) through a metal shadow mask (aperture area: 0.0644 cm$^2$), respectively. 100 nm of MgF$_2$ was thermally evaporated onto the glass side of the devices as an anti-reflection (AR) layer.

Preparation of Organic Bulk Heterojunction (BHJ) Layer Precursor

PM6, Y6 and PC$_{71}$BM with a weight ratio of 1:0.96:0.24 were dissolved in chloroform (CF), while the concentration of PM6 was fixed at 7 mg mL$^{-1}$. The solvent additive (0.5 vol %), i.e., 1-CN, was added to the above solution. Then, the solution was stirred at 40° C. for 2 hours before use.

Fabrication of Single-Junction Narrow-Bandgap Organic Solar Cells (OSCs)

The OSCs with p-i-n configuration were based on the device structure of glass/ITO/MoO$_x$/PM6:Y6:PC$_{71}$BM/PN-DIT-F3N/Ag. First, 10 nm MoO$_x$ was thermally evaporated (with a rate of 0.05 Å s$^{-1}$) on clean ITO substrates in a high vacuum chamber (<6×10$^{-7}$ Torr). Then, PM6:Y6:PC$_{71}$BM solution was dynamically cast onto MoO$_x$ layer at 1,500 r.p.m for 40 s, followed by thermal annealing at 90° C. for 10 min. After cooling, PNDIT-F3N (0.5 mg mL$^{-1}$ in methanol with 0.5 vol % of acetic acid) interfacial layer was dynamically spin-coated on the organic BHJ layer at 1,500 r.p.m. for 40 s. Finally, 100 nm Ag was thermally evaporated in a high vacuum chamber (<2×10$^{-6}$ Torr) through a metal shadow mask (aperture area: 0.0644 cm$^2$).

Fabrication of Perovskite-Organic Tandem Solar Cells (PO-TSCs)

For the monolithic (two-terminal) PO-TSCs in this work, the narrow-bandgap organic subcells were integrated on top of the perovskite sub-cells. Briefly, after the thermal evaporation of BCP in wide-bandgap sub-cells, 0.5 nm Au (with a rate of 0.05 Å s$^{-1}$) and 10 nm MoO$_x$ were thermally evaporated on top of BCP, respectively, to form an ICL structure for the tandem cells. Then, the organic BHJ layer and interfacial layer (i.e., ICL) were sequentially spin-coated on MoO$_x$. PNDIT-F3N was dynamically spin-coated on the organic BHJ layer at 1,500 r.p.m. for 40 s. Finally, 100 nm Ag was thermally evaporated through a metal shadow mask (aperture area: 0.0644 cm$^2$).

Methods and Characterizations $^1$H NMR and $^{13}$C NMR spectra were measured on Bruker AVANCE III 300 MHz and 400 MHz spectrometers. Solution UV-Vis absorption spectra were obtained from Agient8454 spectrophotometer. Cyclic voltammetry (CV) measurements were conducted on a CHI660D electrochemical workstation. The CV experiments were performed at room temperature with a conventional three-electrode system using a glassy carbon electrode as the working electrode, Pt wire as the counter electrode, and Ag/AgCl (saturated KCl) as the reference electrode. Ammonium chloride (NH$_4$Cl, 0.1M) in an aqueous solution was used as the supporting electrolyte, and the scan rate was 0.1 V s$^{-1}$. Elemental analyses were obtained by Elemantar: Vario UNI-CUBE. Transmittance and absorption spectra were conducted on an ultraviolet-visible (UV-vis) spectrometer (PE Lamda 750).

Time-dependent photoluminescence (tdPL) spectra were collected by a home-built facility, where an excitation laser (450 nm) was introduced to the sample through a fiber, and the PL spectra were detected by using a detector connected with an Ocean Optics USB2000. X-ray photoelectron spectroscopy (XPS) was performed on Thermo Fisher ESCALAB XI+ X-ray Photoelectron Spectrometer. The non-monochromatic He I is employed as UV light with an energy of 21.21 eV.

The top-viewing morphology of the thin film samples, cross-section profile of tandem cell, and the cross-sectional energy dispersive spectroscopy (EDX, line scan) were conducted by scanning electron microscopy (SEM, QUATTRO S). Powder and thin film X-ray diffraction (XRD) characterizations were conducted on D2 Phaser instrument with a Cu Kα (a wavelength of 1.5418 Å) radiation.

Time-resolved photoluminescence spectrum (trPL) was recorded by FLS980 spectrofluorometer (Edinburgh) with a 480 nm pulsed excitation laser. The current density-voltage (J-V) characteristics of the devices were measured in an N$_2$-filled glovebox at room temperature using a Keithley 2400 SourceMeter under simulated sunlight from a solar simulator (EnliTech, SS-F5, Taiwan). A National Renewable Energy Laboratory (NREL) calibrated silicon solar cell (with a KG-2 filter) was used to obtain AM 1.5G (100 mW cm$^{-32}$) solar simulator's light intensity. The perovskite solar cells were covered with a shading mask with an aperture area of 0.0419 cm$^2$ to ensure the accuracy of current density from J-V curves.

The J-V measurements were conducted with sweep mode with reverse and forward scans with a scan rate of 10 mV s$^{-1}$ and a step of 0.02 V. The EQE curves were carried out by an EQE measurement system (EnliTech, QE-R, Taiwan). For perovskite-organic tandem solar cells, the EQE of wide-E$_g$ perovskite subcells was measured while saturating the corresponding organic subcells by applying a bias illumination with an 800 nm long-pass optical filter. Likewise, the EQE of narrow-E$_g$ organic subcells was measured while saturating the corresponding perovskite subcells by applying a bias illumination with a 500 nm short-pass optical filter. No bias voltage was applied during all EQE measurements.

Long-Term Device Stability Measurement

The long-term device stability of the encapsulated devices was tested by an in-situ stability measurement system (CRY-SCO) equipped with multiple sample chambers (without UV filter and temperature control) and automatic data collecting elements. The solar cells were tracked at their maximum power point (MPP) under a simulated AM 1.5G spectrum (with 1-sun equivalent intensity). The light source is a SLED lamp with the wavelength range from 400 to 1,000 nm. A silicon photoelectric probe was equipped to monitor the change in the light intensity and adjust the intensity automatically with the control of the host. The sample chamber was placed in the air with a continuous N$_2$ flow during the test.

Density Functional Theory (DFT) Calculations

The DFT calculations were carried out using the projector-augmented wave (PAW) method as implemented in the Vienna Ab initio Simulation Package (VASP) code. The generalized gradient approximation (GGA) together with the Perdew-Burke-Ernzerhof (PBE) exchange-correlation functional was applied. The van der Waals (vdW) interactions were also included in the calculations using the zero damping DFT-D3 method of Grimme. A uniform grid of 6×6×6 k-mesh in the Brillouin zone was employed to optimize the crystal structures of cubic-phase $FAPbI_3$ in bulk, 4×4×1 k-mesh for $FAPbI_3$ slabs, and 2×2×1 k-mesh for molecule/$FAPbI_3$ interfaces. The energy cutoffs of the wavefunctions were set at 500 eV for the bulk and 450 eV for the slabs and interfaces. The unit cells had a (2×2) lateral periodicity and contained four or five octahedral layers of $FAPbI_3$ with exposed (100) and (110) surfaces with different terminations (FAI-rich and $PbI_2$-rich) and surface defects ($V_{FA}$ and $V_{Pb}$). The slab replicas were separated by ~20 Å of vacuum. Each structure was optimized until forces on single atoms were smaller than 0.015 eV $A^1$. The energy barriers for the half-reactions related to the elimination of $Pb^0$ and $I^0$ were calculated as E ($Pb^0$ elimination)=E ($AQS^{2-}+Pb^{2+}$)−E (AQS)+E ($Pb^0$) and E ($I^0$ elimination)=E ($AQS^-+I^-$)−E ($AQS^{2-}$)+E ($I^0$). The binding energy was calculated as E (binding)=E (interface)−E ($FAPbI_3$)−E (molecule), where E (interface) is the total energy of $FAPbI_3$ upon molecular adsorption, and E ($FAPbI_3$) and E (molecule) are the energies of isolated $FAPbI_3$ and $PEA^+$ [$H^+$ or $NH_4^+$].

Example 1A

Synthesis of AQSH

Figure 2A:
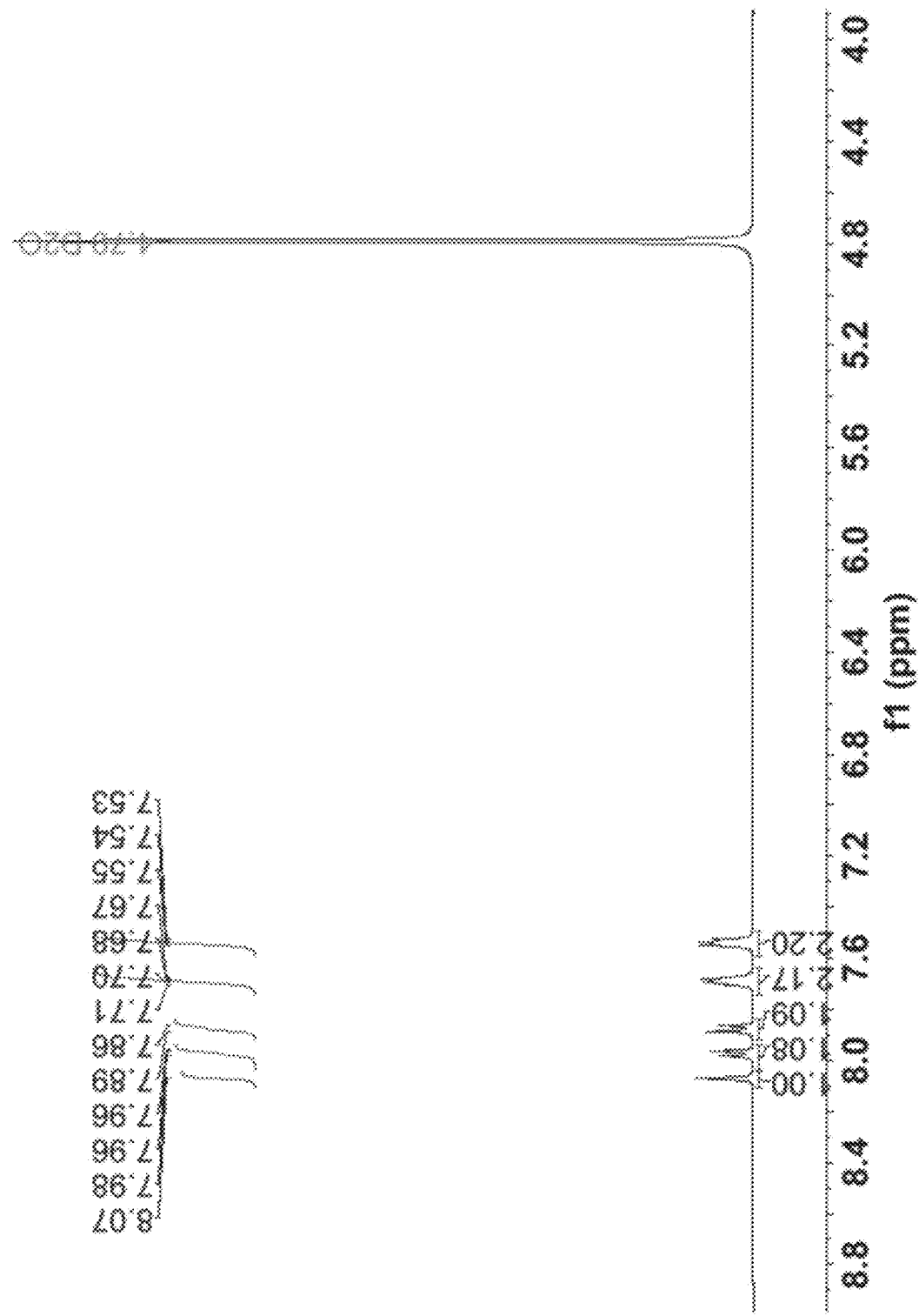
FIG. 2A is a $^1H$ NMR spectrum of the as-synthesized AQSH (Compound of Formula (VIIIa)
Figure 2B:
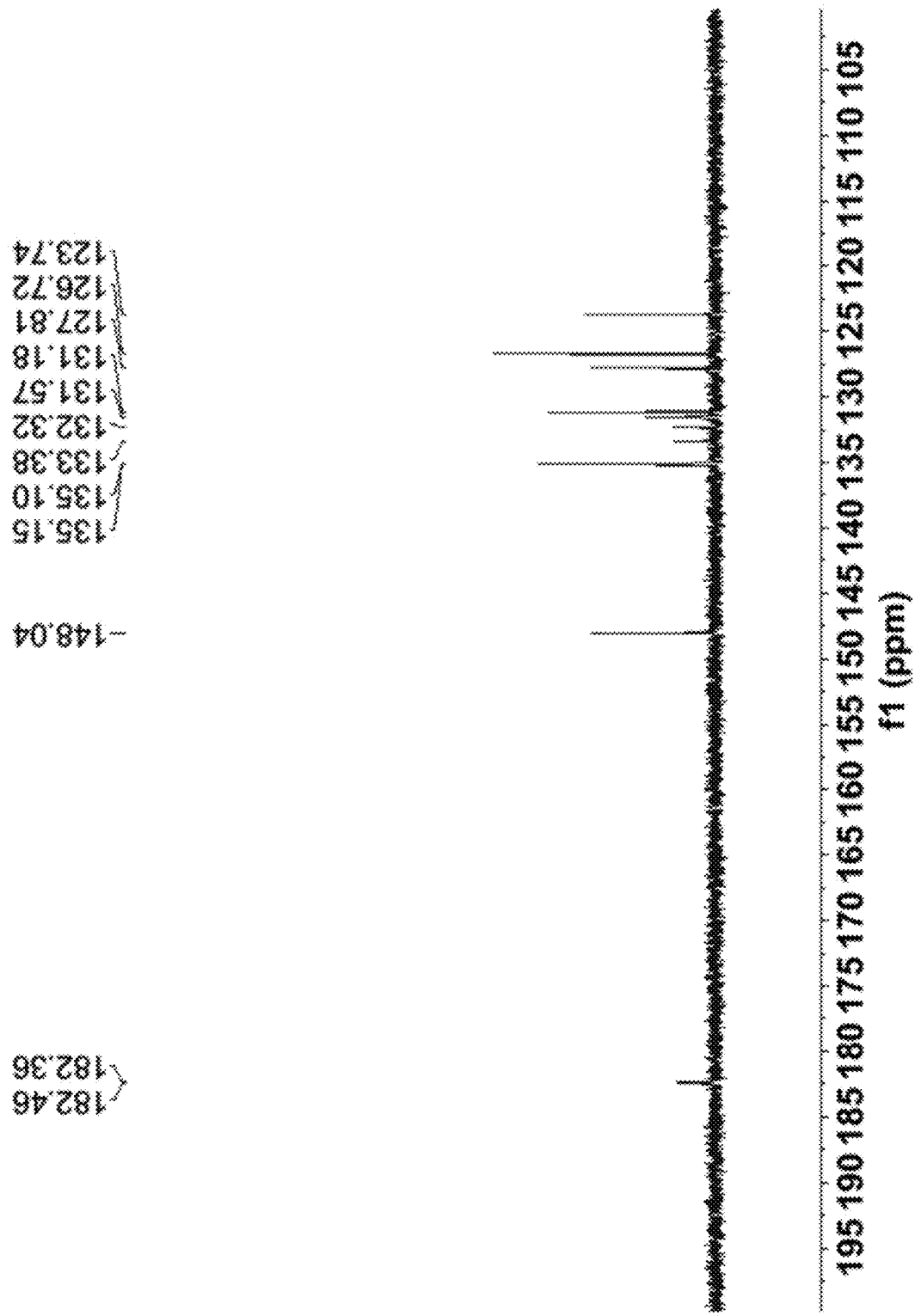
FIG. 2B is a $^{13}C$ NMR spectrum of the as-synthesized AQSH (Compound of Formula (VIIIa)

Sodium anthraquinone-2-sulfonate (300 mg, 0.97 mmol) and 3 mL Amberlite cation exchange resin (IR-120 hydrogen form) were added to 5 mL deionized water. The mixture was stirred overnight when the anthraquinone compound was dissolved. Then the solution was flushed over a cation exchange column with Amberlite cation exchange resin again. The obtained sulfonic acid was evaporated, and the compound was dried under a vacuum overnight. The product was obtained as pale-yellow powder with a yield of 216 mg (yield: 77%). $^1$H NMR (400 MHz, $D_2O$) δ 8.07 (s, 1H), 7.97 (d, J=8.2 Hz, 1H), 7.88 (d, J=8.2 Hz, 1H), 7.74-7.64 (m, 2H), 7.58-7.50 (m, 2H) (FIG. 2A). $^{13}$C NMR (101 MHz, $D_2O$) δ 182.46, 182.36, 148.04, 135.15, 135.10, 133.38, 132.32, 131.57, 131.18, 127.81, 126.72, 123.74. (two peaks overlap) (FIG. 2B).

Example 1B

Synthesis of AQSN

Figure 3A:
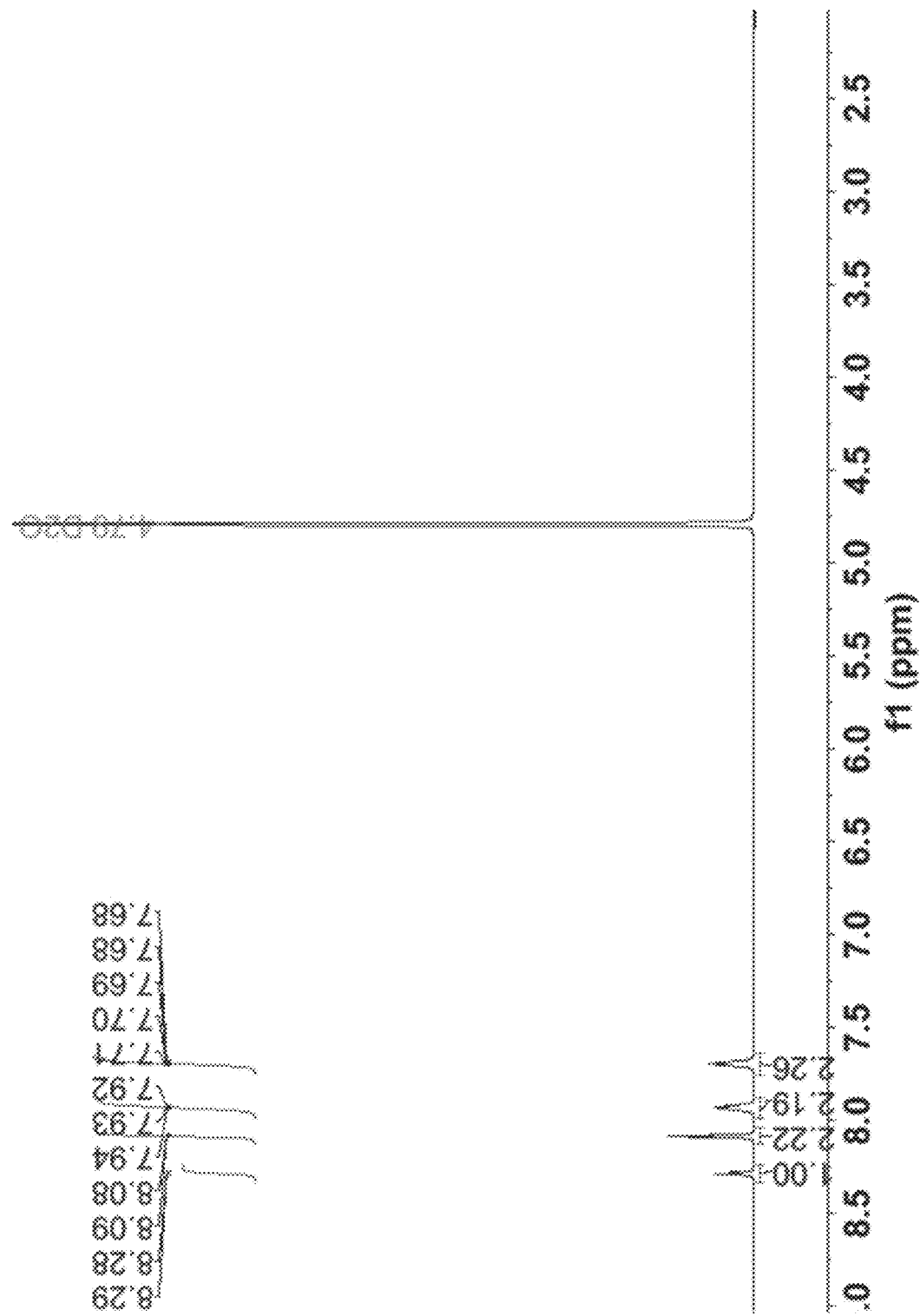
FIG. 3A is a $^1H$ NMR spectrum of the as-synthesized AQSN (Compound of Formula (VIIIb)
Figure 3B:
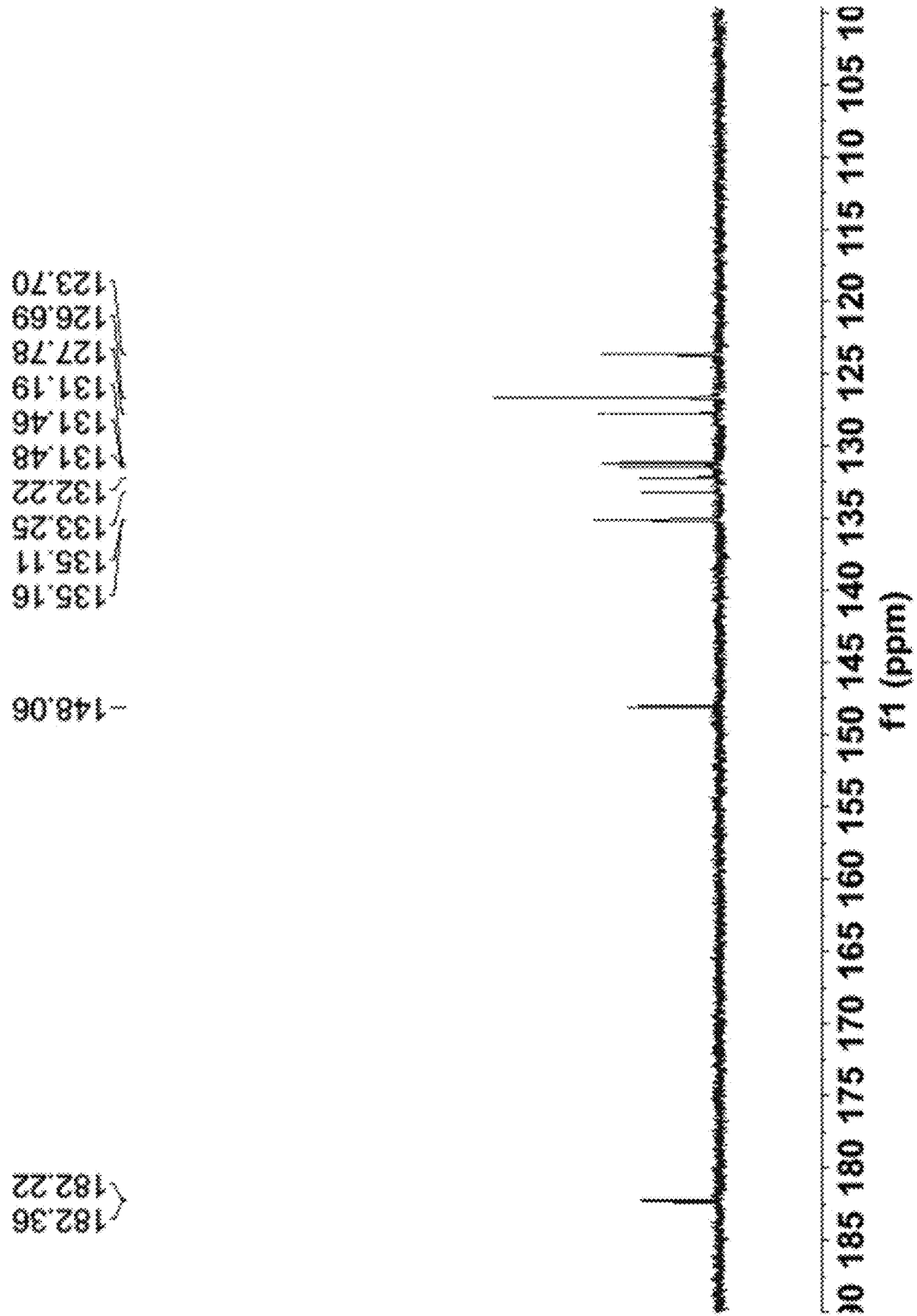
FIG. 3B is a $^{13}C$ NMR spectrum of the as-synthesized AQSN (Compound of Formula (VIIIb)

An aqueous solution of AQSH (0.97 mmol) obtained as mentioned in Example 1A was cooled to 0° C., and then 0.5 mL 30% ammonium hydroxide was added to convert the acid to ammonium salt. The water was evaporated and the compound was dried under vacuum overnight. The product was obtained as light-yellow powder with a yield of 278 mg (yield: 94%). $^1$H NMR (400 MHz, $D_2O$) δ 8.28 (s, 1H), 8.14-8.04 (m, 2H), 8.02-7.87 (m, 2H), 7.76-7.61 (m, 2H) (FIG. 3A). $^{13}$C NMR (101 MHz, $D_2O$) δ 182.36, 182.22, 148.06, 135.16, 135.11, 133.25, 132.22, 131.48, 131.46, 131.19, 127.78, 126.69, 123.70. (one peak overlap) (FIG. 3B). Anal. Calcd for $C_{14}H_{11}NO_5S$: C 55.08%, H 3.63%, N 4.59%, S 10.50%; found: C 54.52%, H 3.63%, N 4.57%, S 10.94%.

Example 1C

Synthesis of AQSP

Figure 4A:
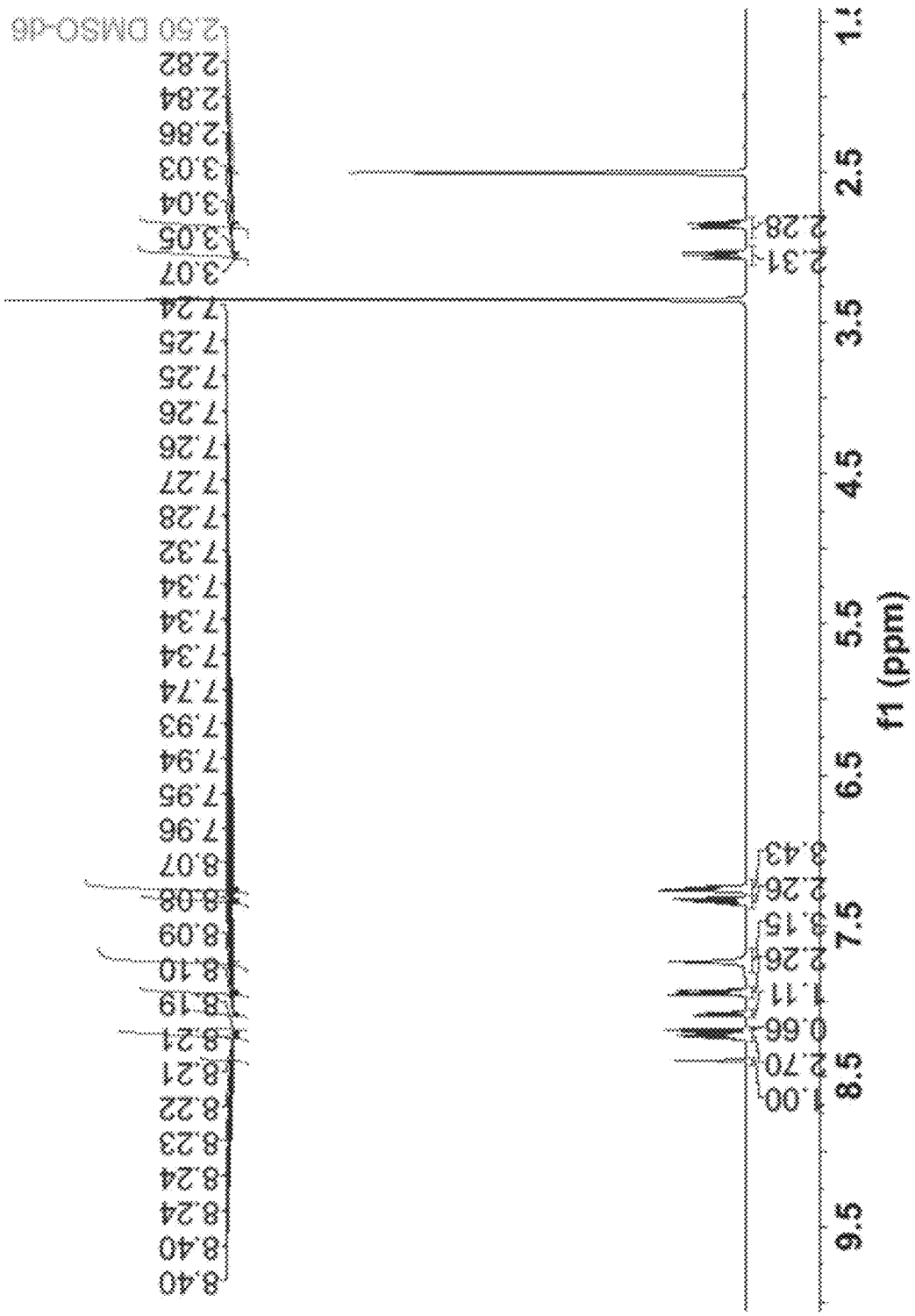
FIG. 4A is a $^1H$ NMR spectrum of the as-synthesized AQSP (Compound of Formula (VIIIc)
Figure 4B:
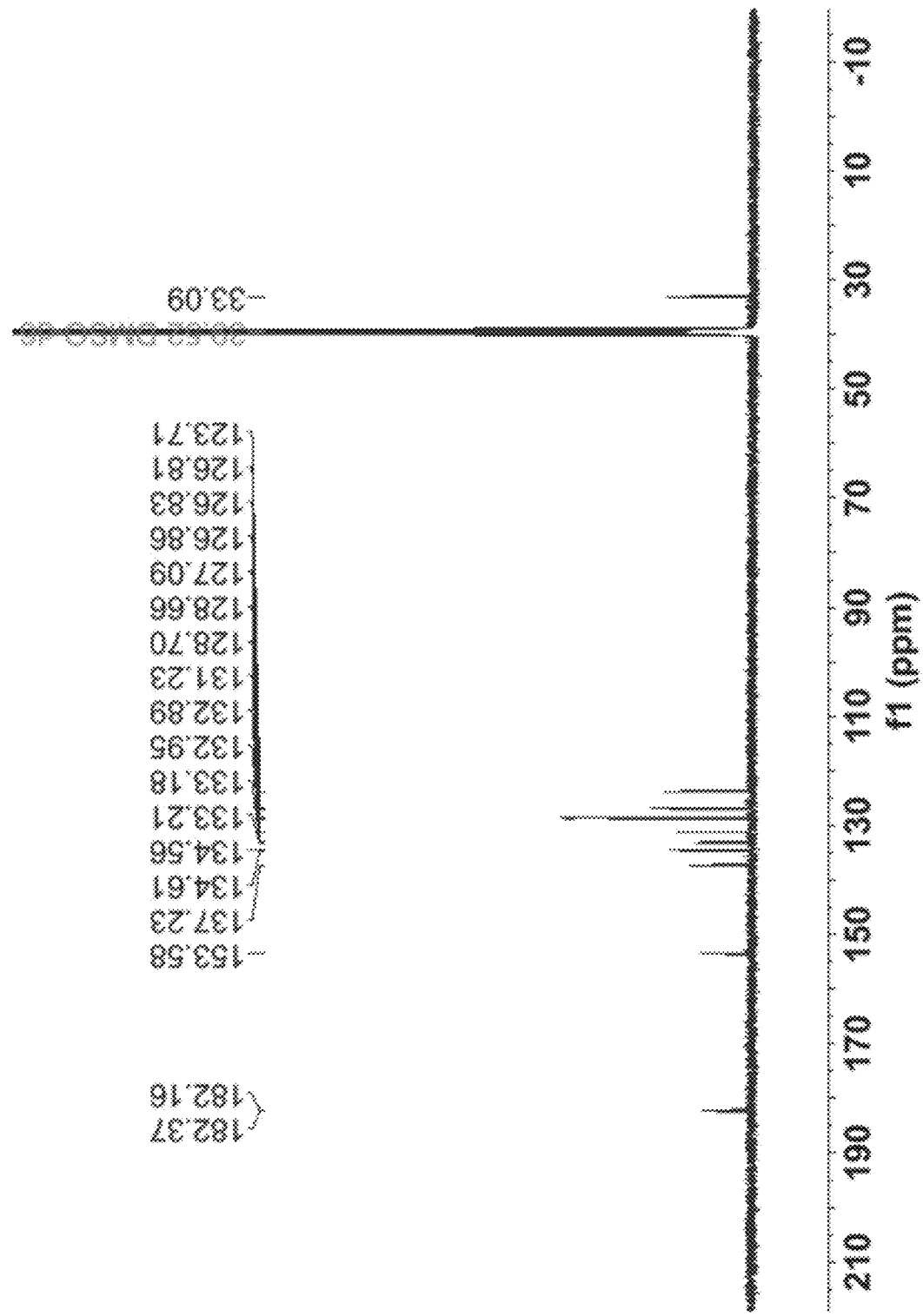
FIG. 4B is a $^{13}C$ NMR spectrum of the as-synthesized AQSP (Compound of Formula (VIIIc)

An aqueous solution of AQSH (0.97 mmol) obtained as mentioned in Example 1A above was cooled to 0° C. and then 1.2 equiv. phenethylamine was added to convert the acid to ammonium salt. The water was evaporated and the compound was dried under vacuum overnight. The product was obtained as light-yellow powder with a yield of 311 mg (yield: 76%). $^1$H NMR (400 MHz, DMSO-$d_6$) δ 8.40 (d, J=1.7 Hz, 1H), 8.29-8.16 (m, 3H), 8.09 (dd, J=8.1, 1.7 Hz, 1H), 7.94 (dq, J=7.3, 4.0 Hz, 2H), 7.75 (s, 3H), 7.40-7.29 (m, 2H), 7.29-7.19 (m, 3H), 3.04 (t, J=9.6 Hz, 2H), 2.84 (t, J=9.6 Hz, 2H) (FIG. 4A). $^{13}$C NMR (101 MHz, DMSO-$d_6$) δ 182.37, 182.16, 153.58, 137.23, 134.61, 134.56, 133.21, 133.18, 132.95, 132.89, 131.23, 128.70, 128.66, 127.09, 126.86, 126.83, 126.82, 123.72, 33.09. (one peak overlap) (FIG. 4B). Anal. Calcd for $C_{22}H_{19}NO_5S$: C 64.53%, H 4.68%, N 3.42%, S 7.83%; found: C 64.60%, H 4.68%, N 3.29%, S 8.18%.

Example 2

Synthesis of AQSester

Sodium anthraquinone-2-sulfonate (2.5 g, 8 mmol) was first converted to the corresponding sulfonyl chloride by reacting with thionyl chloride (10 mL, 137 mmol) and DMF (0.5 mL). The reaction mixture was poured into ice water. The precipitate was filtered and dried under vacuum to yield a yellow solid (2.4 g, 98%). To a mixture of sulfonyl chloride (1 mmol) and methanol (1 mmol) in DMF (3 mL) was added pyridine (0.06 mL) and the mixture was stirred at 50-60° C. for 2 h. The solution was cooled to room temperature and poured into water (20 mL). The resulting precipitate was filtered, washed with water and purified by column chromatography (0.5% MeOH in DCM) to yield a pale yellow solid with 195 mg (yield: 65%).

Example 3

Synthesis of AQamide

Butylamine (0.16 mL, 1.6 mmol) was added dropwise to a solution of sulfonyl chloride (100 mg, 0.33 mmol) in DCM (5 mL) at 0° C. The reaction mixture was allowed to warm to room temperature and stirred for 2 h. The reaction mixture was washed with water and purified by column chromatography (0.5% MeOH in DCM) to yield a pale yellow solid of 105 mg (yield: 92%).

Example 4

Design and Characterization

Figure 5:
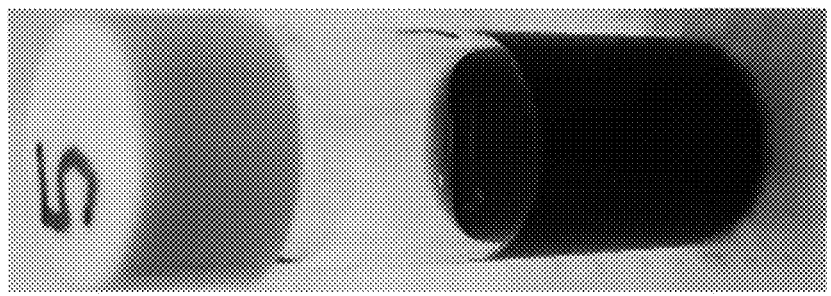
FIG. 5 is a photograph showing $I^0$ and $Pb^0$ powder dispersed in DMF/IPA mixed solvent (volume ratio 1:10) with anthraquinone (after stirring at 100° C. for 60 min)
Figure 6B:
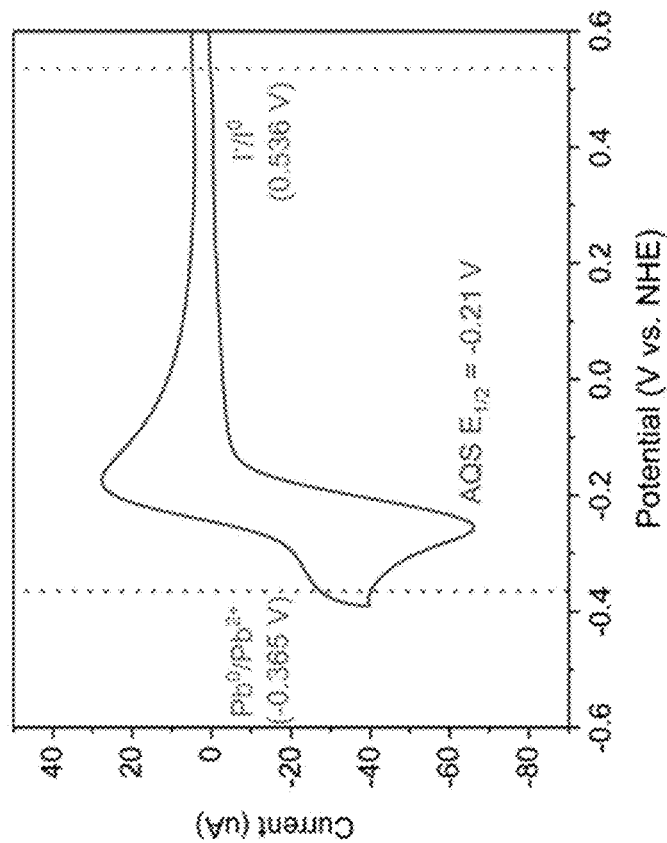
FIG. 6B shows the cyclic voltammetry curve of AQSH.
Figure 6A:
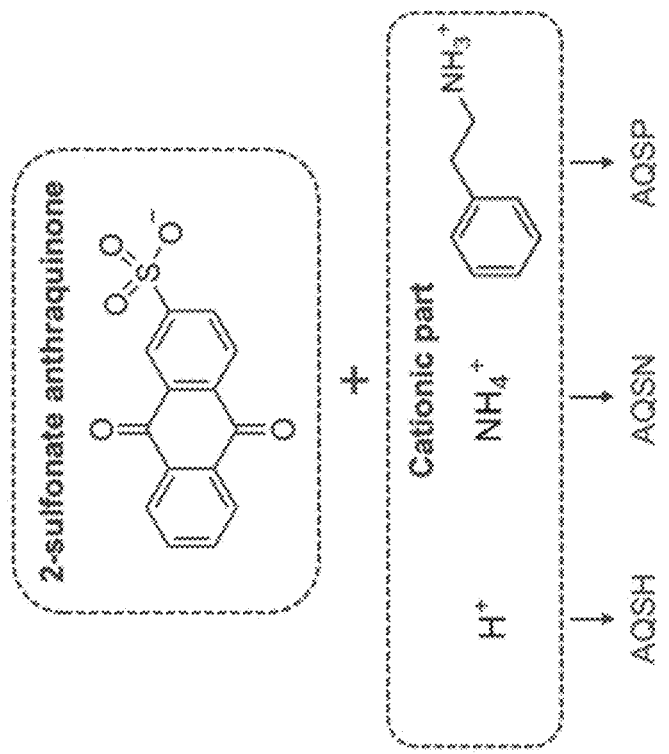
FIG. 6A is a schematic diagram illustrating the molecular structure of the organic redox mediators based on AQS core with different cationic substituents.
Figure 7:
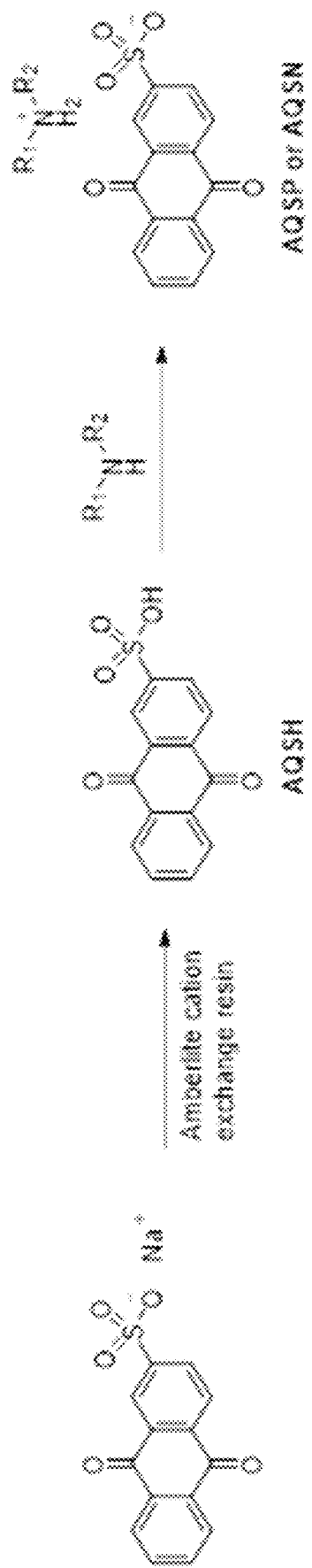
FIG. 7 is a schematic diagram illustrating the synthetic route of AQSH, AQSP, and AQSN.

While it is believed that anthraquinone (AQ) may be used as an redox scaffold, the inventors through their own researches and experiments revealed that AQ in fact could not facilitate the formation of $PbI_2$ through electron shuttling between $Pb^0$ and $I^0$, which may be attributed to its relatively low redox potential compared to Pb, rendering its incapability in oxidizing metallic $Pb^0$ (FIG. 5). To resolve this, the inventors devised that the AQ scaffold may be functionalized with a strong electron-withdrawing —$SO_3^-$ group to tailor its redox potential to reach −0.21 V vs. NHE, enabling suitable redox shuttling between Pb (−0.365 V vs. NHE) and $I_2$ (0.536 V vs. NHE). This modification also increased its solubility in polar organic solvents (i.e., DMF and DMSO) for better processability and provided additional synthetic tunability for its properties (FIGS. 6A and 6B). Furthermore, it is found that by substitution of —H with —$NH_4$ and —PEA in the cationic part of AQS (FIG. 7), it may impart the molecules with defect passivation capability.

Figure 8:
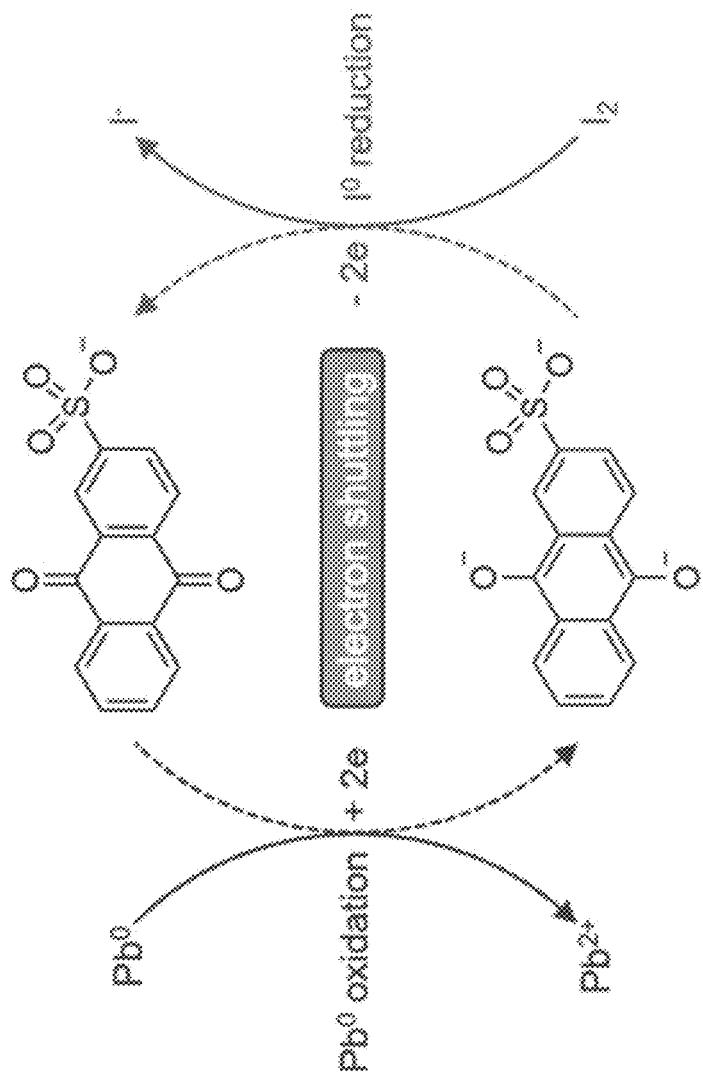
FIG. 8 is a schematic diagram illustrating the electron shuttling between AQS core, Pb, and I.
Figure 9:
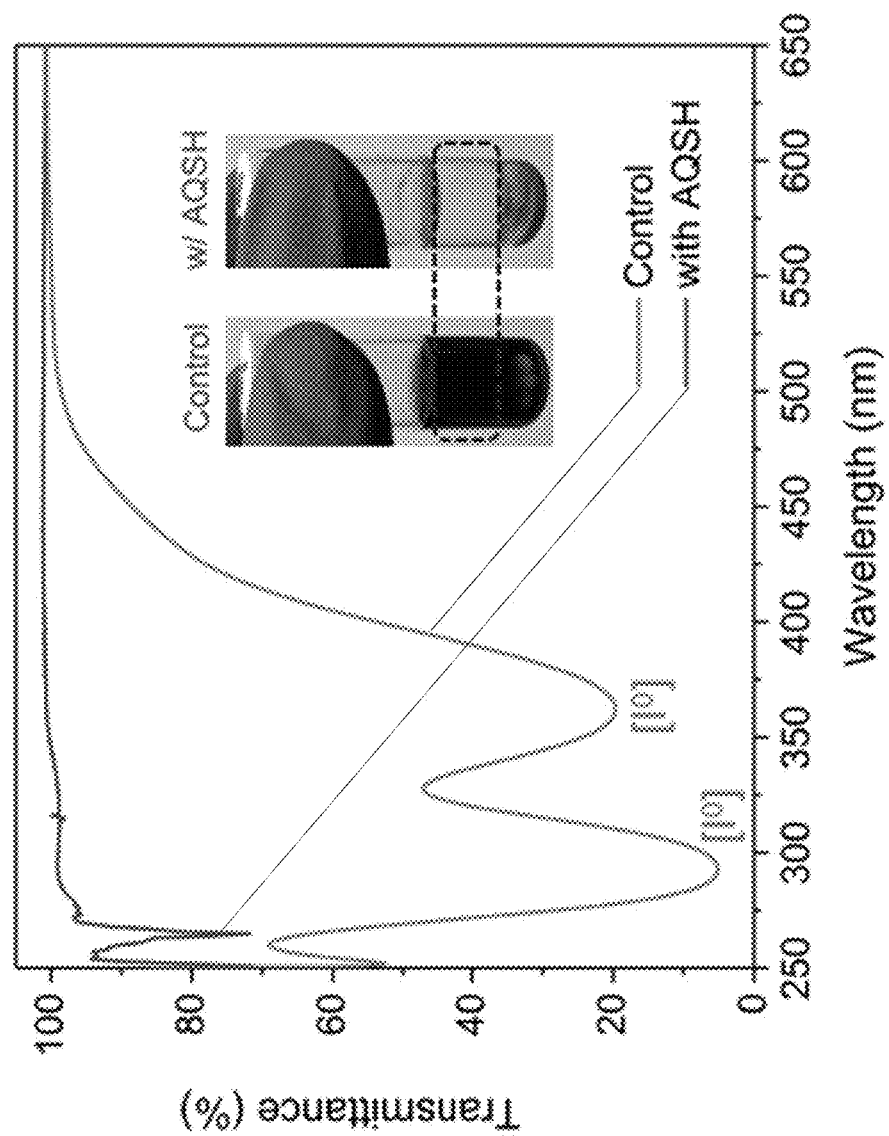
FIG. 9 shows the transmission spectra of $Pb^0$ and $I^0$ powder dispersed in IPA:DMF mixed solvent (v:v=10:1) with and without AQSH.

The proposed redox shuttle is illustrated in FIG. 8, where AQS core governs the redox ability of the molecules. The feasibility of electron transfer between $Pb^0$ and $I^0$ was first examined by dissolving AQSH, $Pb^0$, and $I^0$ powders into a DMF:IPA mixed solvent (with a volume ratio of 1:10) to provide a good trade-off between the solubility of the raw powders and precipitation of as-formed $PbI_2$ (FIG. 9). The control sample (w/o AQSH), shown in the inset of FIG. 9, exhibited minimal yellow solid products and remained deep brown. In contrast, the target sample containing AQSH turned colorless with many yellow precipitates formed, demonstrating efficient conversion of $Pb^0$ and $I^0$ to $PbI_2$ solid through electron shuttling. The transmittance spectra of the supernatant solution (taken from the samples) further confirmed the presence of $I^0$ species only in the control solution, as two characteristic peaks at ~290 nm and ~360 nm were recorded.

Figures 10A, 10B:
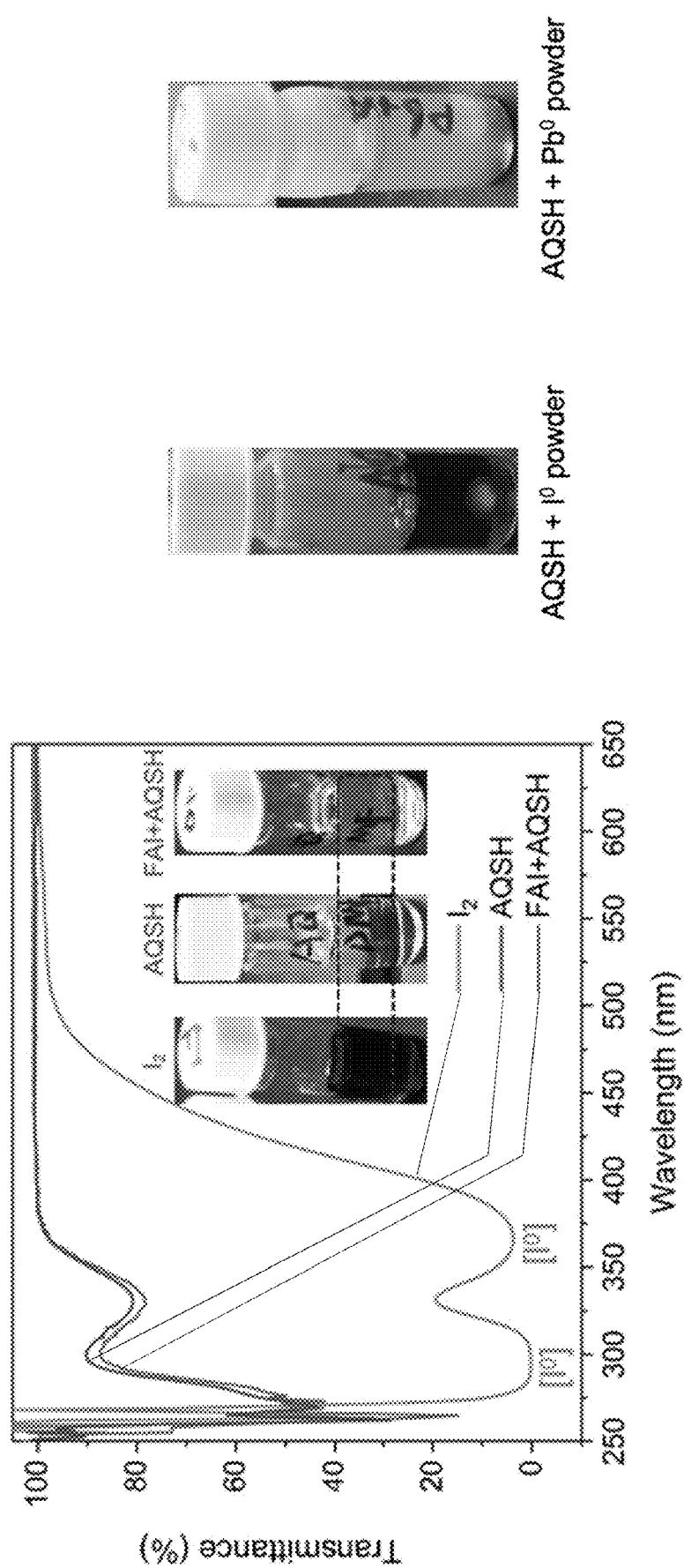
FIG. 10A shows the transmission spectra of $I_2$, FAI, and FAI+AQSH powder dissolved in DMF.
FIG. 10B shows the photographs of the solution consisting of AQSH with $I^0$ powder (left) and AQSH with $Pb^0$ powder (right)
Figure 11:
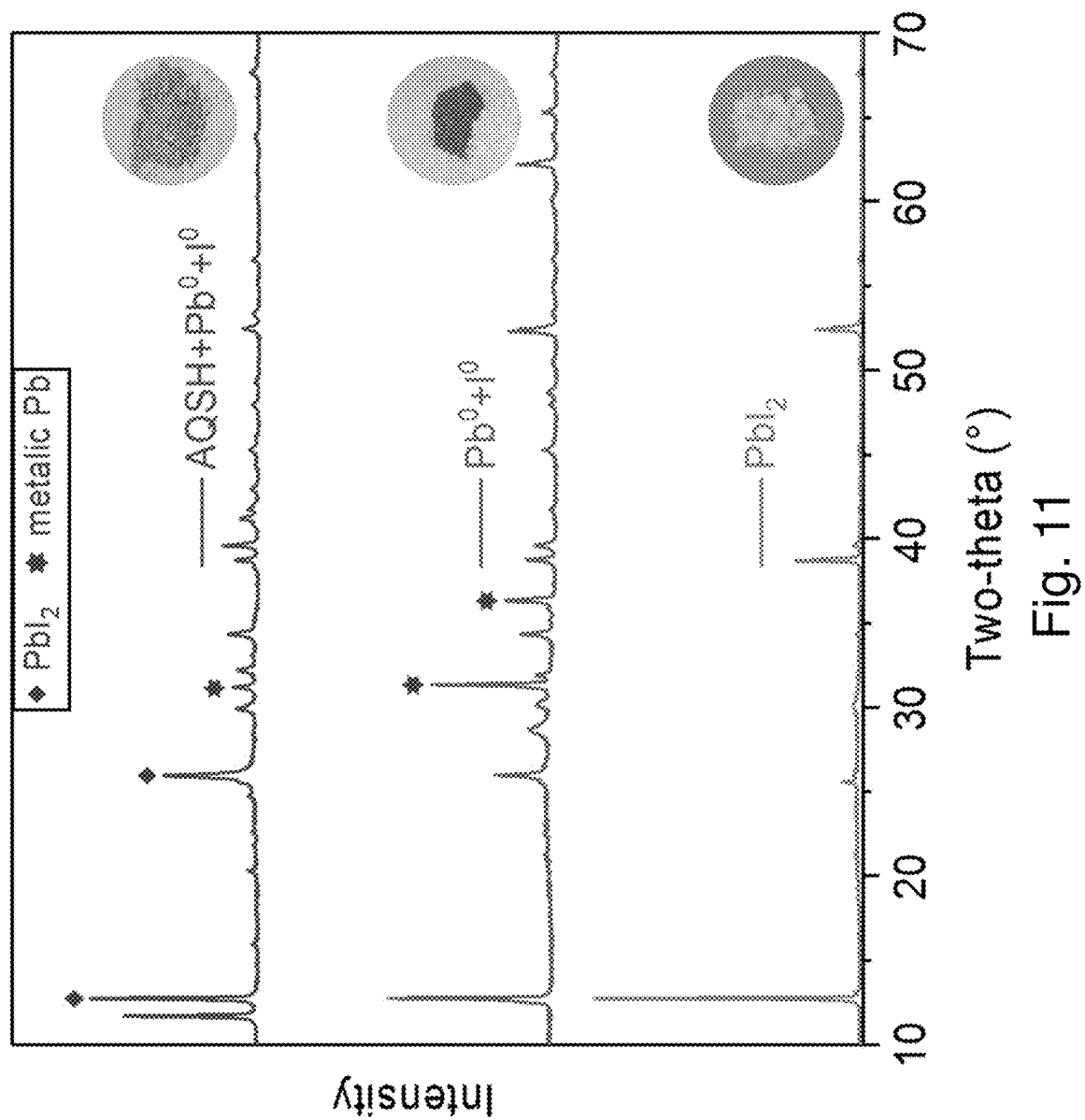
FIG. 11 shows the powder X-ray diffraction (XRD) patterns of $PbI_2$ and the bottom precipitates taken from the glass vial as shown in the inset of FIG. 9.
Figure 12:
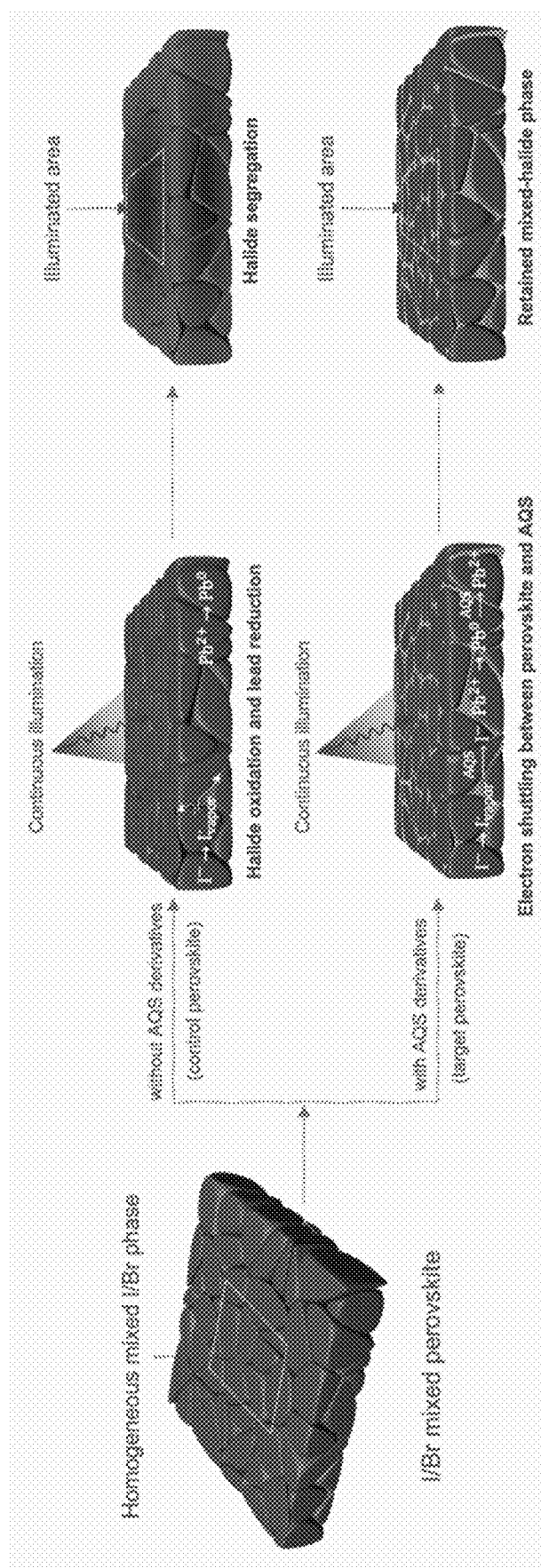
FIG. 12 is a schematic diagram illustrating the proposed mechanism of sustainable elimination of metallic $Pb^0$ and $I^0$ species in perovskite layer with the redox mediator as an additive, and its effect on suppressing halide segregation.

To exclude the possibility of AQSH oxidizing iodides, another set of solutions in DMF consisting of pure $I_2$, pure AQSH, and FAI:AQSH were prepared, respectively (FIG. 10A). The transparent FAI:AQSH solution displayed no peaks from $I^0$ species, implying the selective oxidation of $Pb^0$ instead of $I^-$. The solutions consisted of AQSH with $Pb^0$ or $I^0$ were also tested to further verify this selective redox process (FIG. 10B). By performing powder X-ray diffraction (XRD), the majority of yellow precipitates (the inset in FIG. 9) were verified to be $PbI_2$, based on the presence of the characteristic diffraction peaks at 12.7°, 26.0°, and 38.7° (FIG. 11). Therefore, it is speculated that the AQS derivatives would act as an efficient redox mediator for perovskite, enabling the selective reduction of $I^0$ and oxidation of $Pb^0$. The simultaneous elimination of these defects should help suppress halide segregation in mixed-halide perovskites (as depicted in FIG. 12).

Example 5

Suppression of Halide Segregation in Mixed-Halide Perovskites

Figure 13:
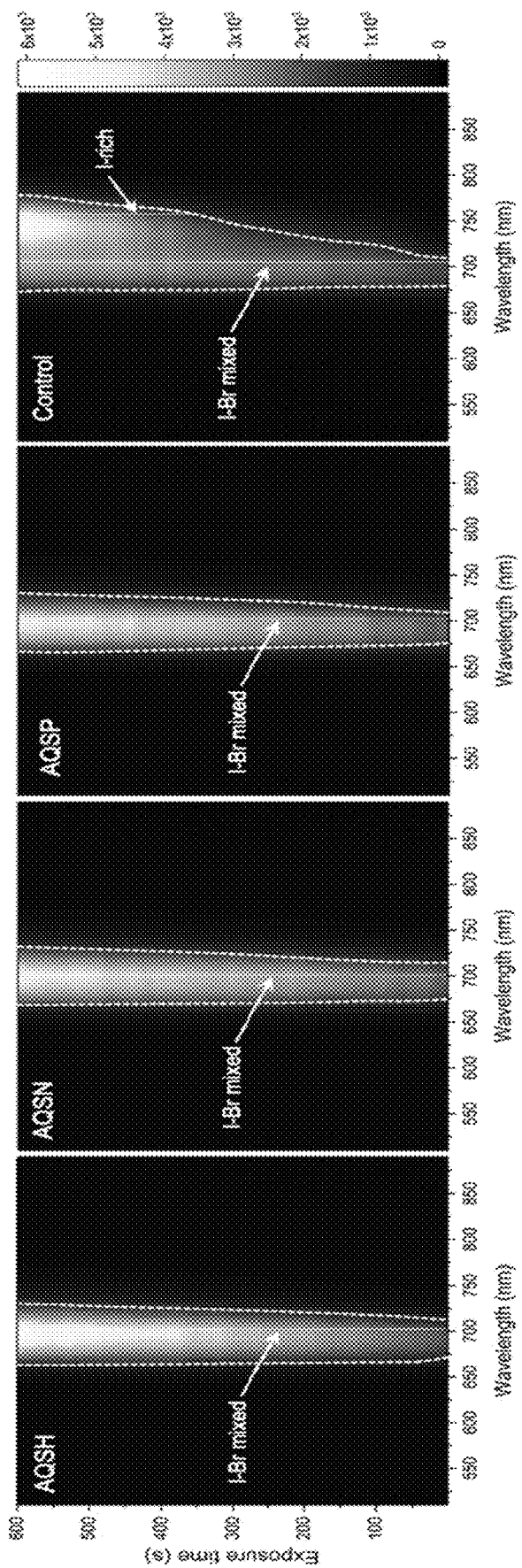
FIG. 13 shows the time-dependent photoluminescence (tdPL) spectra of I/Br mixed perovskite with 0.5 mol % of different AQS derivatives.
Figure 14:
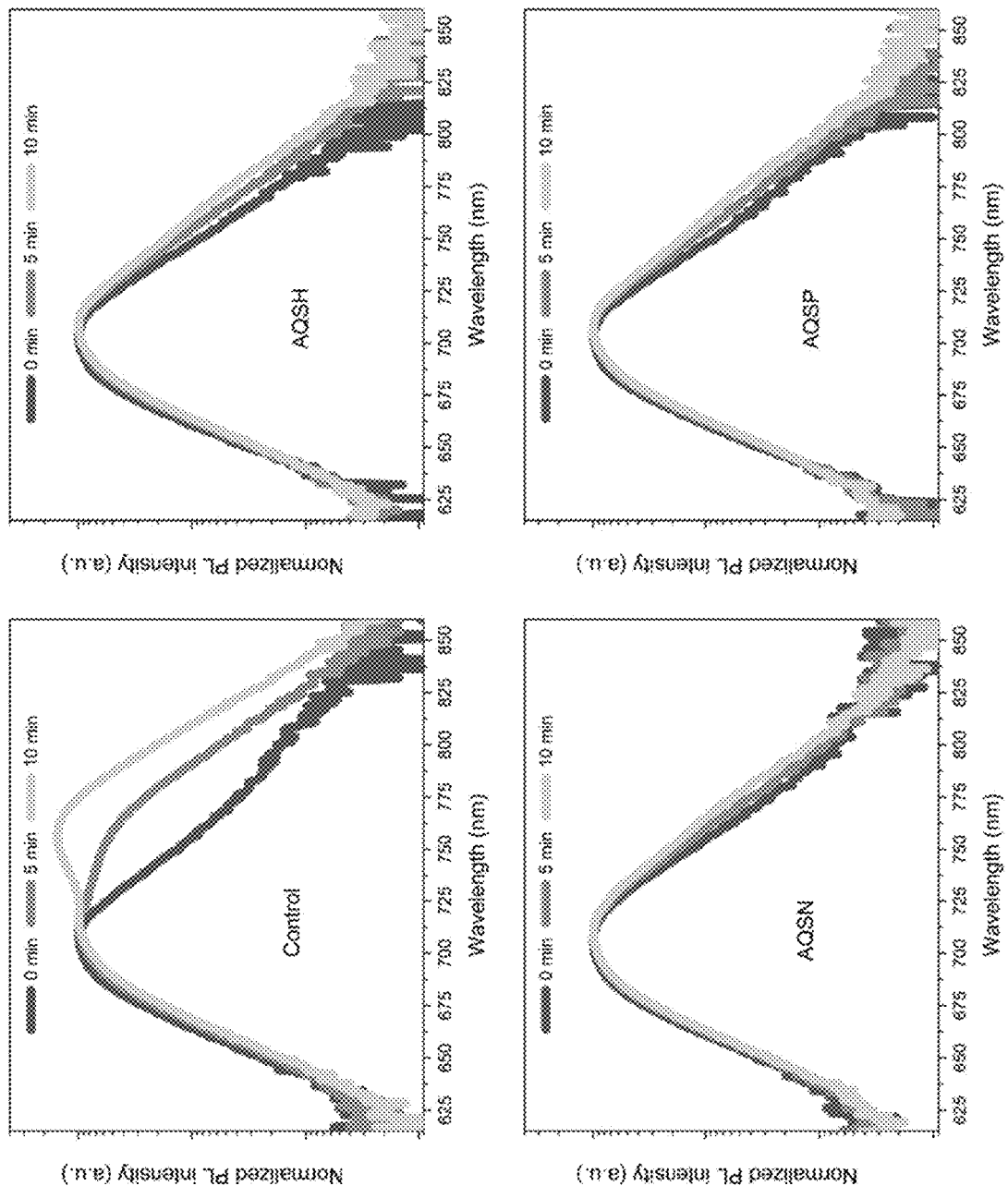
FIG. 14 shows the normalized PL spectra of the I/Br mixed perovskite films with different redox mediators after being illuminated for 0, 5, and 10 min (extracted from the corresponding time-dependent PL spectra in FIG. 13)

The preferential oxidation of the halide with a relatively low oxidation potential ($I^-<Br^-<Cl^-$) is the critical step for halide mass transport, which ultimately triggers phase segregation in perovskites. Therefore, time-dependent PL (tdPL) was first conducted to investigate the effect of AQS-based redox mediators on halide segregation (FIG. 13). The AQS derivatives, namely AQSH, AQSN, and AQSP, were incorporated as additives respectively for I/Br mixed perovskite films. The initial PL peaks at ~700 nm were assigned to the pristine perovskite. After continuous illumination, the PL of the AQS-based perovskite films remained stable, exhibiting only a slight red shift by 3-5 nm (FIG. 14). In contrast, a double-peak shape, which is the sign of halide segregation, gradually appeared in the PL spectrum of the control sample within a few minutes.

Figure 15:
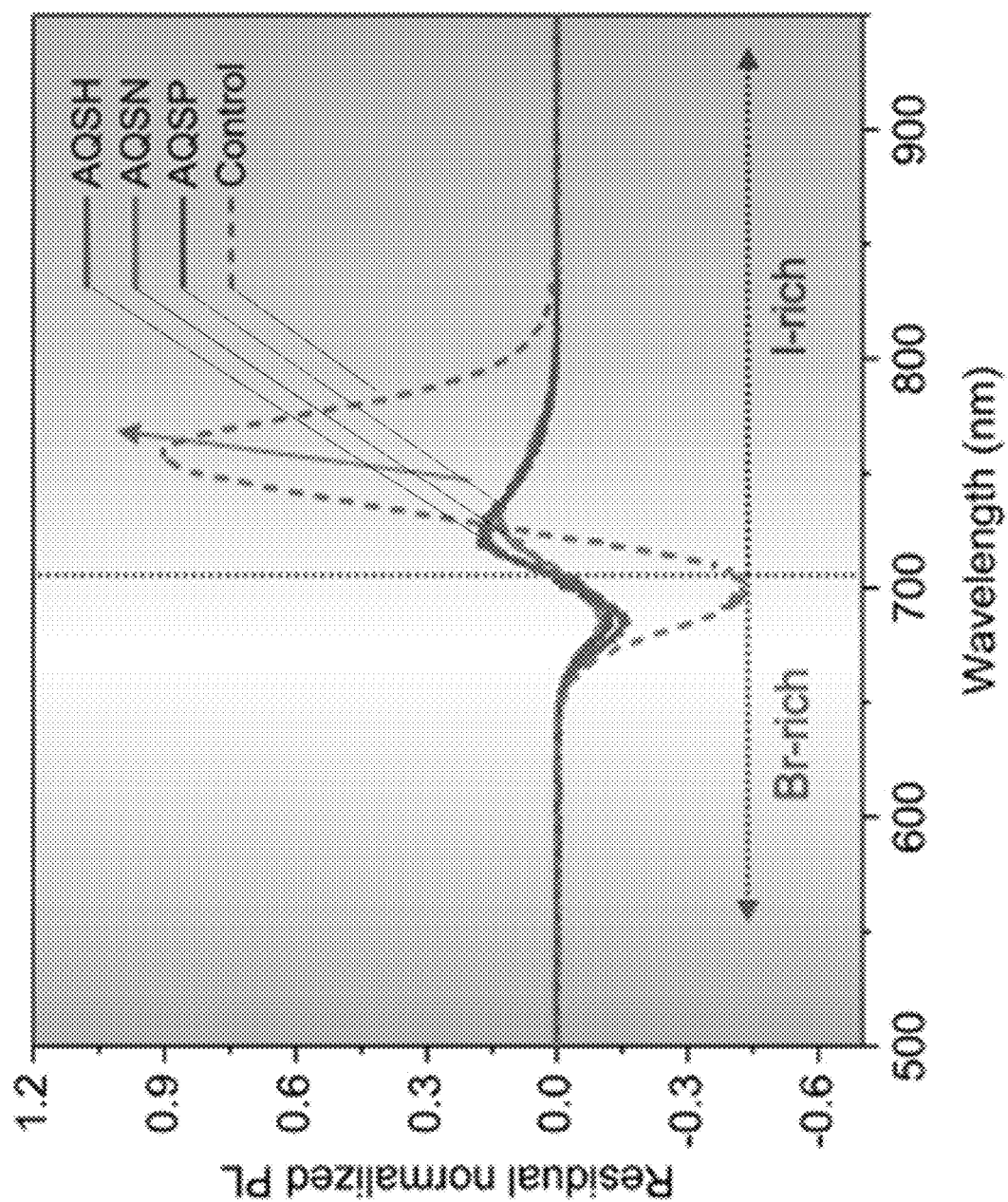
FIG. 15 shows the as-derived PL spectra for analyzing phase stability of I/Br mixed perovskite with 0.5 mol % of different AQS derivatives.
Figure 16:
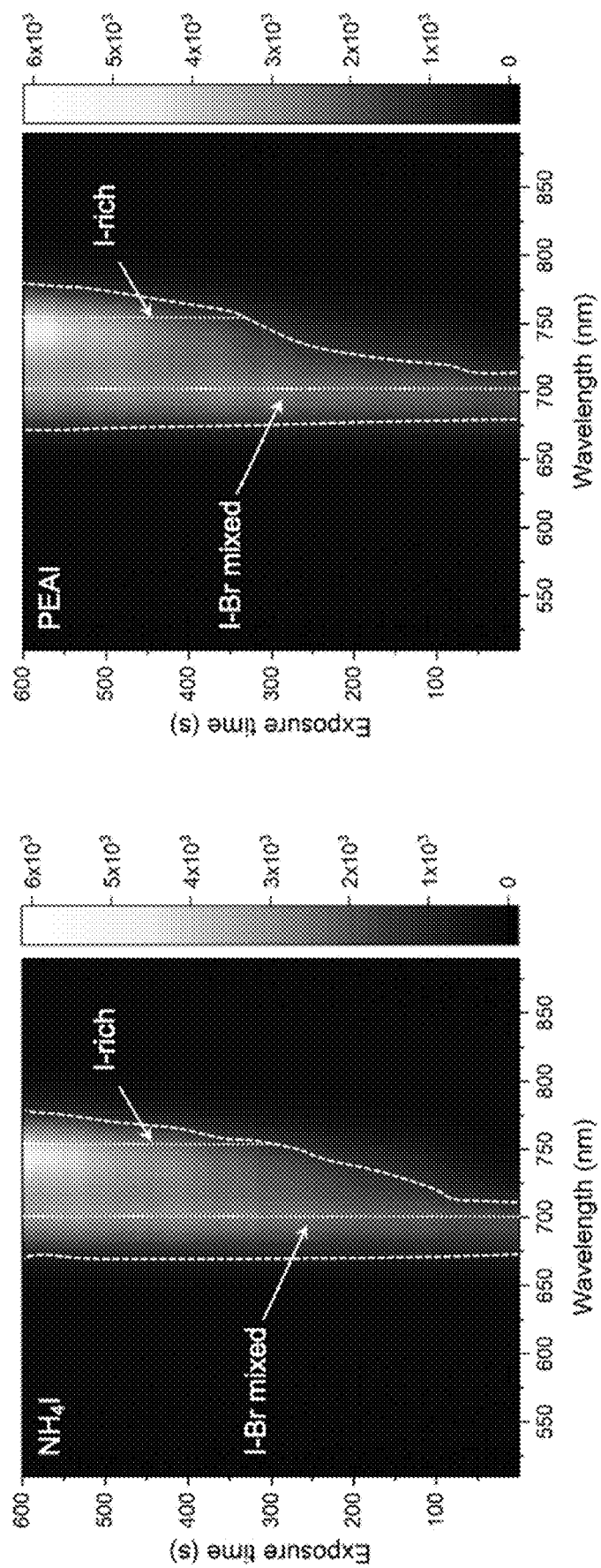
FIG. 16 shows the time-dependent PL spectra of the I/Br mixed perovskite films incorporated with $NH_4I$ or PEAI as additive.

As for segregated I/Br mixed perovskites, the photogenerated charge carriers would funnel into I-rich regions due to their lower bandgaps than the surrounding non-segregated domains. In this case, a new PL peak with lower photon energy (~1.64 eV) was observed in the unstable control perovskite. To intuitively study the extent of halide segregation, residual spectra deduced by subtracting the initial PL from the final spectrum was used, as shown in FIG. 15. The AQS-based perovskites exhibited only a small and symmetric valley-peak shape in their residual PL spectra, while a distinctly larger and asymmetric peak-valley shape was shown in that of the control sample. These significant changes in peak position and shape imply severe halide segregation. In addition, to exclude the effect of cationic substitutions on phase stability, the tdPL measurement for the perovskite films was carried out with $NH_4I$ or PEAI as an additive, which exhibits negligible effect on alleviating phase segregation (FIG. 16).

Figure 17:
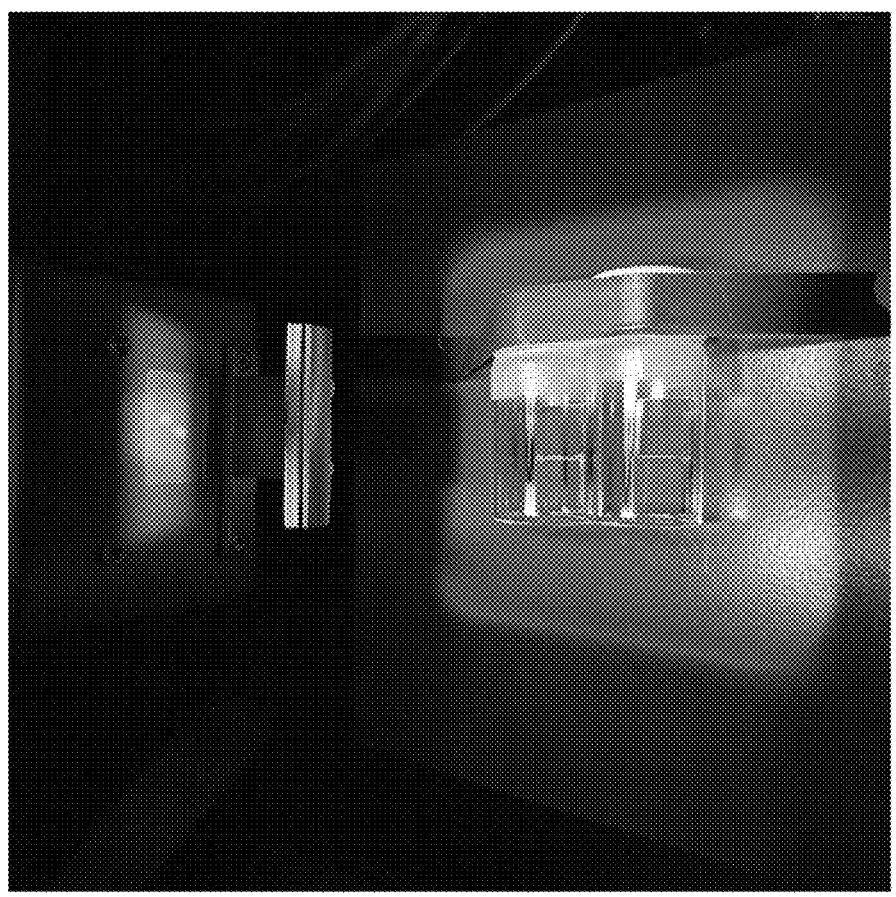
FIG. 17 shows the photograph of the aging condition for the mix-halide perovskite films with different AQS derivatives as additive, which were sealed in a 20 mL vial (filled with $N_2$) and illuminated for two days. The intensity of the simulated AM1.5G illumination is calibrated to 1-sun equivalent intensity.
Figure 18A:
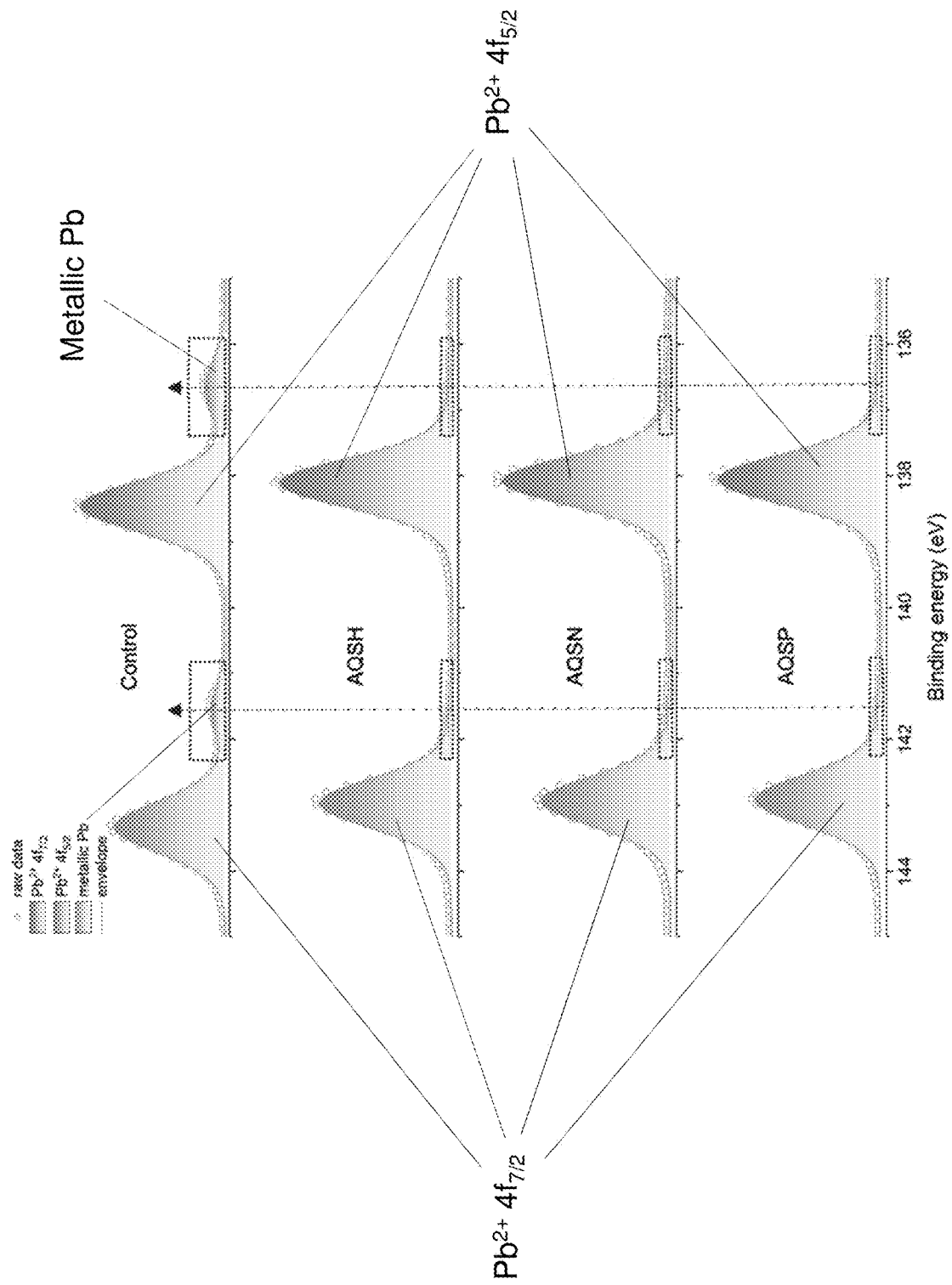
FIG. 18A shows the high-resolution X-ray photoelectron spectroscopy (XPS) spectra of Pb 4f of the aged perovskite films with different AQS derivatives.
Figure 18B:
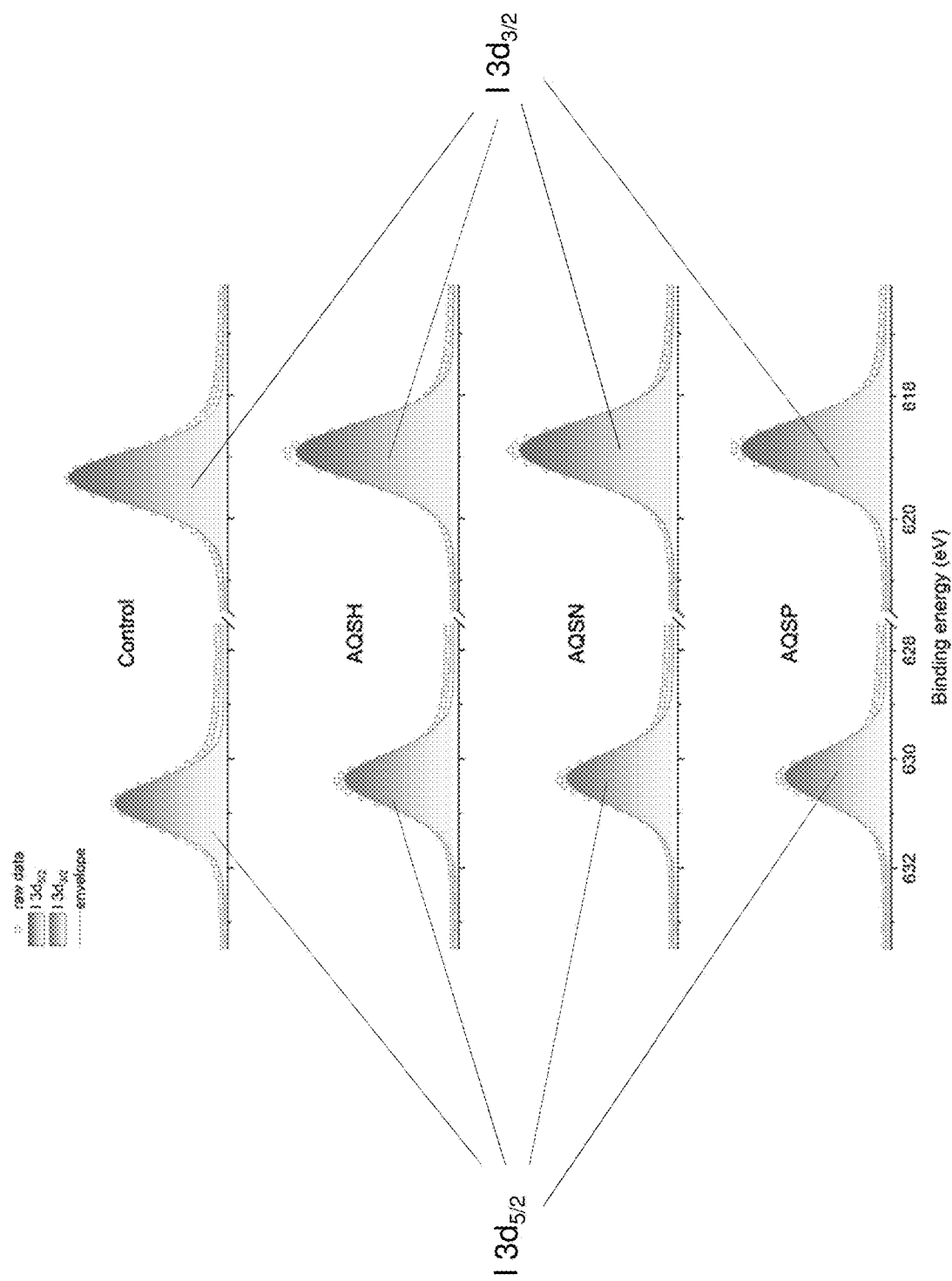
FIG. 18B shows the high-resolution X-ray photoelectron spectroscopy (XPS) spectra of I 3d of the aged perovskite films with different AQS derivatives.
Figure 18C:
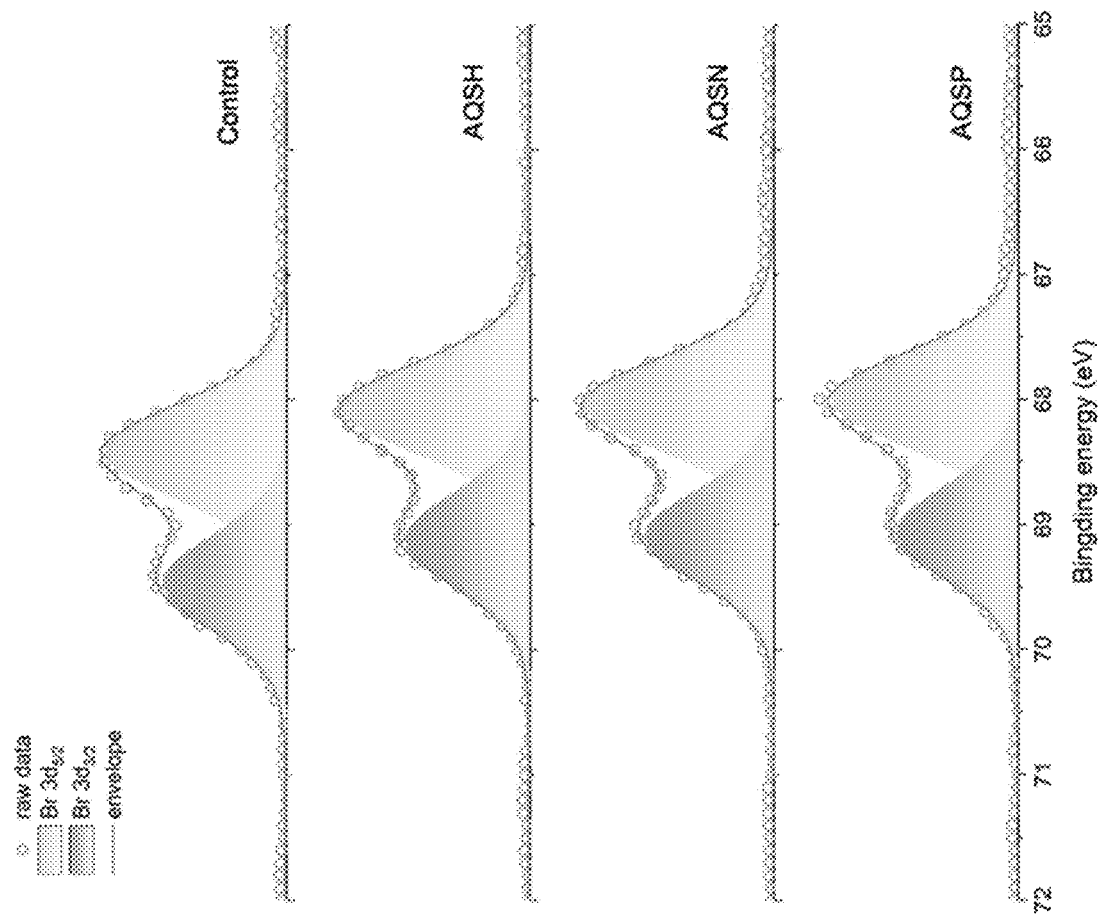
FIG. 18C shows the high-resolution X-ray photoelectron spectroscopy (XPS) spectra of Br 3d of the aged perovskite films with different AQS derivatives.

High-resolution X-ray photoelectron spectroscopy (XPS) was then used to study the surface property of the perovskite films that were aged under continuous illumination (AM 1.5G, 100 mW $cm^2$) (FIG. 17). To verify whether the AQS-based redox mediators help suppress the formation of $Pb^0$ and $I^0$, focus was put on Pb, I, and Br elements (FIGS. 18A to 18C). The binding energies (BEs) at approximately 138.1 eV and 142.9 eV were assigned to be Pb $4f_{7/2}$ and Pb $4f_{5/2}$ of the AQS-based perovskite films, respectively. Comparatively, the BE of Pb $4f_{7/2}$ and Pb $4f_{5/2}$ slightly shifted to 138.5 eV and 143.3 eV for the control sample. Furthermore, two distinct shoulder peaks (i.e., 136.7 eV and 141.6 eV) originating from metallic $Pb^0$ were observed in control perovskite, the primary decomposition product of perovskite under illumination.

Figure 19:
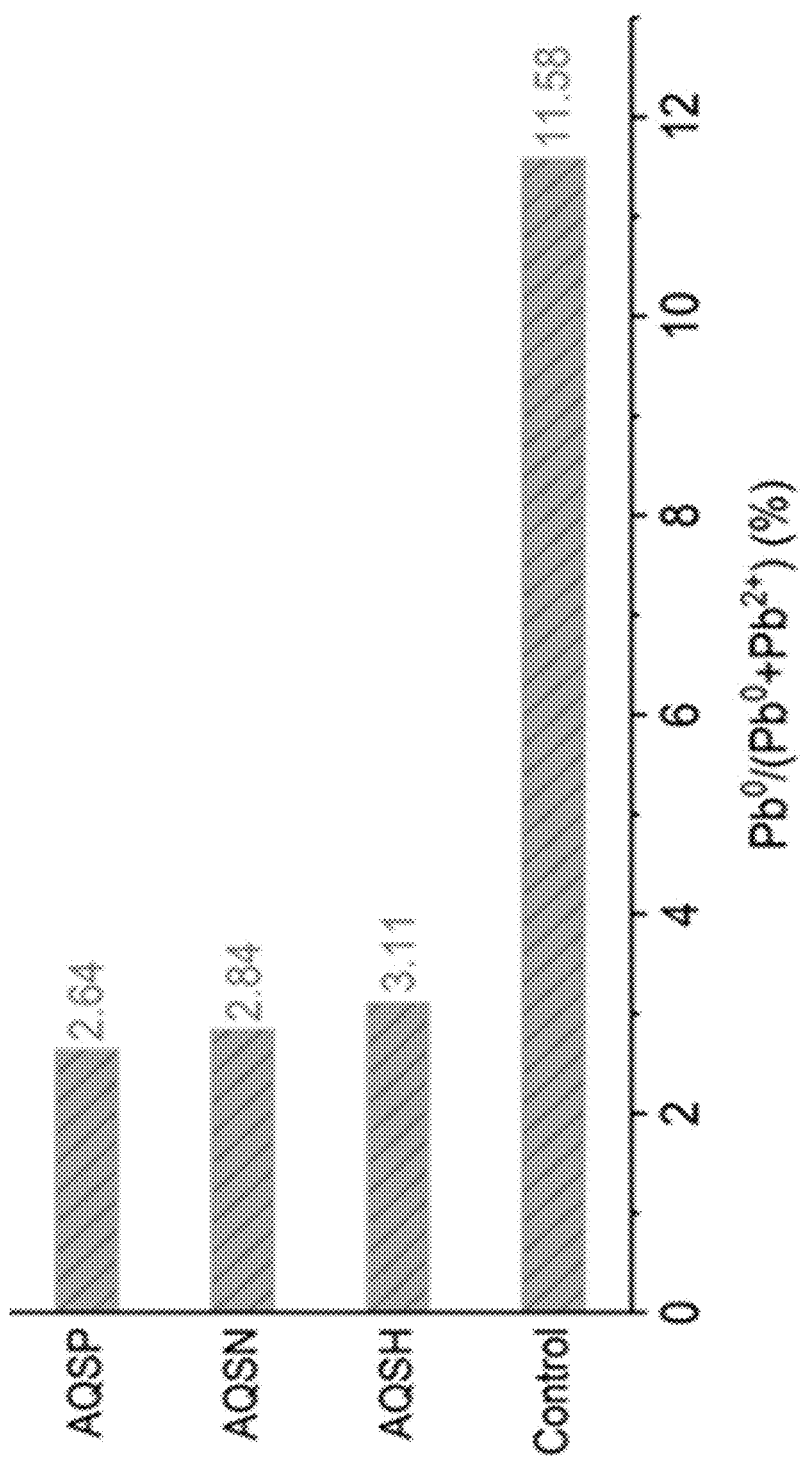
FIG. 19 shows the atomic ratio of metallic $Pb^0$ in total Pb element of the perovskite films with or without different AQS derivatives.
Figure 20B:
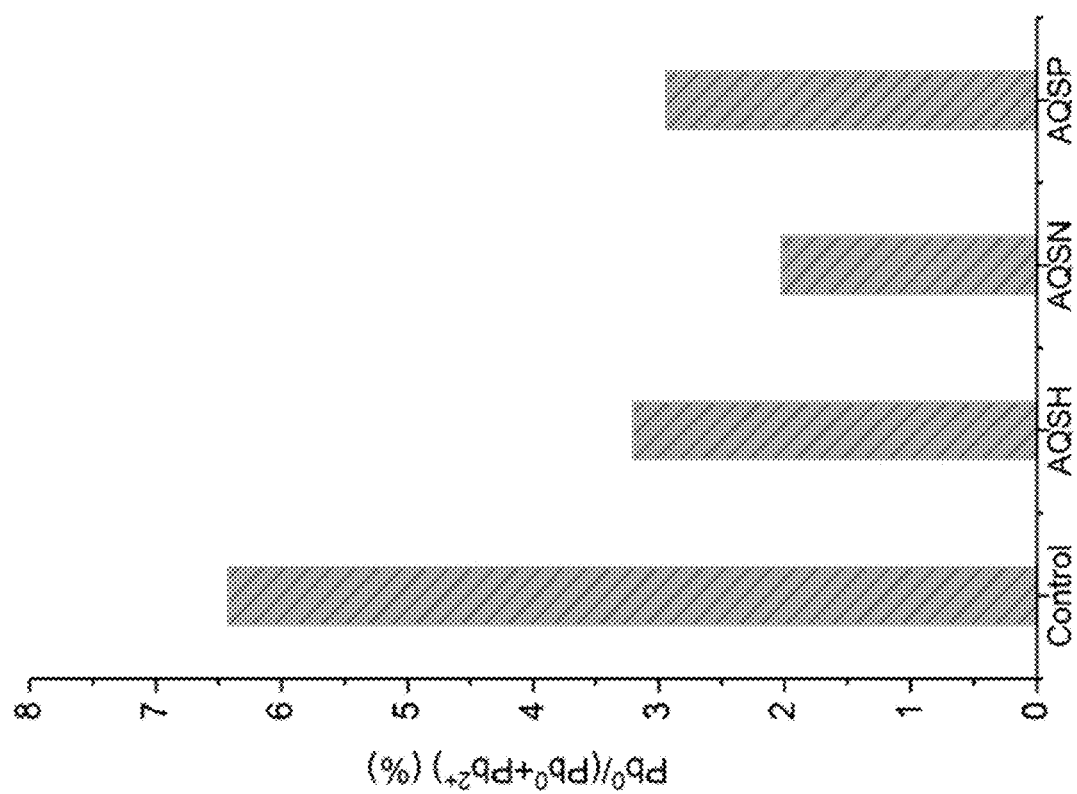
FIG. 20B shows the atomic ratio of metallic Pb ($Pb^0$) in total Pb ($Pb^{2+}+Pb^0$) element of the pristine perovskite films with or without different AQS derivatives.

The atomic ratio of metallic $Pb^0$ in total Pb was quantified and the results are shown in FIGS. 19, 20A and 20B. The control sample showed a high ratio of metallic $Pb^0$ at 11.58%, whereas it was between 2.64-3.11% for AQS-based perovskites. Such a considerable reduction in $Pb^0$ may be ascribed to its oxidation to $Pb^{2+}$ mediated by AQS derivatives, as evident in the previous results shown in FIGS. 8 to 12.

Figure 21:
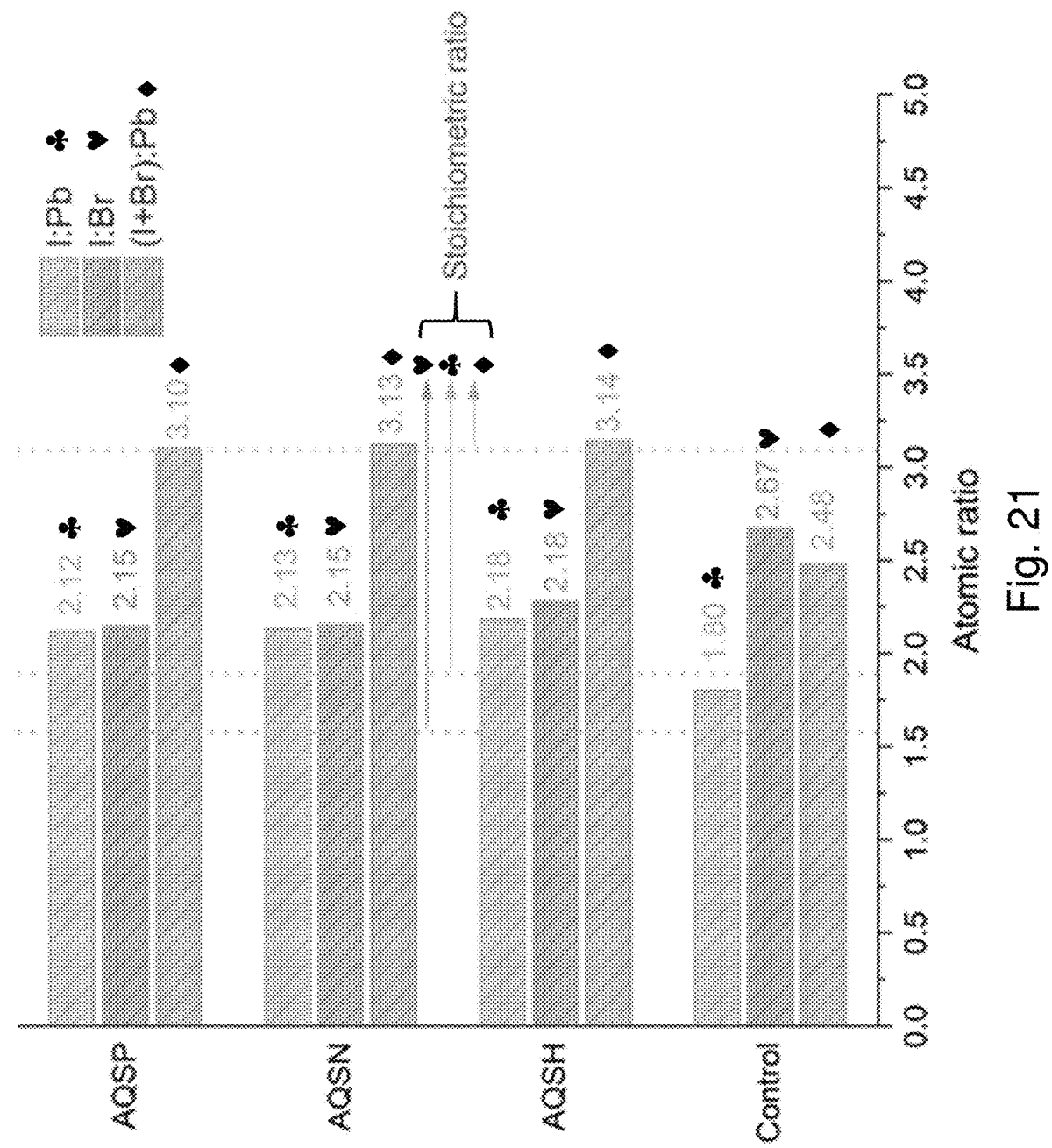
FIG. 21 shows the atomic ratio of I:Pb, I:Br, and (I+Br):Pb in the perovskite films with or without different different AQS derivatives.

Regarding halide elements, two peaks were observed in the control perovskite, with BEs of 619.3 eV and 630.8 eV, originating from I $3d_5s_2$ and I $3d_3/2$, respectively (FIG. 18B). Given the volatile nature of iodine products, the relative atomic ratios were used to study the halide distribution on the illuminated perovskite surface (FIG. 21). It is noted that I/Pb atomic ratios of AQS-based perovskite films (2.12-2.18) were slightly higher than the stoichiometric ratio (denoted by the dashed lines), while the (I+Br)/Pb atomic ratios close to stoichiometric ratio (3.09). This non-uniformity in composition might be ascribed to different nucleation/crystallization dynamics for I- and Br-based perovskites. Nevertheless, it is found that the loss of halide species in control perovskite, as the atomic ratio of (I+Br)/Pb (2.48) was far below its stoichiometric ratio of 3.09. Considering its I/Pb atomic ratio of 1.80, this halide content loss is attributed to be the iodine species because of their lower oxidation potential than bromides (1.065 V). Meanwhile, the increased I/Br ratio of 2.67 in the control sample suggests the faster migration of Br along the direction of incident light as reported.

Example 6

Structural Properties and Density Functional Theory (DFT) Calculations

Figure 22:
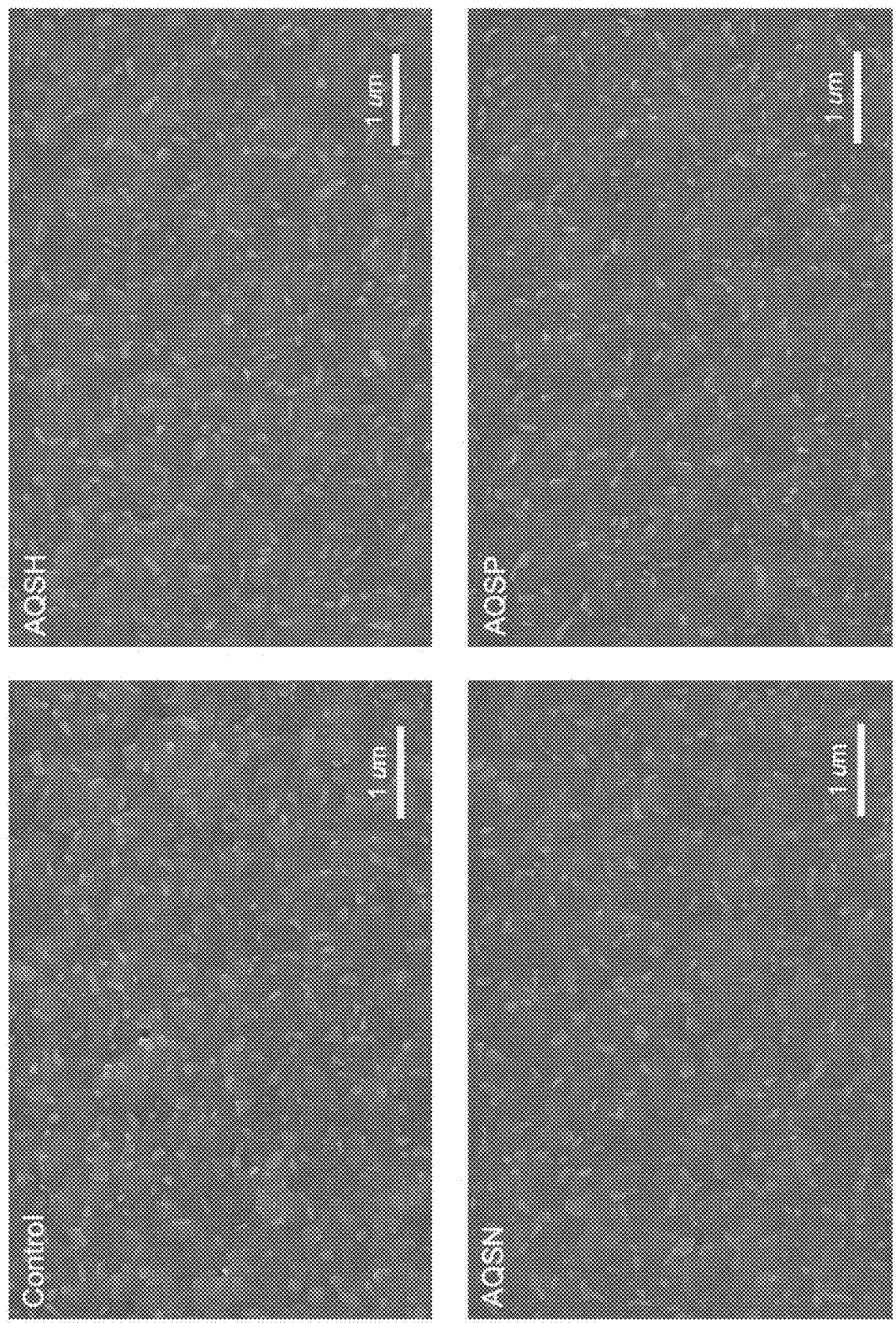
FIG. 22 shows the top-viewing SEM images of the perovskite films with or without AQS derivatives.
Figure 23:
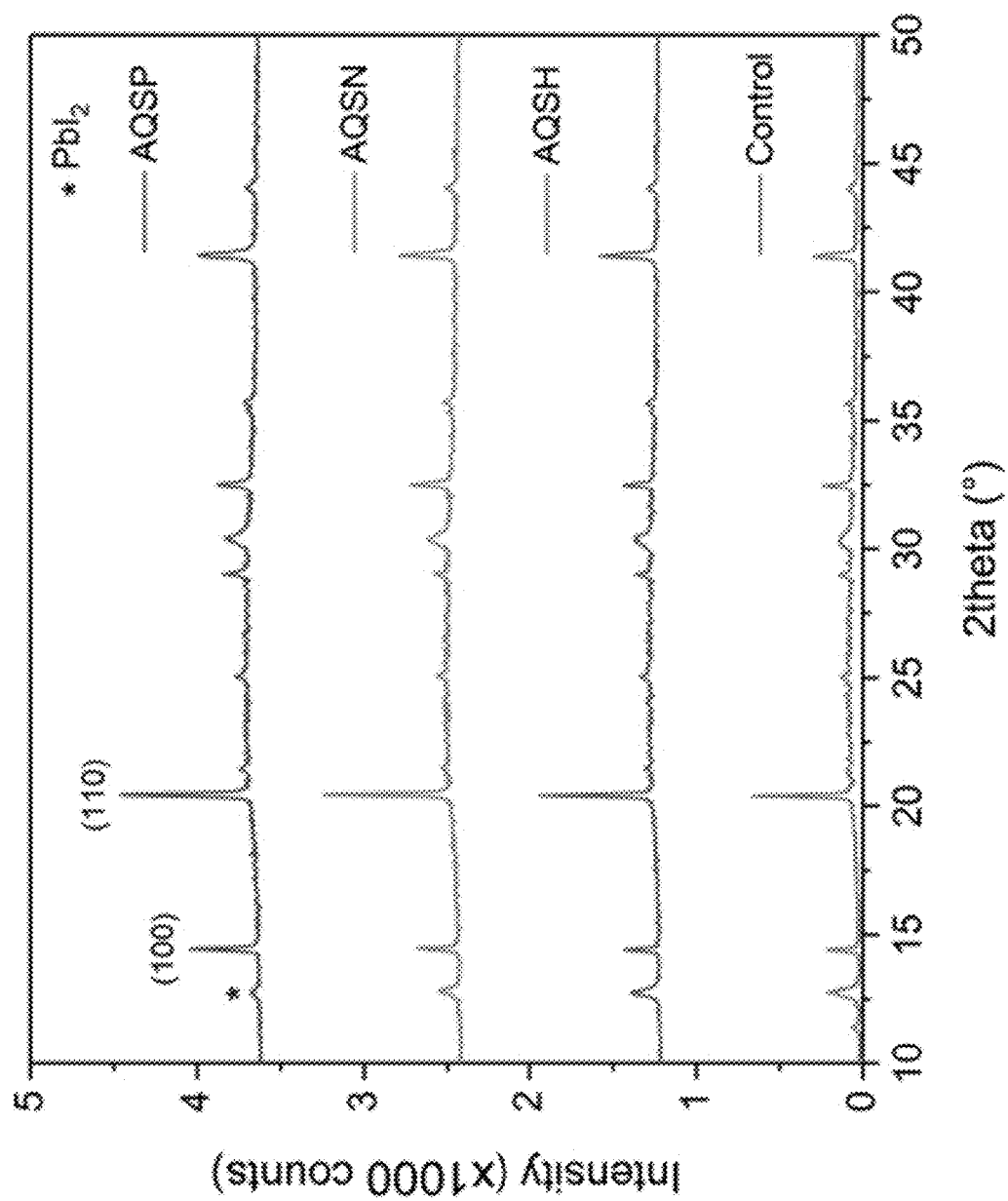
FIG. 23 shows the thin film XRD patterns of the perovskite films with or without AQS derivatives.
Figure 24:
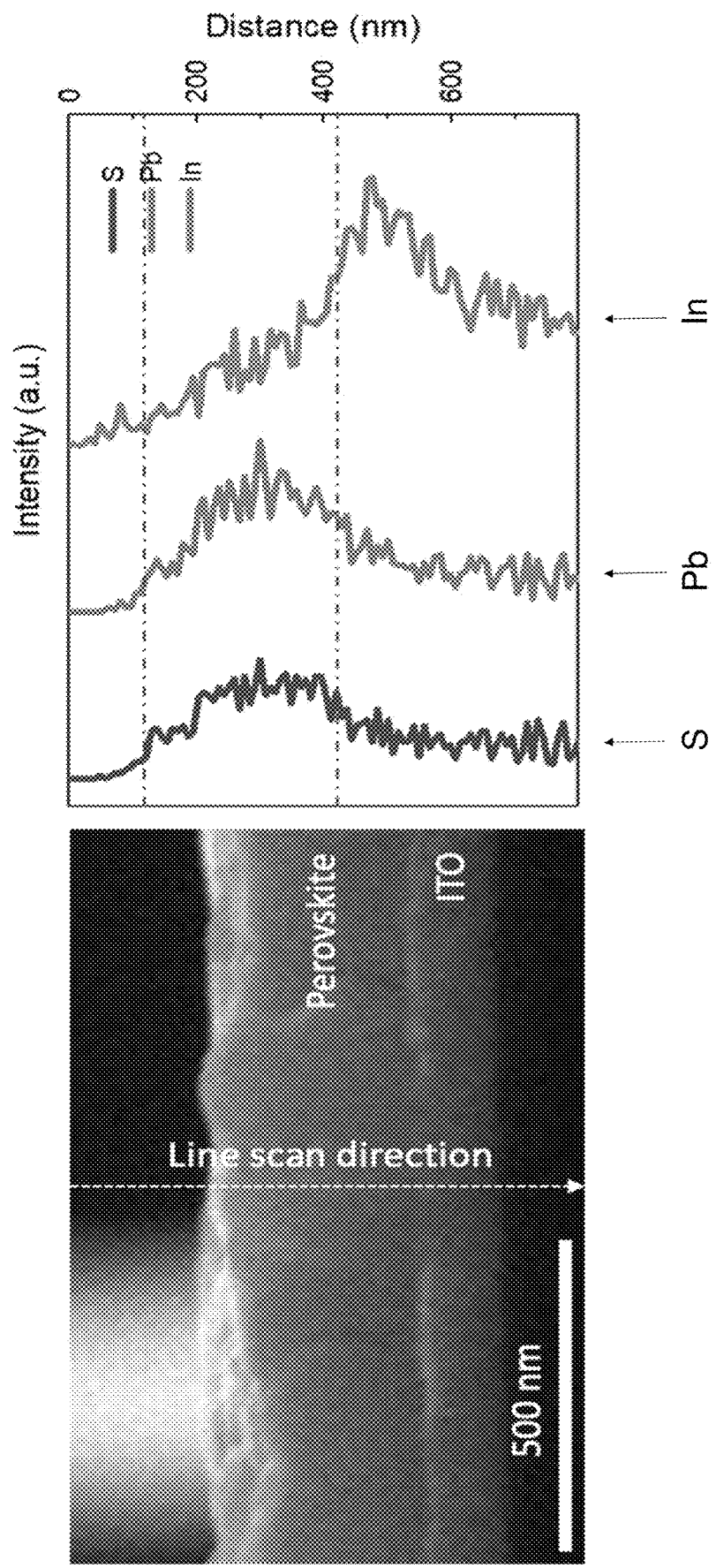
FIG. 24 shows the cross-sectional SEM image and EDX elemental distribution (line scan for S, Pb, and In elements) for the perovskite film (prepared on ITO substrate) with AQSH as the additive.
Figure 25:
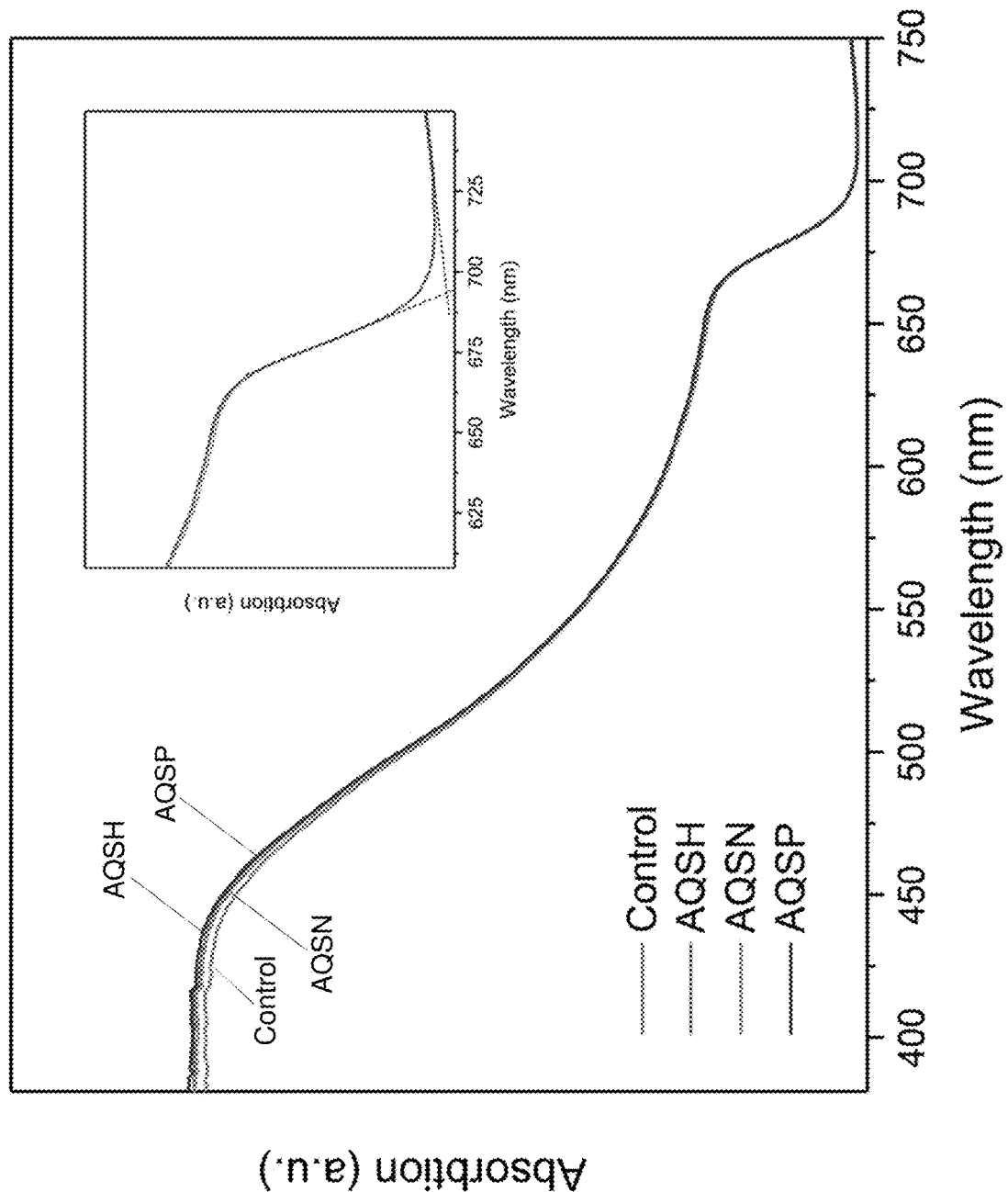
FIG. 25 shows the UV-vis absorption spectra of the perovskite films with or without AQS derivatives.

The structural properties of the perovskite films were studied by using scanning electron microscopy (SEM) and XRD, and the results are shown in FIGS. 22 and 23. All XRD patterns revealed two prominent diffraction peaks at 2θ of 14.4° and 20.4°, corresponding to the (100) and (110) lattice planes of perovskites. Lower intensity of the diffraction peak from $PbI_2$ was observed for the AQSN- and AQSP-based perovskites, which might be ascribed to the modulation effect of the substituted cations on perovskite growth. The top-viewing SEM images exhibited no obvious differences in the morphology of the samples. The distribution of AQS-derivatives within the perovskite layer was profiled by cross-sectional SEM-energy dispersive spectroscopy (SEM-EDX), which shows uniform distribution (FIG. 24). It is also determined the optical bandgap of the perovskite films to be approximately 1.79 eV by their UV-vis absorption spectra, as presented in FIG. 25.

Figure 26A:
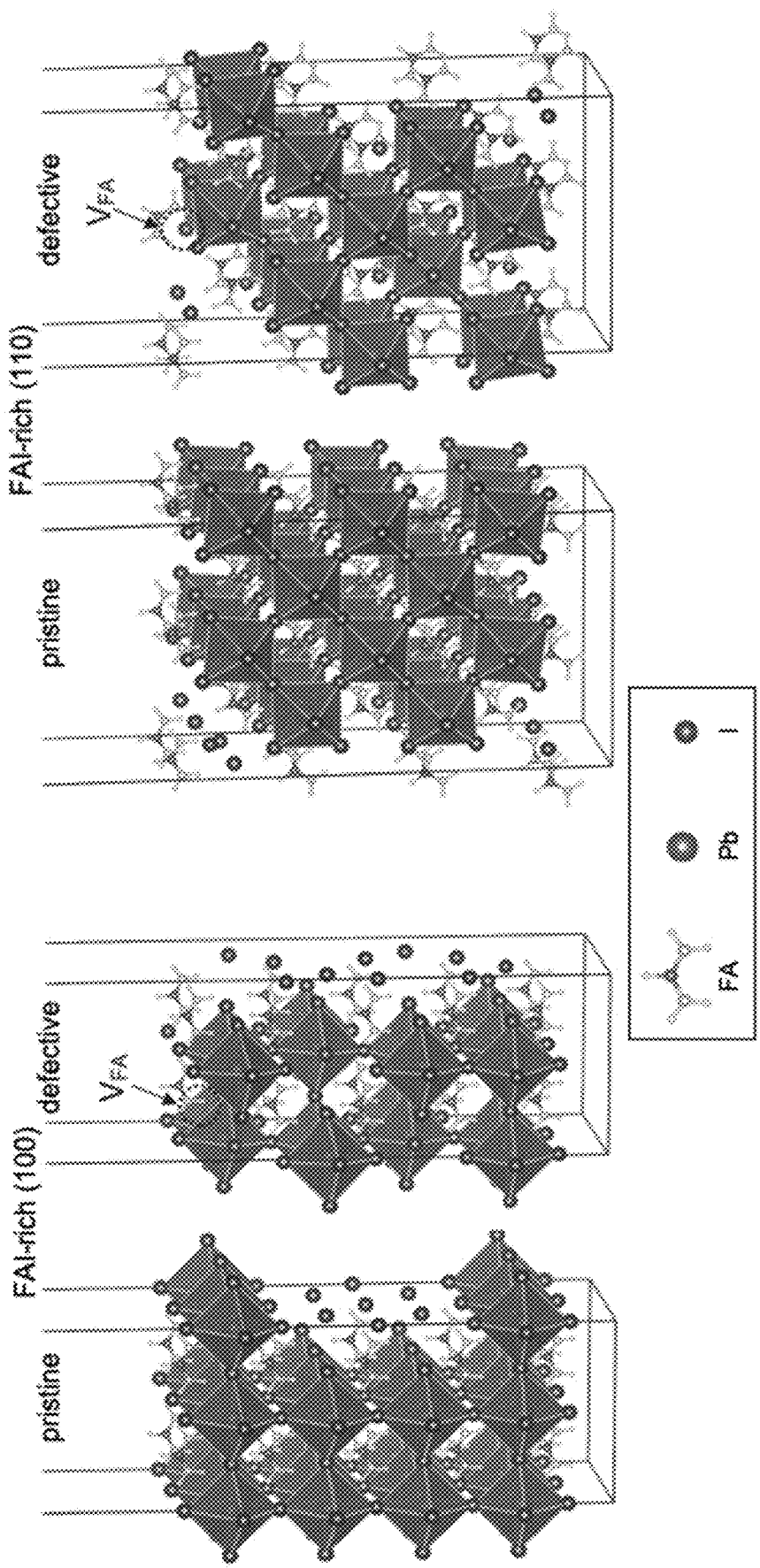
FIG. 26A shows the optimized slab structures for pristine FAI-rich and defective FAI-rich (100)/(110) upon density functional theory (DFT) calculations based on redox mediator/perovskite interfacial models.
Figure 26B:
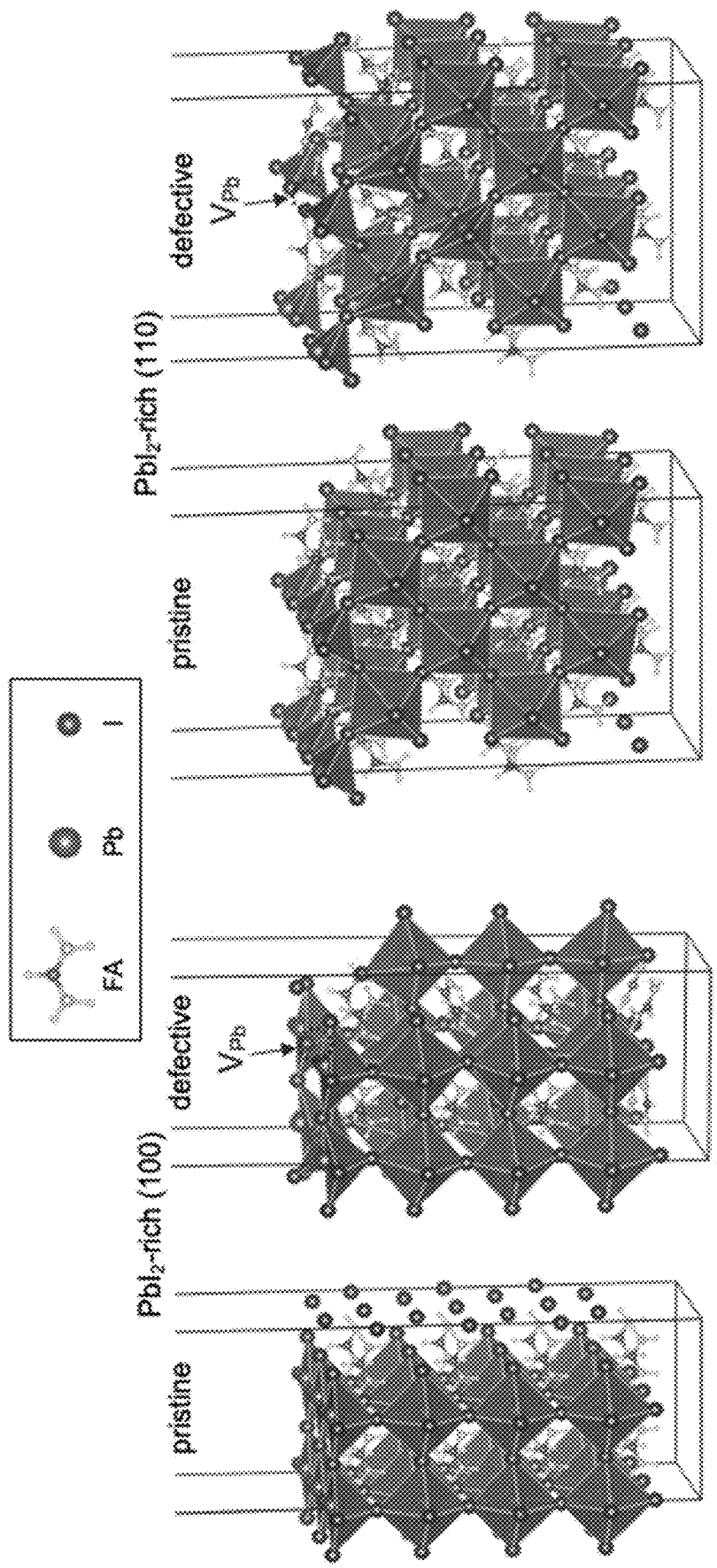
FIG. 26B shows the optimized slab structures for pristine $PbI_2$-rich and defective $PbI_2$-rich (100)/(110) upon density functional theory (DFT) calculations based on redox mediator/perovskite interfacial models.
Figure 27A:
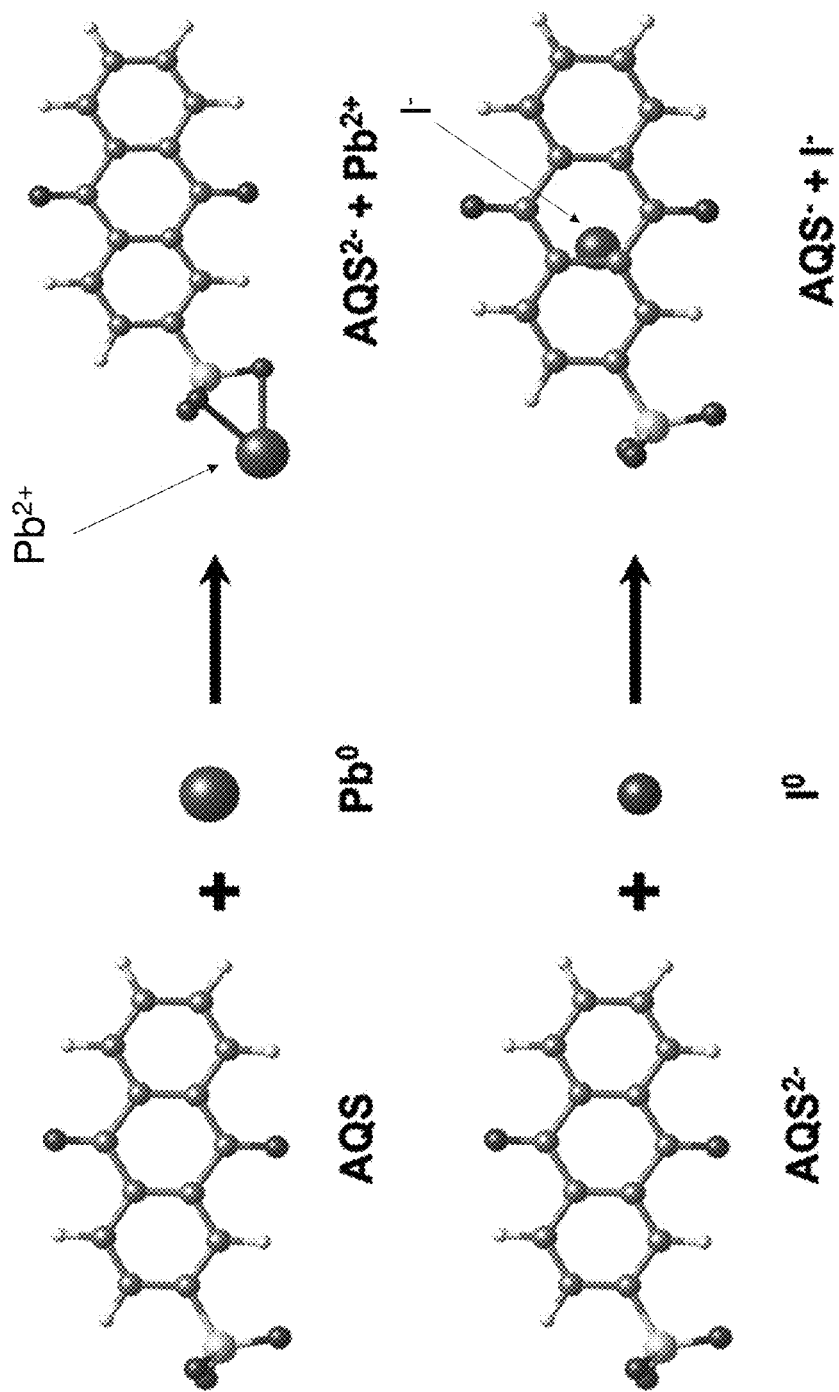
FIG. 27A is a schematic diagram illustrating the half-reactions between AQS core, $I^0$, and $Pb^0$.
Figure 27B:
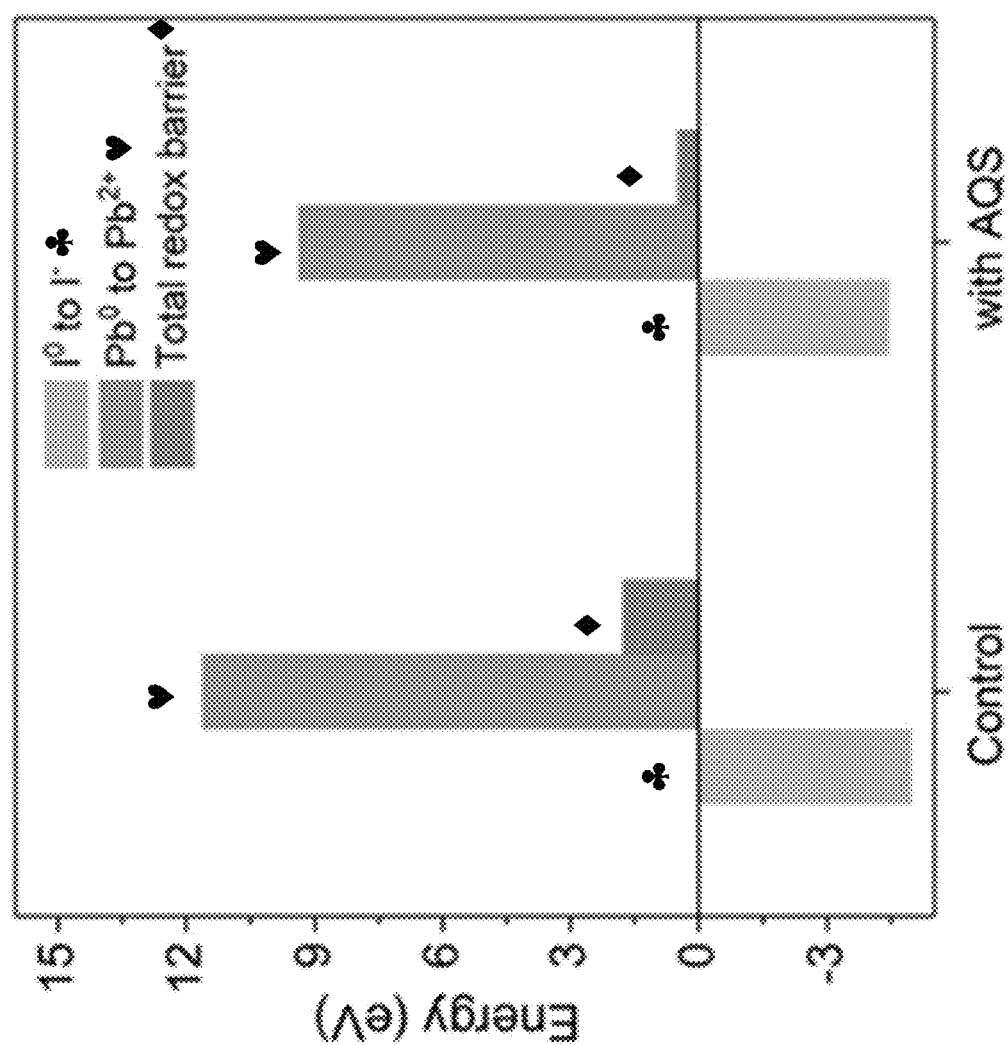
FIG. 27B shows the calculated energy barrier for the half-reaction from $I^0$ to $I^-$ and $Pb^0$ to $Pb^{2+}$, and the total energy barrier for redox charge shuttling.

Based on the above structural analysis, density functional theory (DFT) calculations was performed on redox mediator/perovskite interfacial models to gain insights into the role of AQS derivatives in facilitating the overall redox reaction and passivating perovskite, as well as to estimate their interactions. Two representative perovskite surfaces were taken into consideration, each with different terminations (FAI- and PbI$_2$-rich) and surface defects ($V_{FA}$ and $V_{Pb}$), as depicted in FIGS. 26A and 26B. The energy barriers of the half-reactions associated with the elimination of Pb$^0$ and I$^0$ were first calculated (FIGS. 27A and 27B). The results indicated that the half-reaction from Pb$^0$ to Pb$^{2+}$ presented a considerable energy barrier (11.6 eV), while the reduction from I$^0$ to I$^-$ was more thermodynamically favored for pristine perovskite (−5.0 eV). Upon introducing AQS derivatives onto perovskite surface, the energy barriers for both half-reactions were reduced. The total energy barrier for the redox reaction was lowered by more than threefold (from 1.76 eV to 0.49 eV), verifying the ability of these molecules in facilitating electron shuttling within the perovskite.

Figure 28:
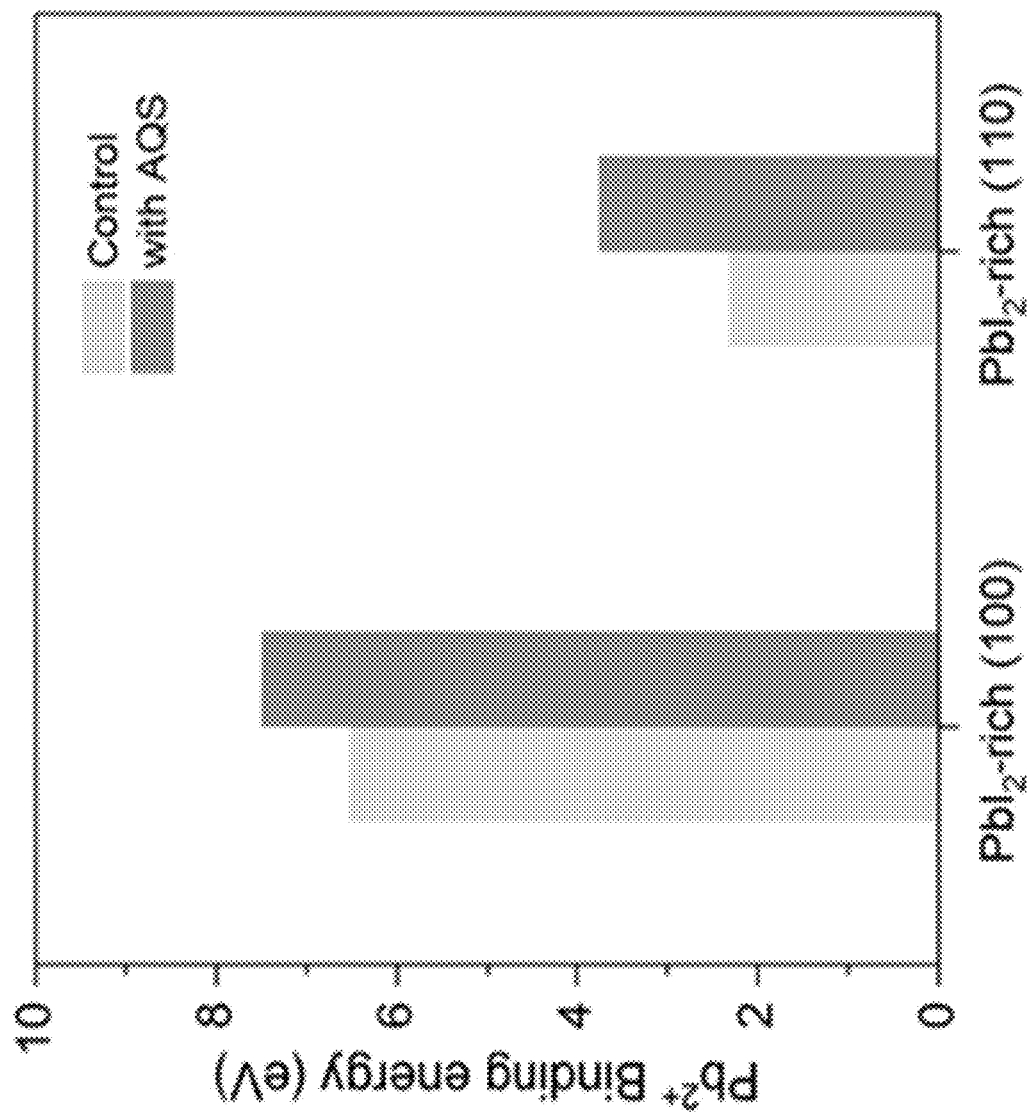
FIG. 28 shows the surface $Pb^{2+}$ binding energy for the $PbI_2$-rich $FAPbI_3$ (100) and (110) surface with or without AQS adsorption.
Figure 29:
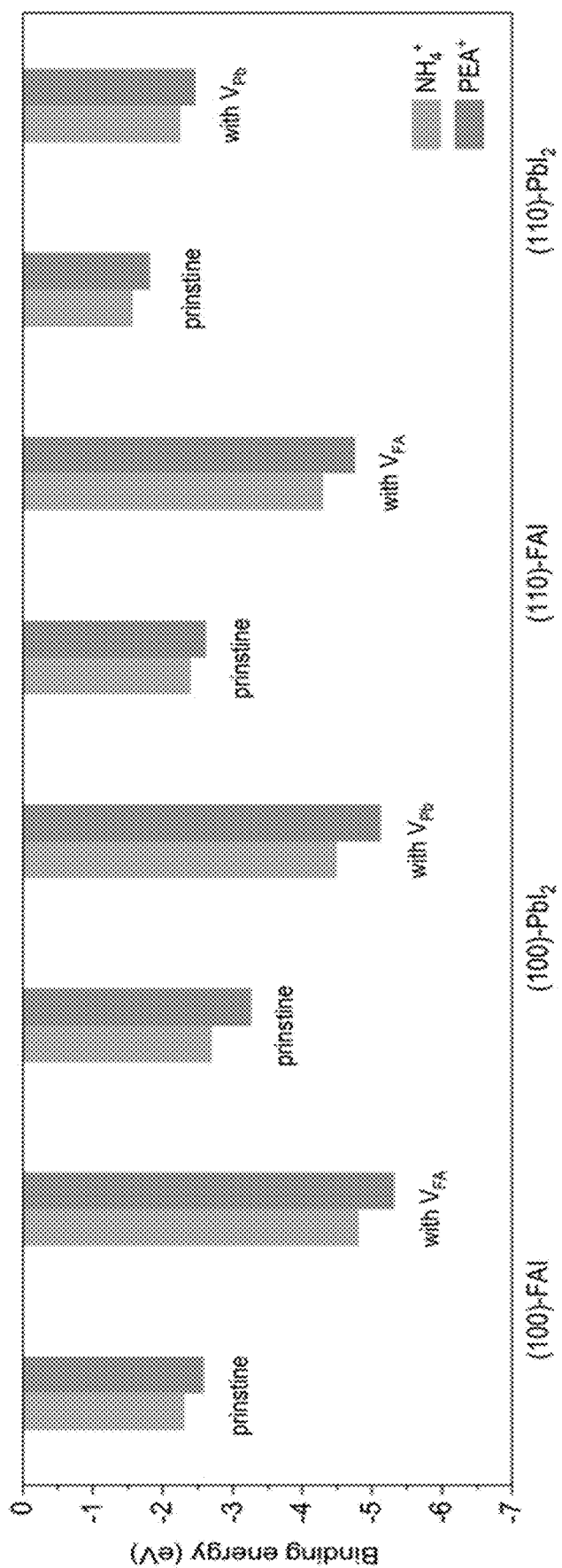
FIG. 29 shows the calculated binding energies between $NH_4^+$ ($PEA^+$) and pristine/defective $FAPbI_3$ (100) and (110) surfaces.
Figure 30B:
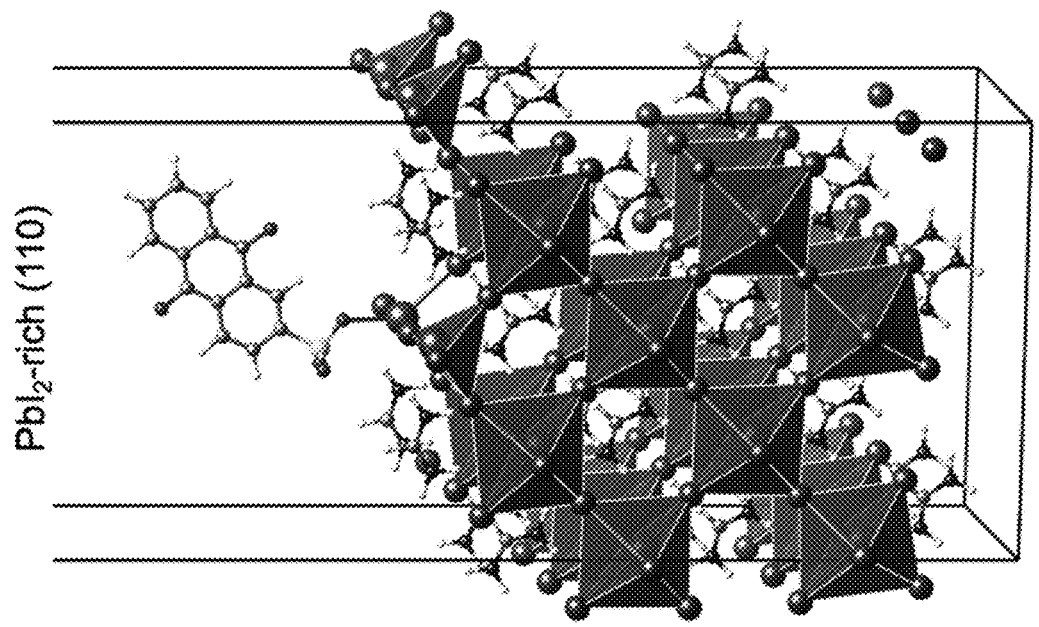
FIG. 30B shows the optimized crystal structure for pristine $PbI_2$-rich (110) with AQS adsorption. The optimization were performed at GGA/PBE+vdW level of theory.
Figure 30A:
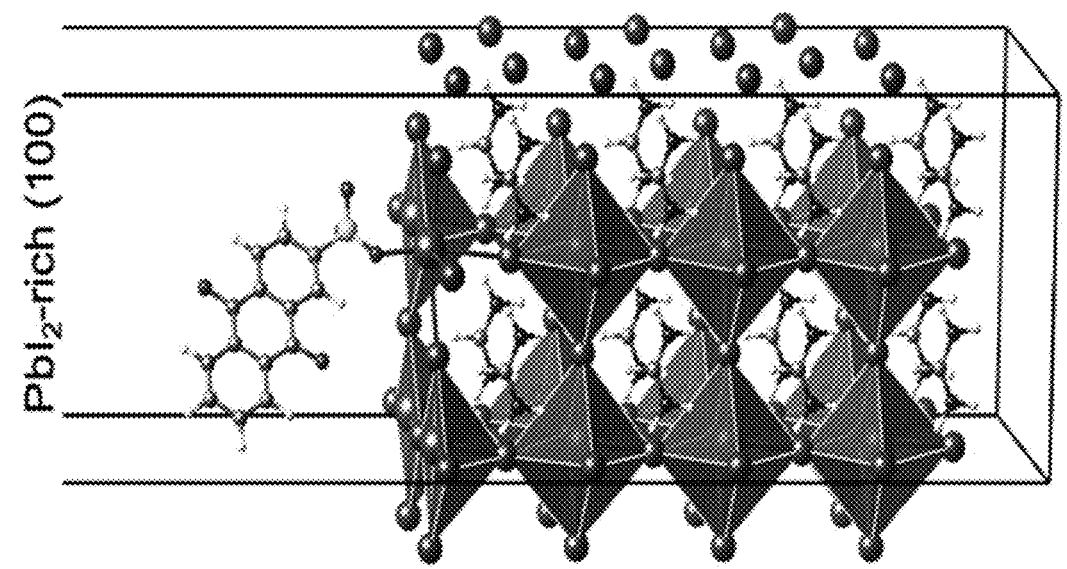
FIG. 30A shows the optimized crystal structure for pristine $PbI_2$-rich (100) with AQS adsorption. The optimization were performed at GGA/PBE+vdW level of theory.
Figure 31B:
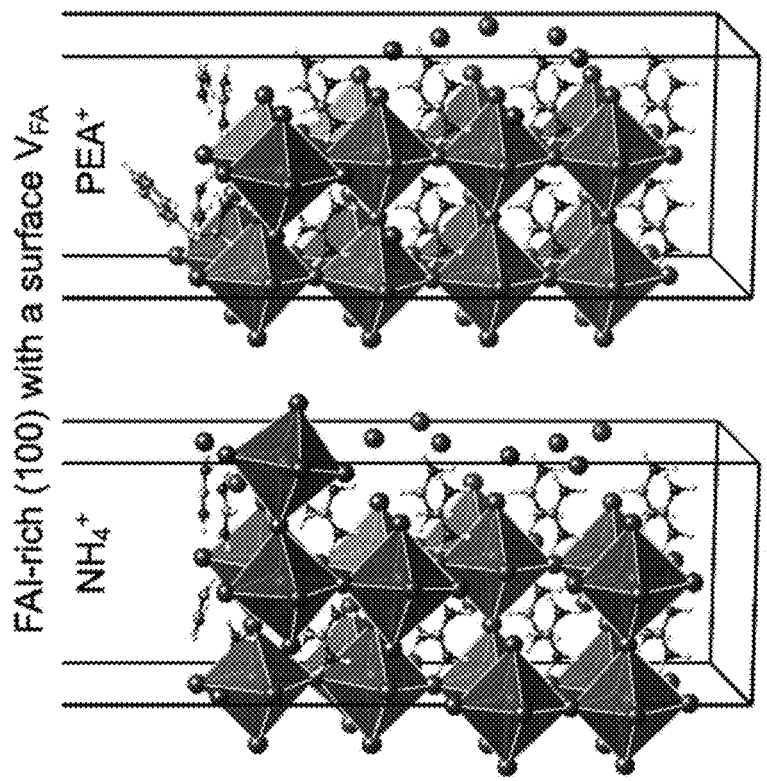
FIG. 31B shows the optimized crystal structure for defective FAI-rich (100)-$V_{FA}$ with $NH_4^+$ and $PEA^+$ adsorption. The optimizations were performed at GGA/PBE+vdW level of theory.
Figure 31A:
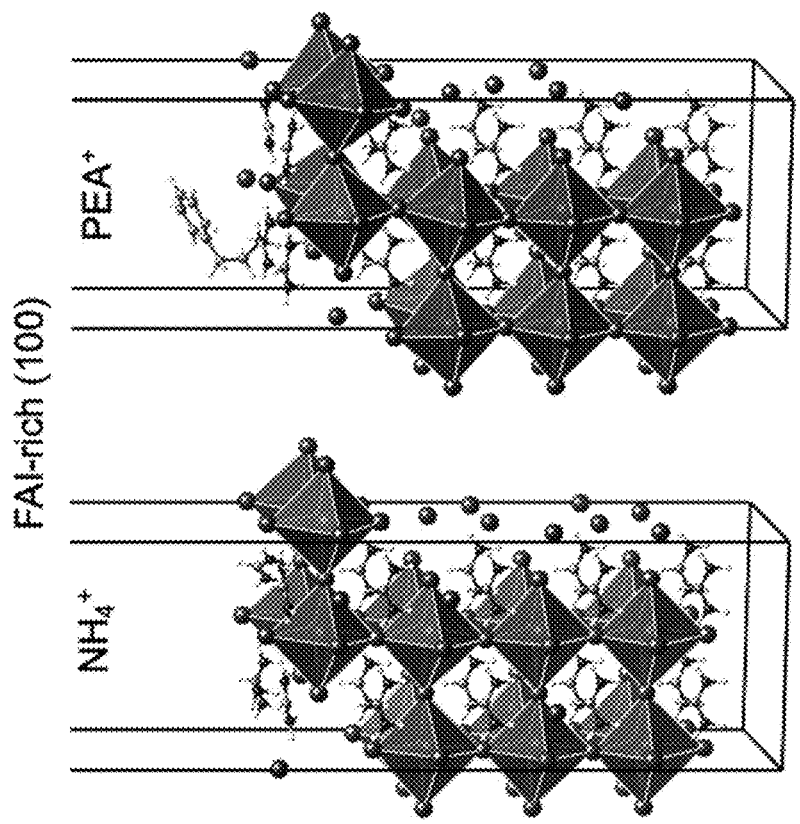
FIG. 31A shows the optimized crystal structure for pristine FAI-rich (100) with $NH_4^+$ and $PEA^+$ adsorption. The optimizations were performed at GGA/PBE+vdW level of theory.
Figures 31C, 31D:
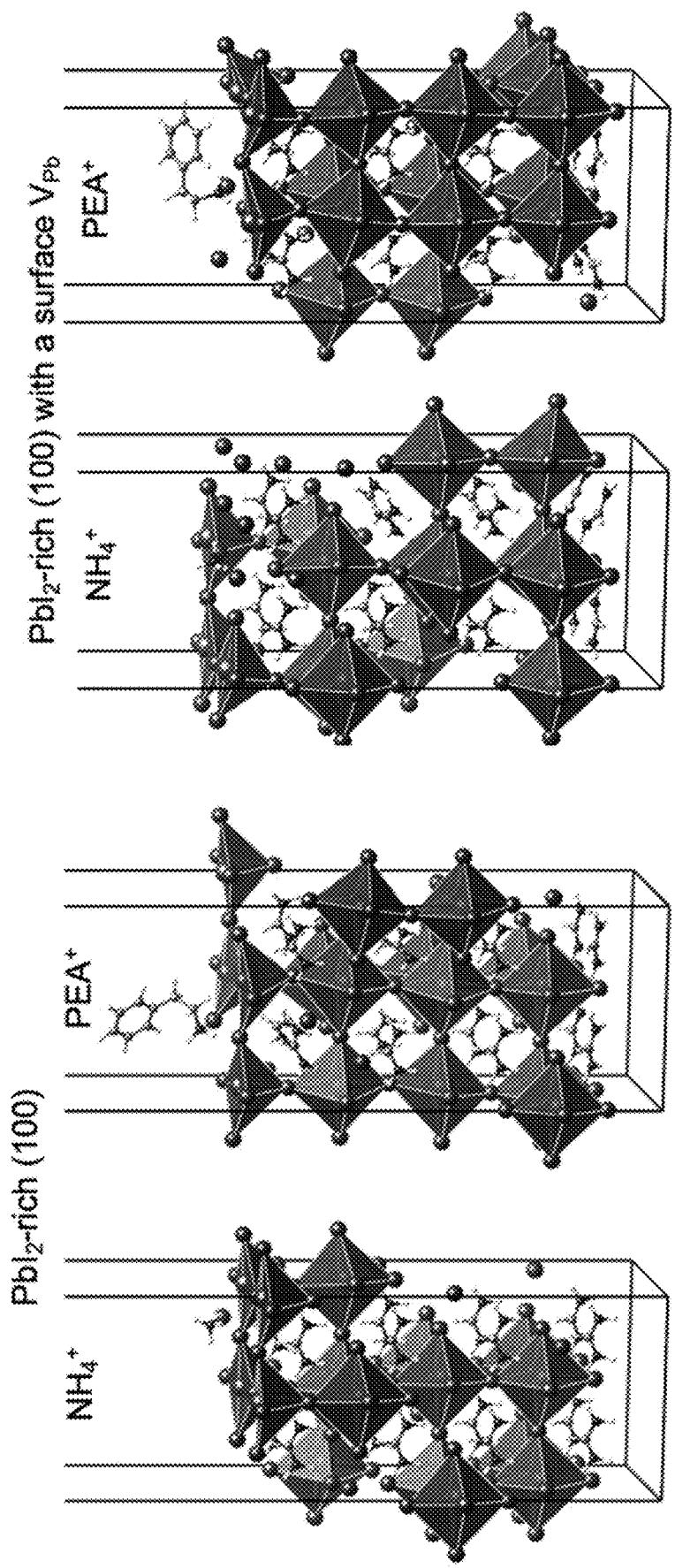
FIG. 31C shows the optimized crystal structure for pristine $PbI_2$-rich (100) with $NH_4^+$ and $PEA^+$ adsorption. The optimizations were performed at GGA/PBE+vdW level of theory.
FIG. 31D shows the optimized crystal structure for defective $PbI_2$-rich (100)-$V_{Pb}$ with $NH_4^+$ and $PEA^+$ adsorption. The optimizations were performed at GGA/PBE+vdW level of theory.
Figures 32A, 32B:
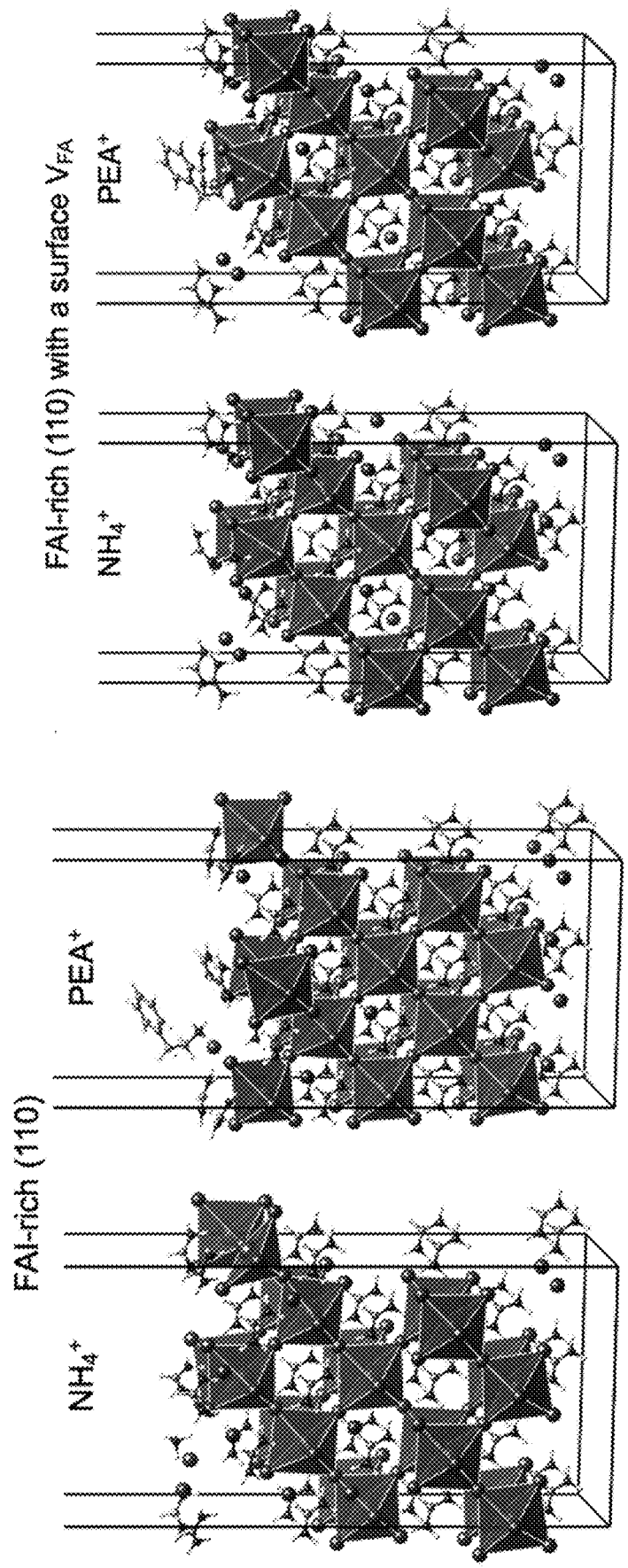
FIG. 32A shows the optimized crystal structure for pristine FAI-rich (110) with $NH_4^+$ and $PEA^+$ adsorption. The optimizations were performed at GGA/PBE+vdW level of theory.
FIG. 32B shows the optimized crystal structure for defective FAI-rich (110)-$V_{FA}$ with $NH_4^+$ and $PEA^+$ adsorption. The optimizations were performed at GGA/PBE+vdW level of theory.
Figures 32C, 32D:
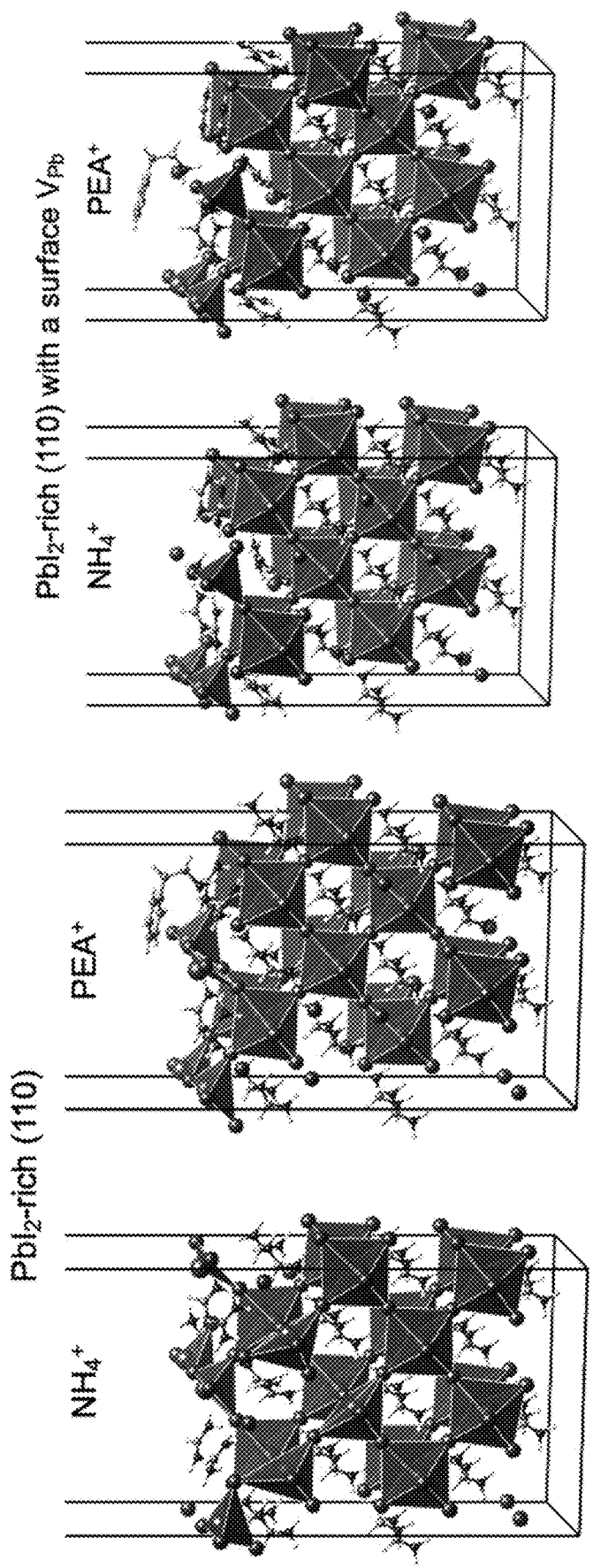
FIG. 32C shows the optimized crystal structure for pristine $PbI_2$-rich (110) with $NH_4^+$ and $PEA^+$ adsorption. The optimizations were performed at GGA/PBE+vdW level of theory.
FIG. 32D shows the optimized crystal structure for defective $PbI_2$-rich (110)-$V_{Pb}$ with $NH_4^+$ and $PEA^+$ adsorption. The optimizations were performed at GGA/PBE+vdW level of theory.
Figures 33A, 33B:
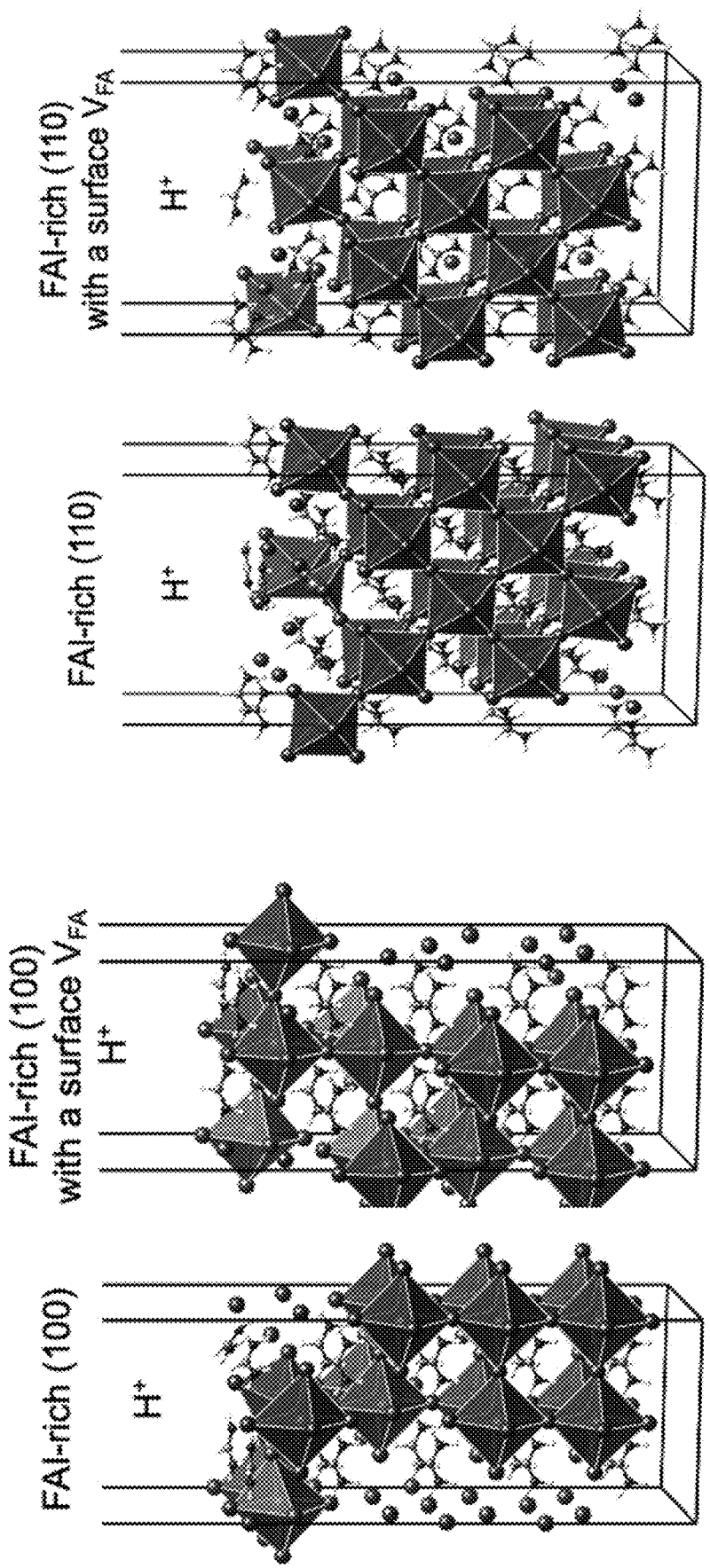
FIG. 33A shows the optimized crystal structure for pristine FAI-rich (100) and defective FAI-rich (100)-$V_{FA}$ with $H^+$ adsorption.
FIG. 33B shows the optimized crystal structure for pristine $PbI_2$-rich (100) and defective $PbI_2$-rich (100)-$V_Pe$ with $H^+$ adsorption.
Figures 33C, 33D:
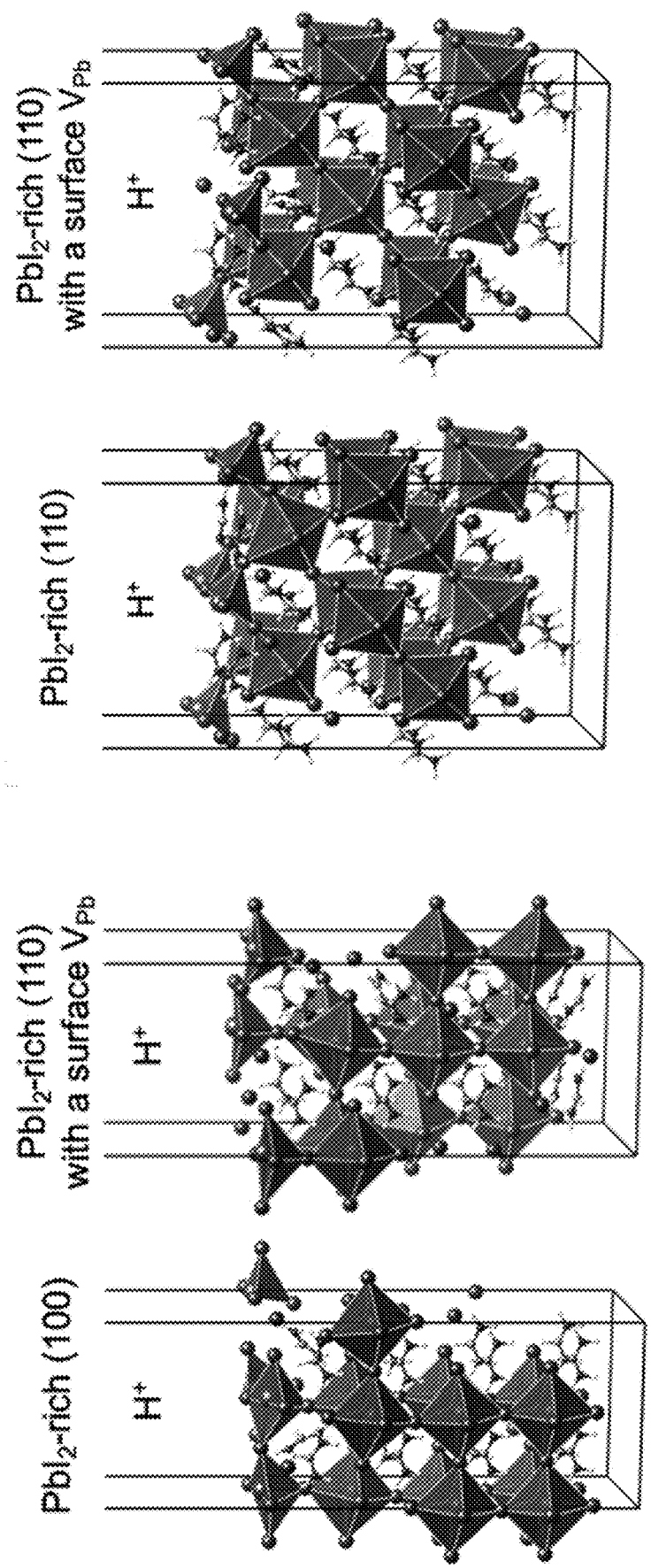
FIG. 33C shows the optimized crystal structure for pristine FAI-rich (110) and defective FAI-rich (110)-$V_{FA}$ with $H^+$ adsorption.
FIG. 33D shows the optimized crystal structure for pristine $PbI_2$-rich (110) and defective $PbI_2$-rich (110)-$V_Pe$ with $H^+$ adsorption.
Figure 34:
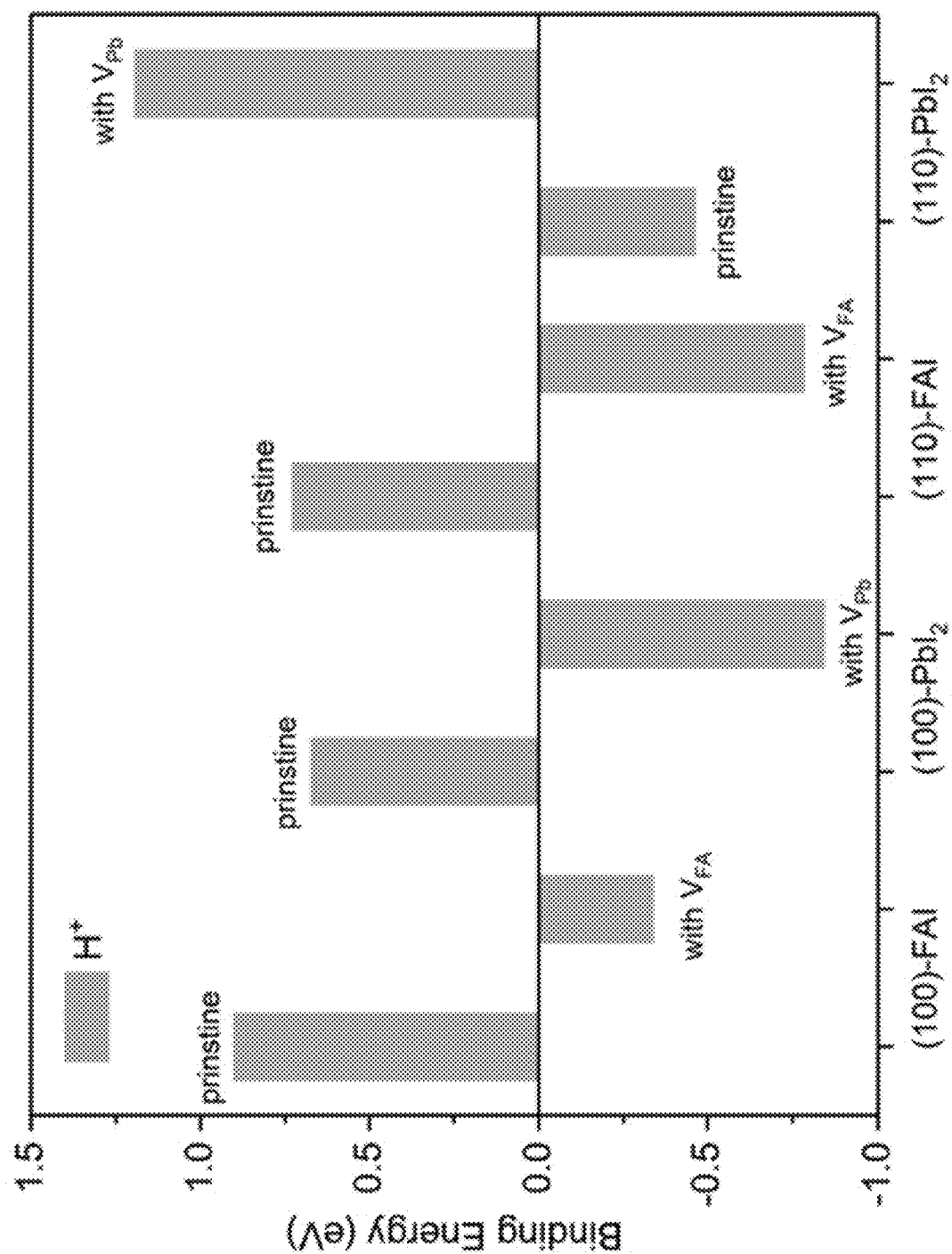
FIG. 34 shows the calculated binding energies between $H^+$ and pristine/defective $FAPbI_3$ (100) and (110) surfaces.

As discussed in Example 4, the AQS core governs the redox capability, while the substitution of —H by —NH$_4$ and —PEA affords the molecules with an additional defect passivation effect. The binding energies between AQS$^-$ and Pb$^{2+}$ were calculated to be 7.50 eV and 3.75 eV at the PbI$_2$-rich (100) and (110) surfaces, respectively, which were higher than those of the control perovskites (FIG. 28). The stronger binding with Pb$^{2+}$ is crucial for stabilizing the perovskites. Moreover, the binding energy between NH$_4^+$/PEA$^+$ and perovskite surfaces were calculated (FIG. 29). The optimized crystal structures of the redox mediators-modified perovskites are presented in FIGS. 30A-30B, 31A-31D, 32A-32D, 33A-33D, and 34. The results suggest that the PEA$^+$ cation provides a stronger defect passivation effect than NH$_4^+$, regardless of lattice plane and surface properties, as it consistently exhibits higher binding energies to the perovskite surface.

Figure 35A:
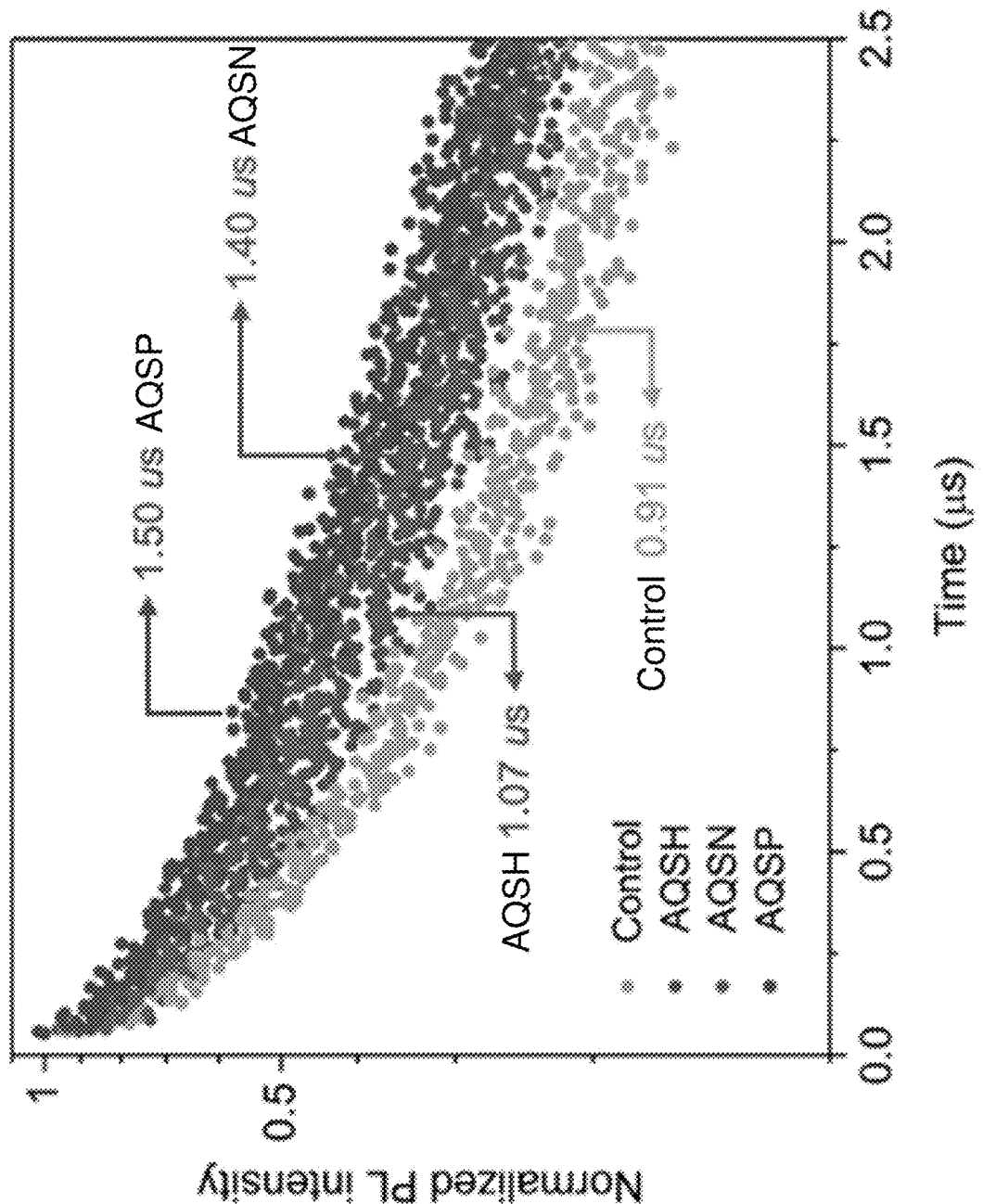
FIG. 35A shows the time-resolved PL (trPL) spectra of the perovskite films incorporated with different AQS derivatives.

Time-resolved PL (trPL) measurements were conducted on the perovskite films to investigate the defect passivation effect of AQS derivatives (FIG. 35A). The average carrier lifetime ($\tau_{avg}$) was calculated to be 0.91 μs for control perovskite, and slightly increased to 1.07 μs for AQSH-based perovskite (FIG. 35B). Notably, the carrier lifetime of 1.40 μs and 1.50 μs were obtained for AQSN- and AQSP-based perovskite, respectively. As the prolonged carrier lifetime usually indicates enhanced radiative recombination, space-charge-limited current (SCLC) method was used to quantify the trap density ($N_{trap}$) in the perovskites (FIG. 36A). The trap-filled limit voltages ($V_{TFL}$) were first extracted by fitting the J-V curves, then the $N_{trap}$ values were calculated to be 2.68×10$^{16}$, 2.51×10$^{16}$, 1.61×10$^{16}$, and 1.13×10$^{16}$ cm$^{-3}$ for control, AQSH-, AQSN- and AQSP-based perovskites, respectively (FIG. 36B).

Example 7

Photovoltaic Performance of PSCs and PO-TSCs

Figure 37A:
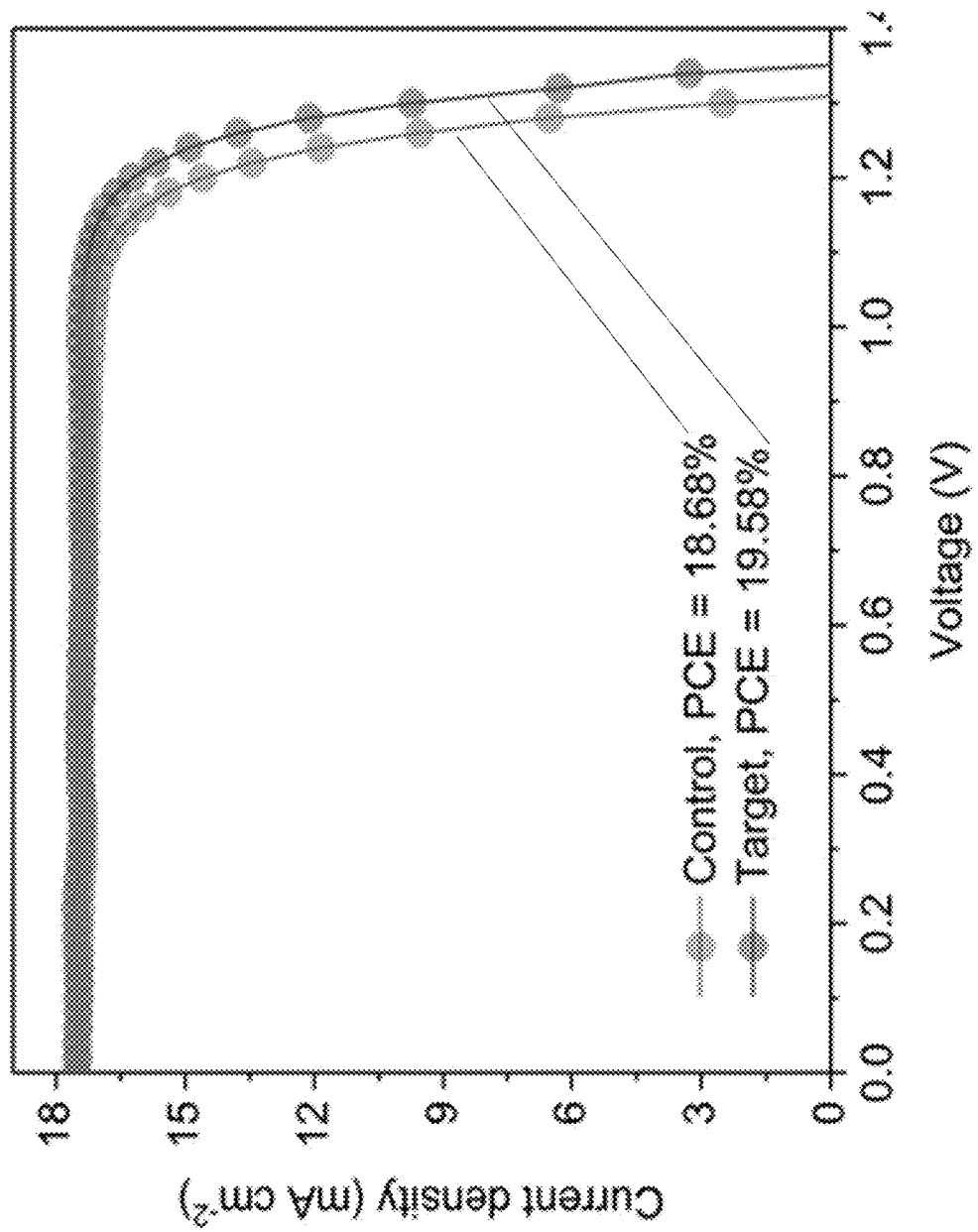
FIG. 37A shows the J-V curves of the control and target single-junction PSCs (perovskite with AQSP as additive). The initial efficiency of control and target single-junction PSCs are 18.08% and 18.89%, respectively.
Figure 37B:
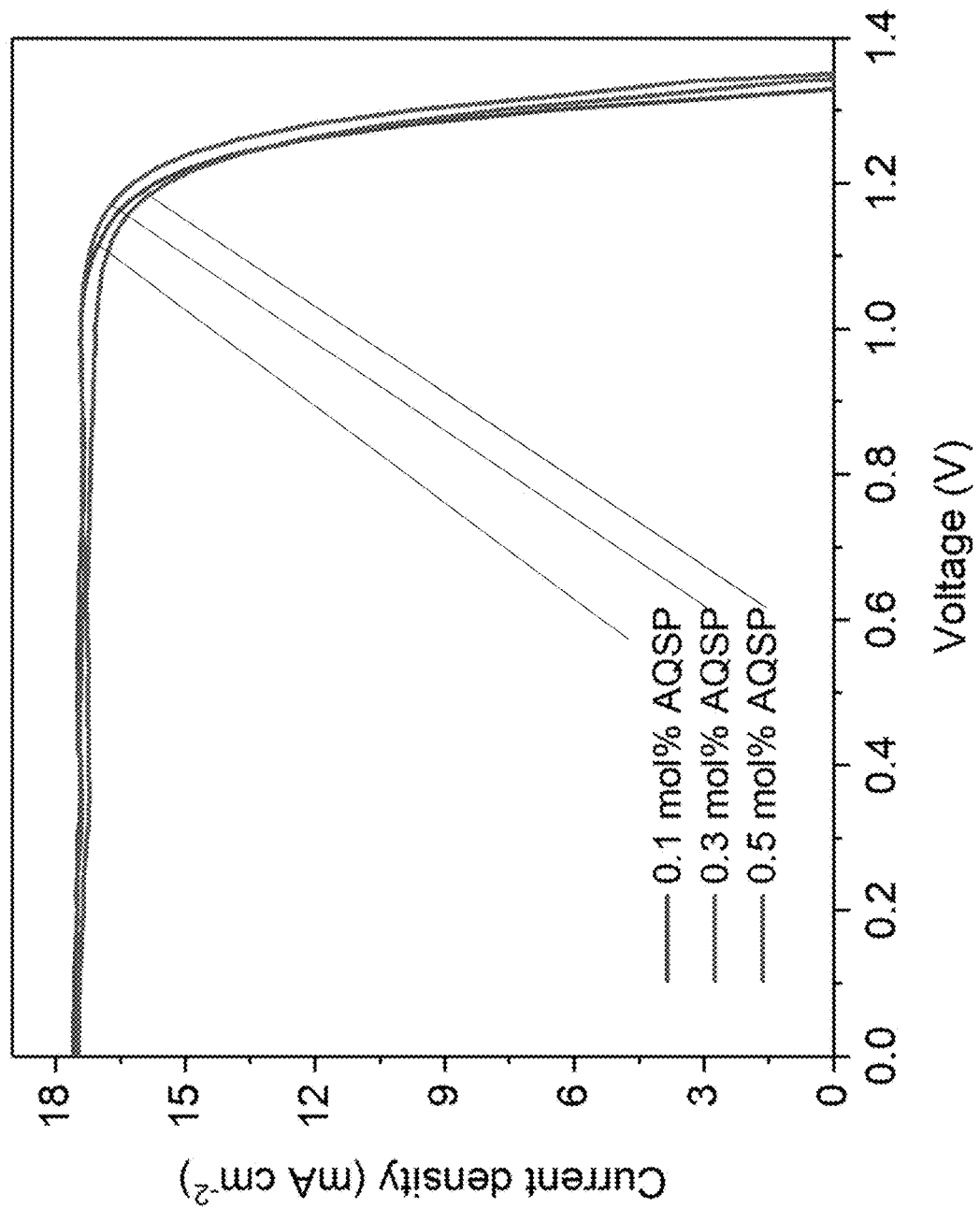
FIG. 37B shows the J-V curves of the single-junction PSCs based on the perovskites with different concentrations of AQSP.
Figure 37C:
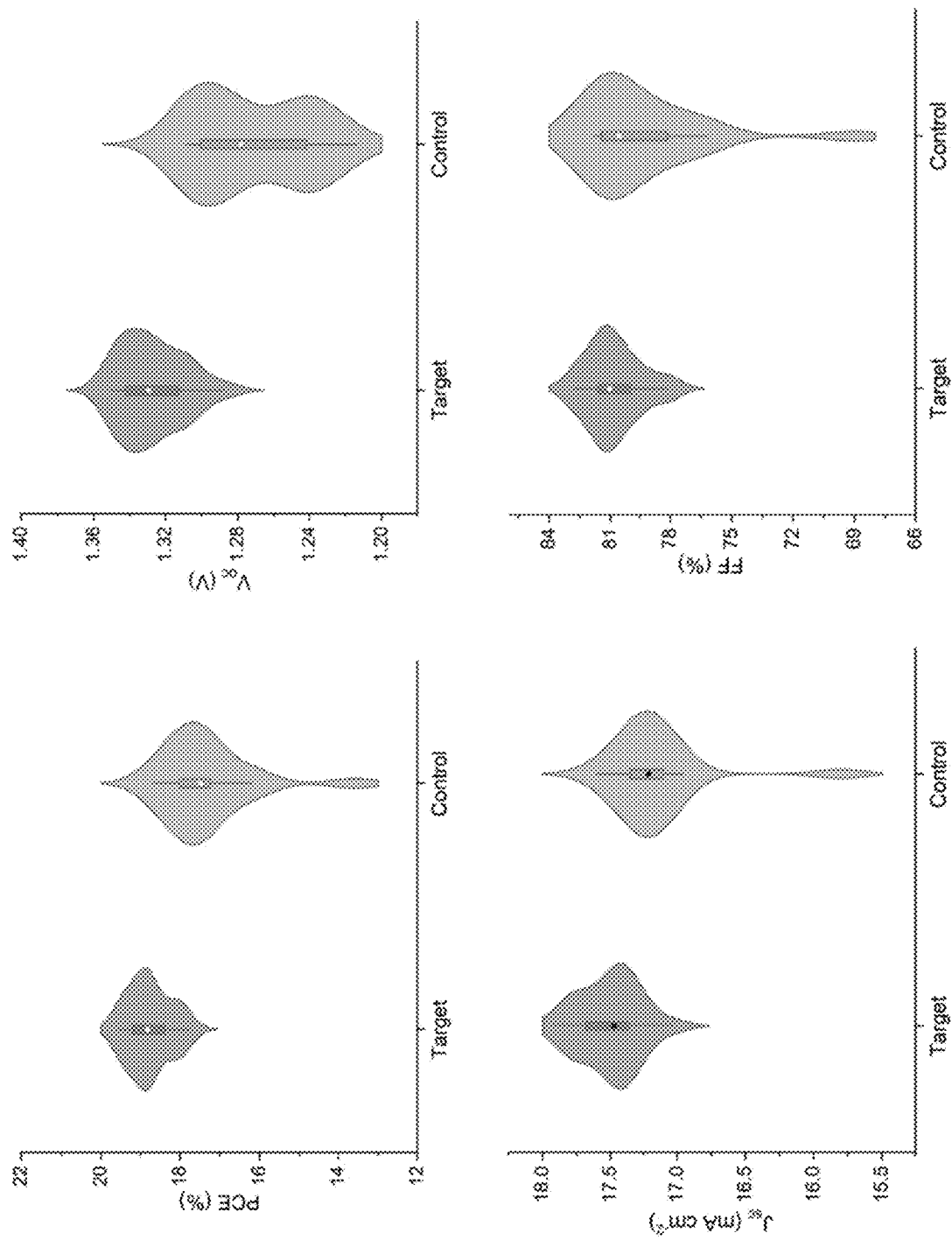
FIG. 37C shows the violin plots comparing the photovoltaic parameters of the control and target PSCs (20 devices fabricated from different batches)
Figure 38:
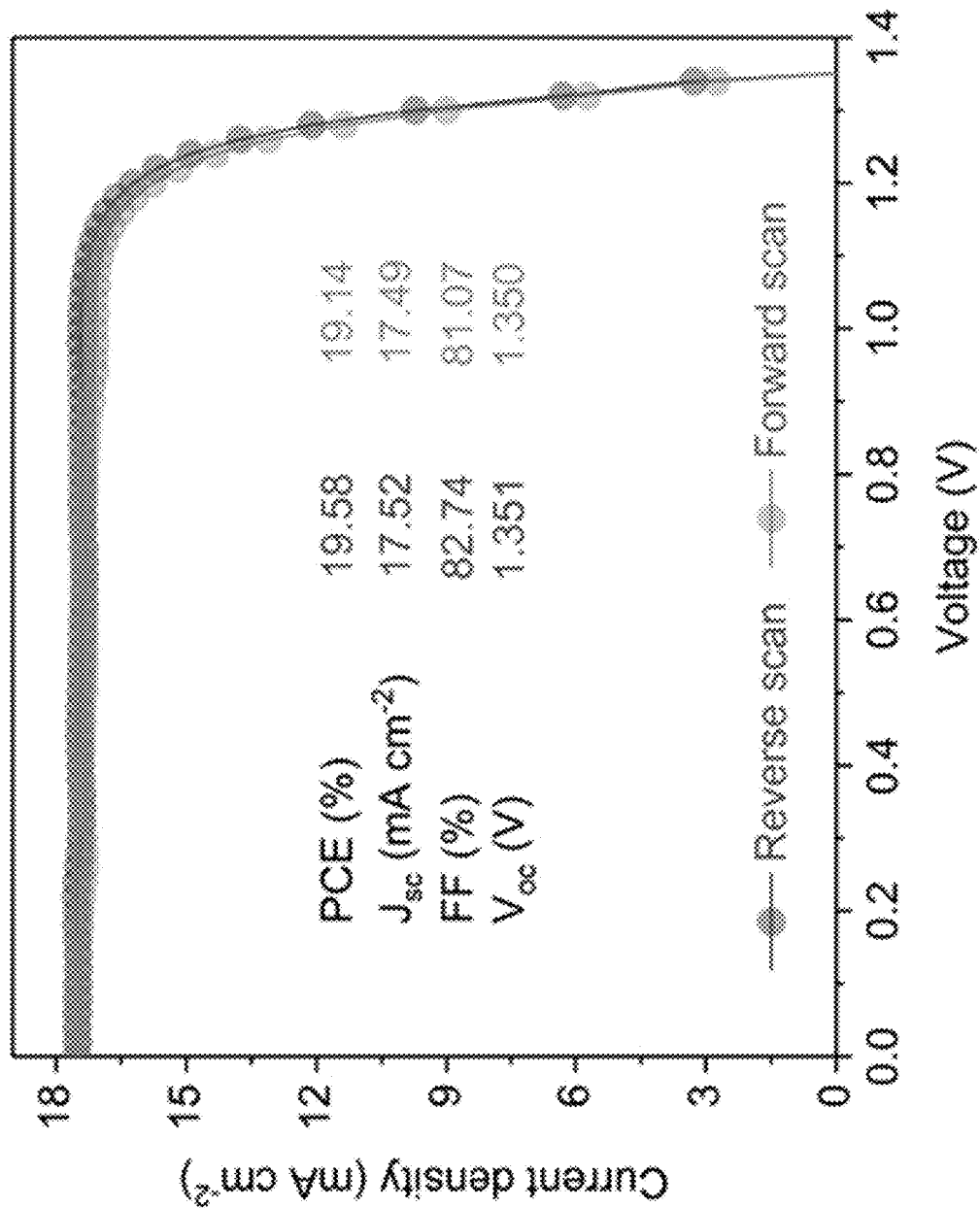
FIG. 38 shows J-V curves of the target PSCs with reverse and forward scans.
Figure 39A:
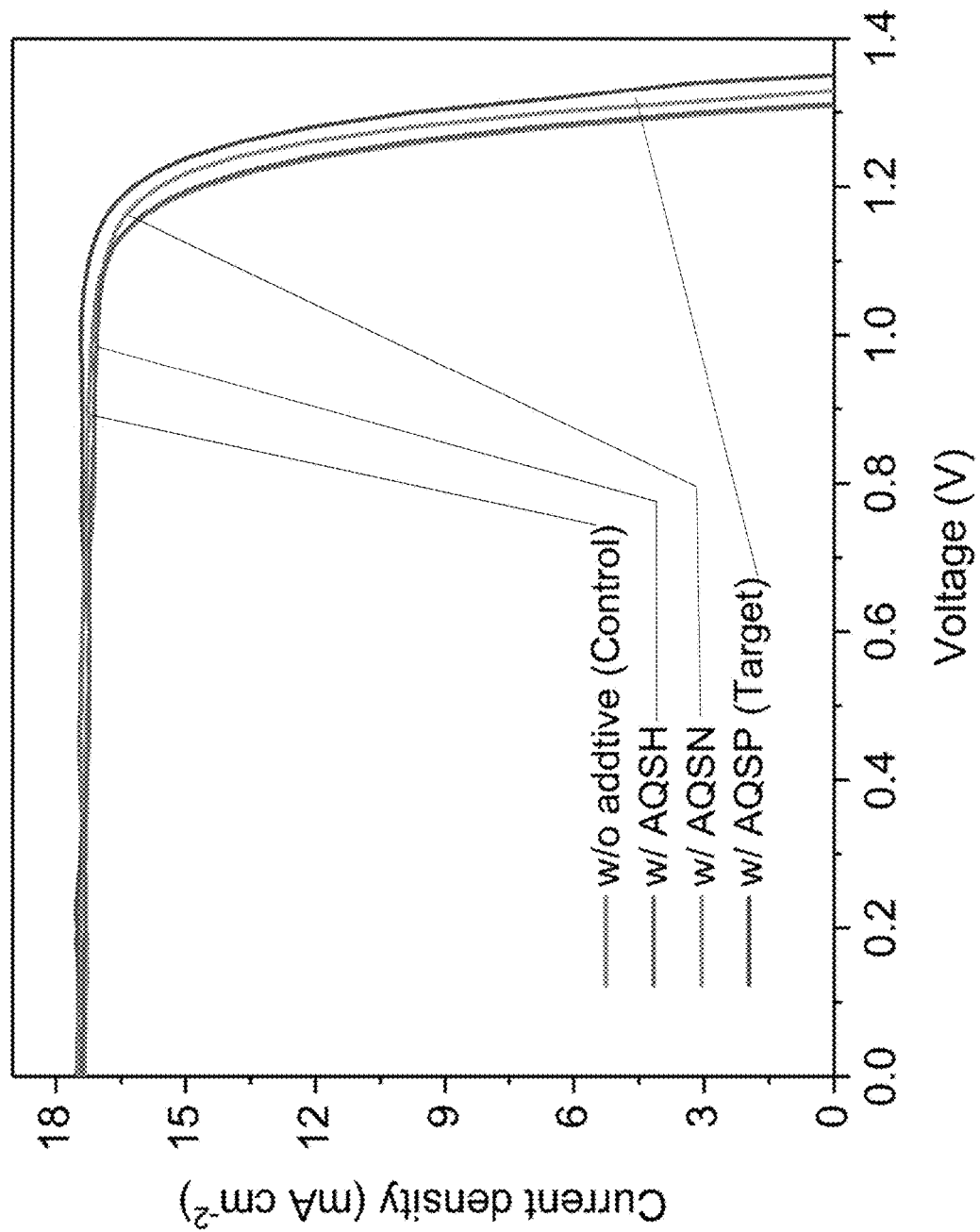
FIG. 39A shows the J-V curves of the single-junction PSCs based on the perovskites with different concentrations of AQSP.

To further investigate the suppressed phase segregation and non-radiative recombination properties imparted by AQSP additive, single-junction wide-E$_g$ PSCs were fabricated based on the structure of glass/ITO/DC-PA/perovskite/C60/bathocuproine (BCP)/Ag, where ITO is indium tin oxide, and DC-PA denotes a p-type self-assembled monolayer (SAM). The characteristics of the devices based on the perovskite without and with AQSP (denoted as control and target, respectively) are discussed as follows. The control device exhibited a decent PCE of 18.68%, while the optimized target device achieved an efficiency of 19.58%, mainly due to the enhanced $V_{oc}$ from 1.309 V to 1.351 V (FIGS. 37A to 37C). The target device also showed negligible hysteresis as the PCE of 19.14% could be obtained under forward scan direction (FIG. 38). The photovoltaic performance of the devices based on the perovskites with different AQS derivatives is provided in FIG. 39A and summarized in FIG. 39B.

Figure 40:
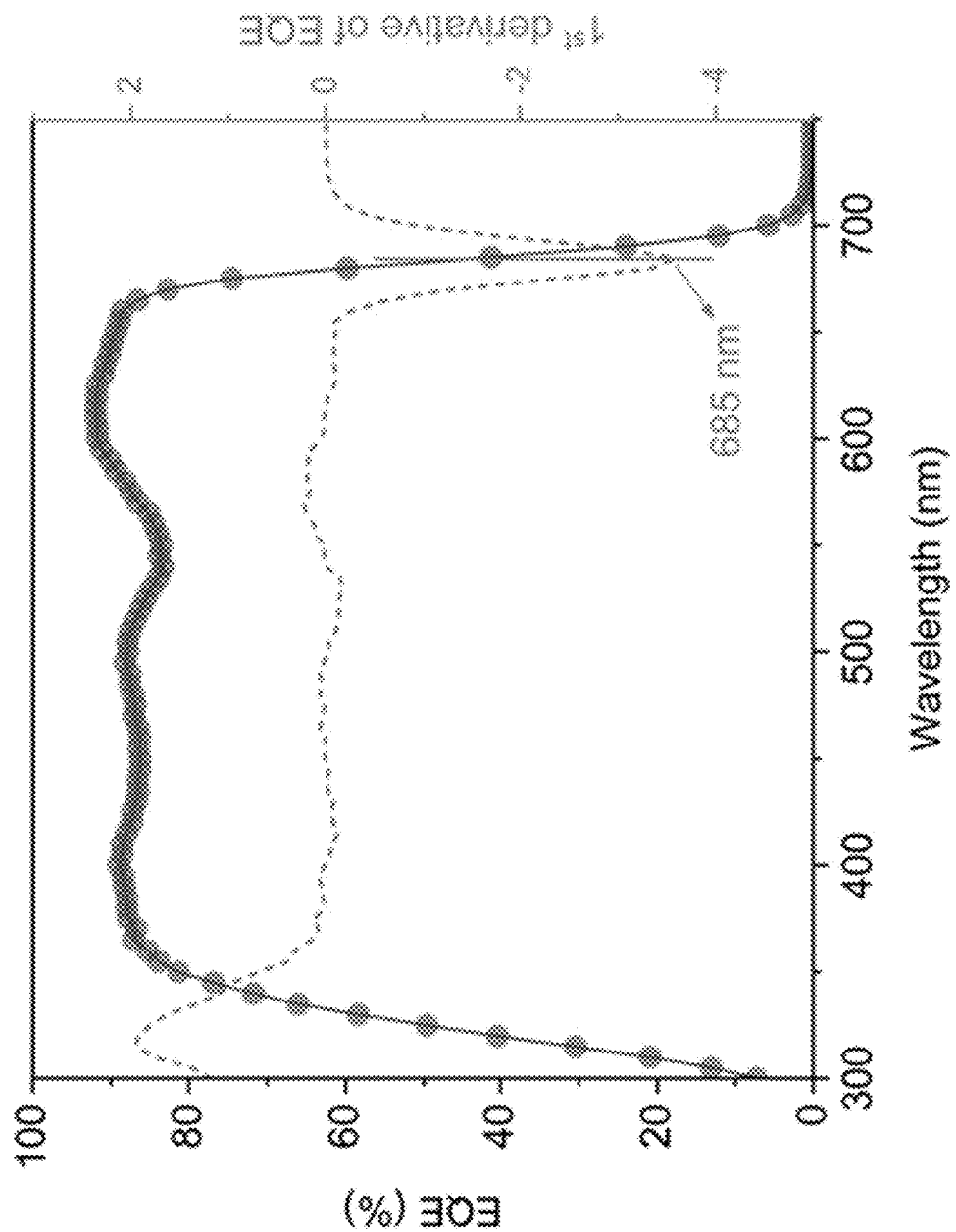
FIG. 40 shows the external quantum efficiency (EQE) curve with the determination of the bandgap for target PSC.
Figure 41:
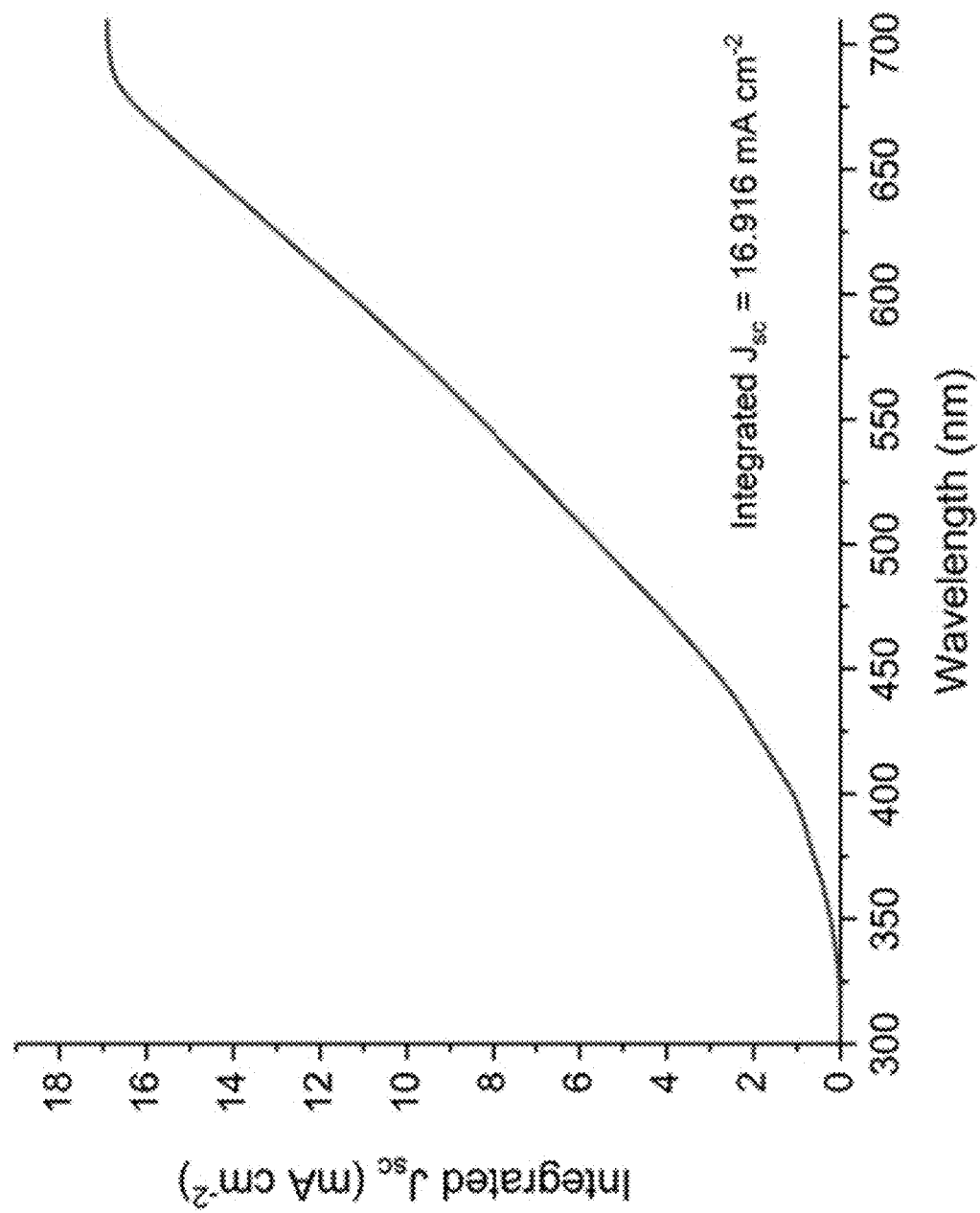
FIG. 41 shows the integrated $J_{sc}$ from the corresponding EQE spectrum of the champion target PSC.
Figure 42A:
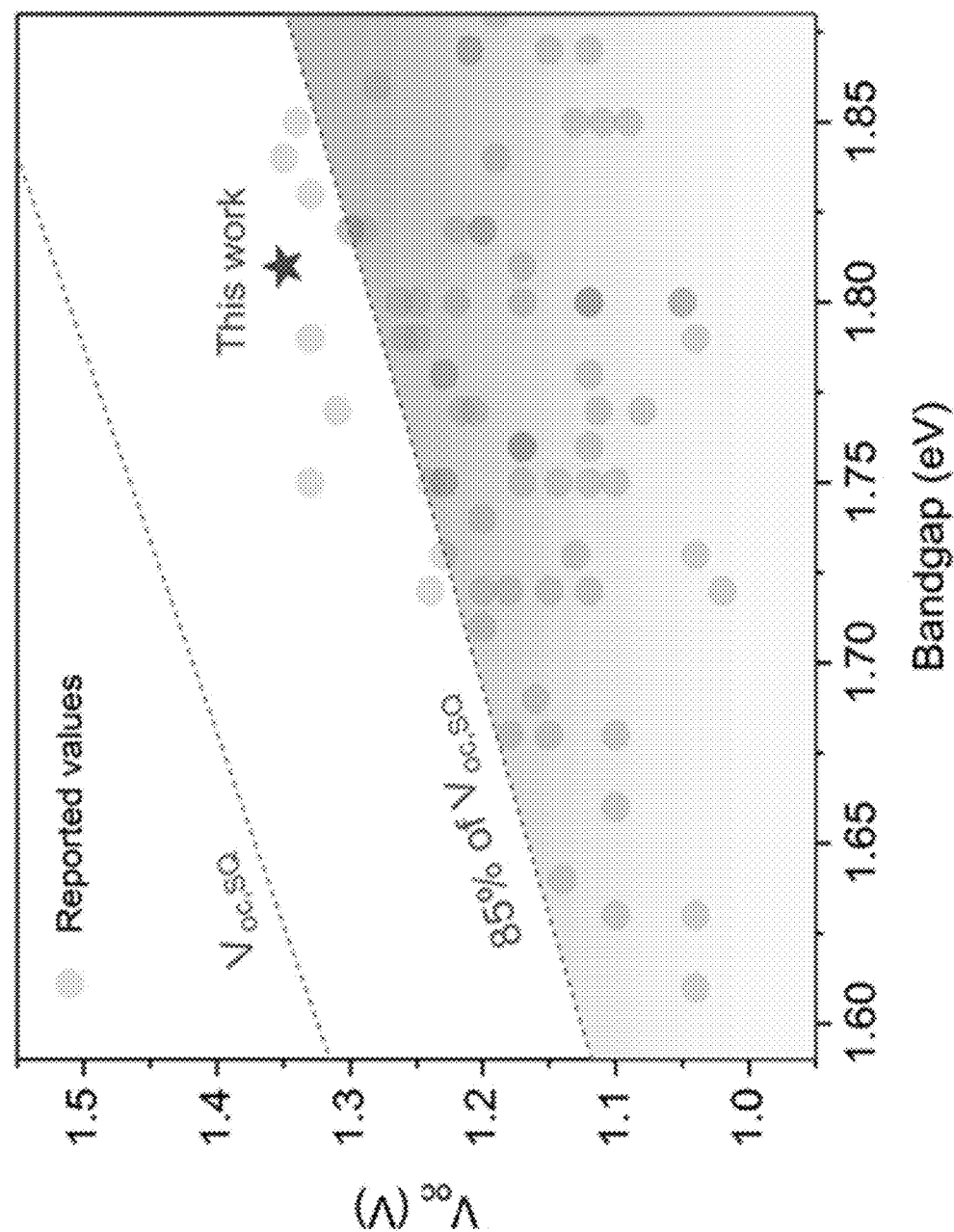
FIG. 42A shows the summary of the reported $V_{oc}$ values for the representative PSCs with the bandgap ranging from 1.60 to 1.85 eV.
Figure 43:
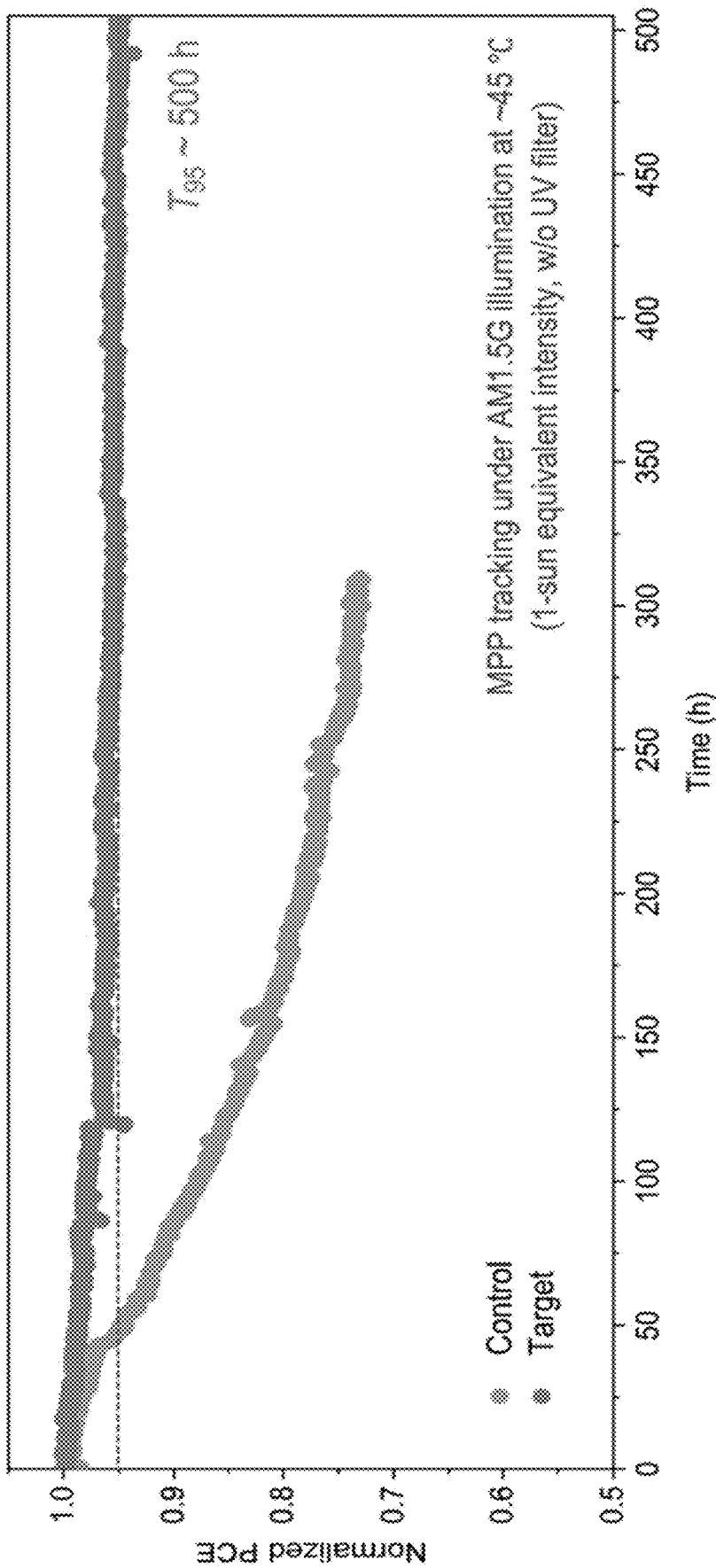
FIG. 43 shows the continuous maximum power point (MPP) tracking of the encapsulated PSCs under simulated AM1.5G illumination (100 mW cm$^{-2}$, without UV filter) in an $N_2$-filled chamber without temperature control. The initial efficiency of control and target PSC are 18.08% and 18.98%, respectively.

The bandgap of the target device was determined to be 1.81 eV by differentiating its external quantum efficiency (EQE) spectrum, which exhibited an inflection point at 685 nm (FIG. 40). The integrated short-circuit current density ($J_{sc}$) from the EQE matched well with the value extracted from the J-V curve (FIG. 41). The $V_{oc}$ deficit ($E_g$−q$V_{oc}$) of the target device was calculated to be 0.459 V, which is the lowest value reported so far for PSCs with an E$_g$ of ~1.80 eV (FIGS. 42A and 42B). Furthermore, we achieved significantly improved long-term stability for the target cell (initial efficiency=18.98%), which retained 95% of its initial PCE after operating under 1-sun illumination at its maximum power point (MPP) for 500 hours (FIG. 43). In contrast, the efficiency of the control cell (initial efficiency=18.08%) degraded rapidly (>20%) within 300 hours of operation.

Figure 44:
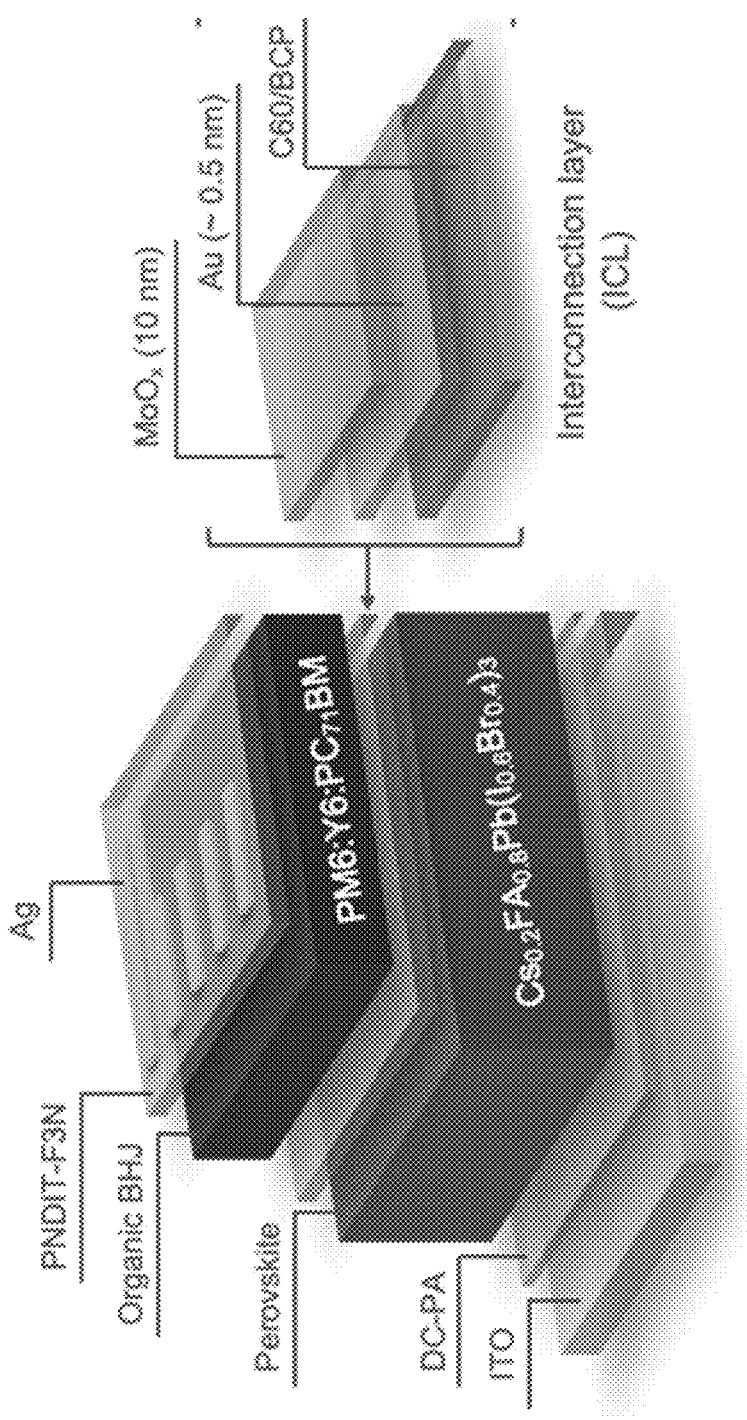
FIG. 44 is a schematic diagram illustrating the structure of a monolithic (two-terminal) PO-TSC with an interconnection layer (ICL) of BCP/Au/$MoO_3$.
Figure 45:
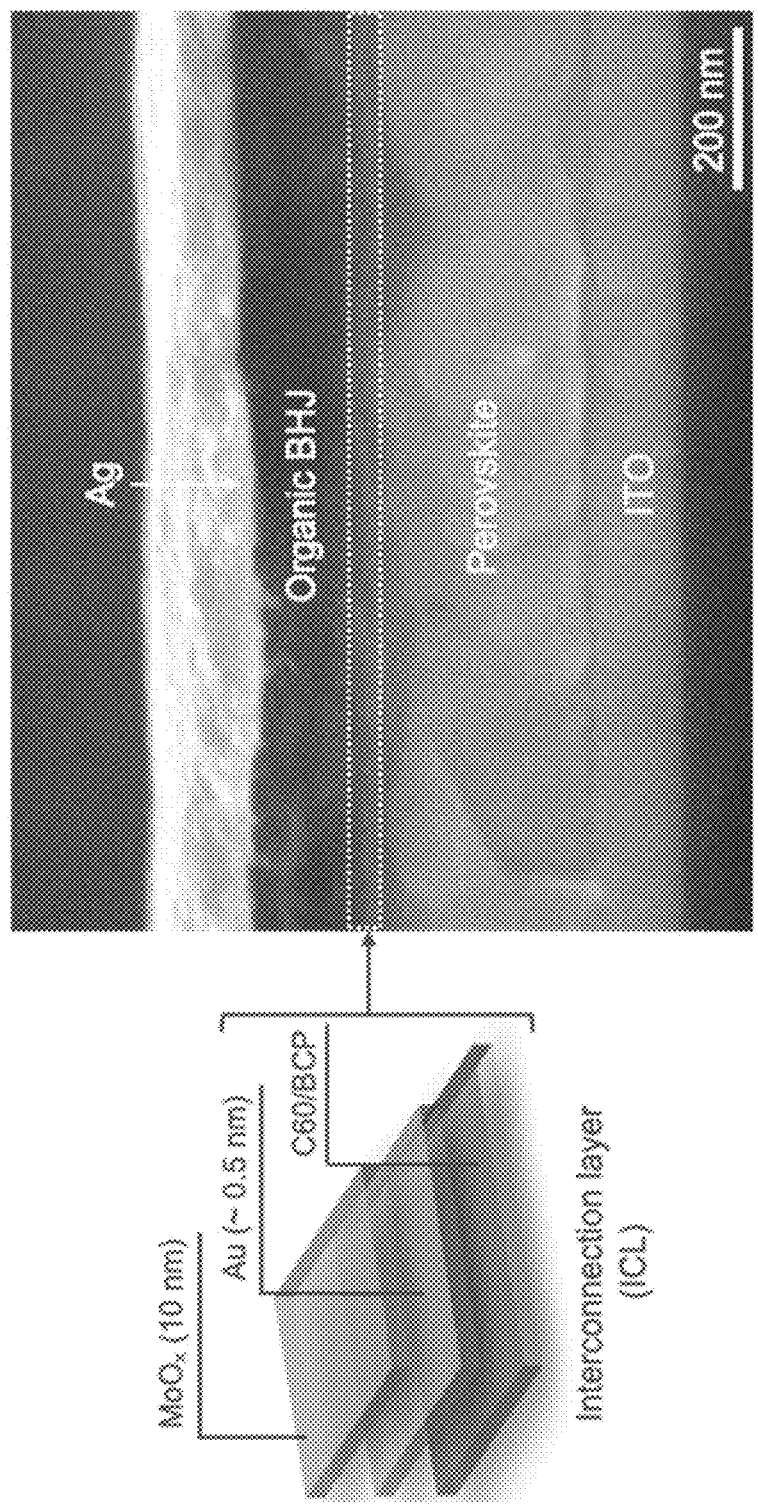
FIG. 45 shows the cross-section scanning electron microscopy (SEM) image corresponding to FIG. 44.

The above wide-E$_g$ perovskite was integrated with organic semiconductors for constructing monolithic PO-TSCs. The PM6:Y6:PC$_{71}$BM ternary blend was used as the bulk heterojunction layer in the narrow-E$_g$ rear subcell. The device structure of PO-TSC is depicted in FIG. 44, where BCP/Au/MoO$_x$ acts as the interconnecting layer (ICL). To obtain a good trade-off between transparency and electrical properties, a 0.5 nm-thick Au was utilized as the recombination layer. The thickness of the perovskite and organic BHJ layer was optimized to be ~260 nm and ~150 nm, respectively, to ensure efficient photon utilization and current matching between the two subcells (FIG. 45).

Figure 46A:
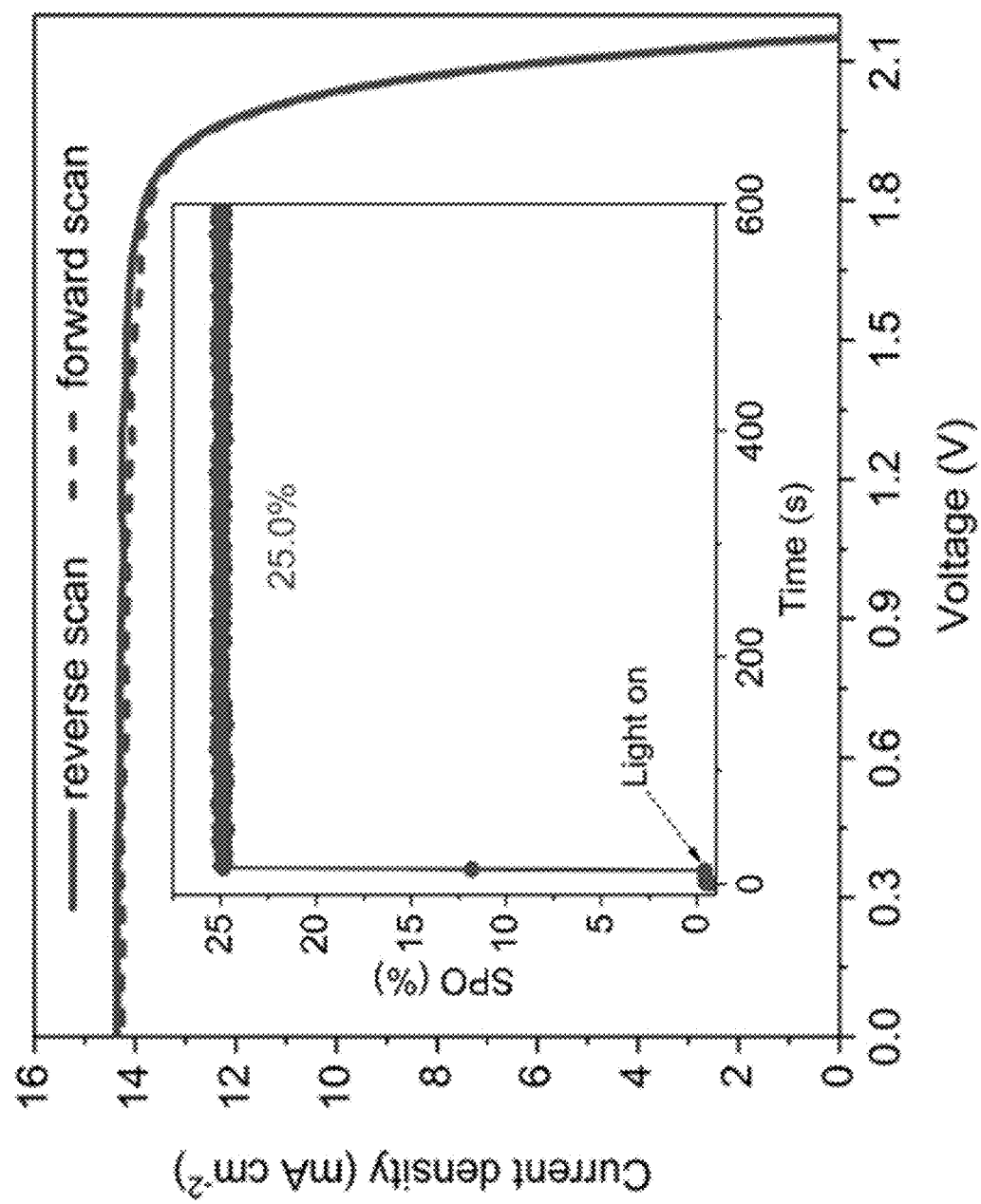
FIG. 46A shows the J-V curves of the PO-TSC under reverse and forward scans. The inset shows the stabilized power output (SPO) of the tandem cell.
Figure 47:
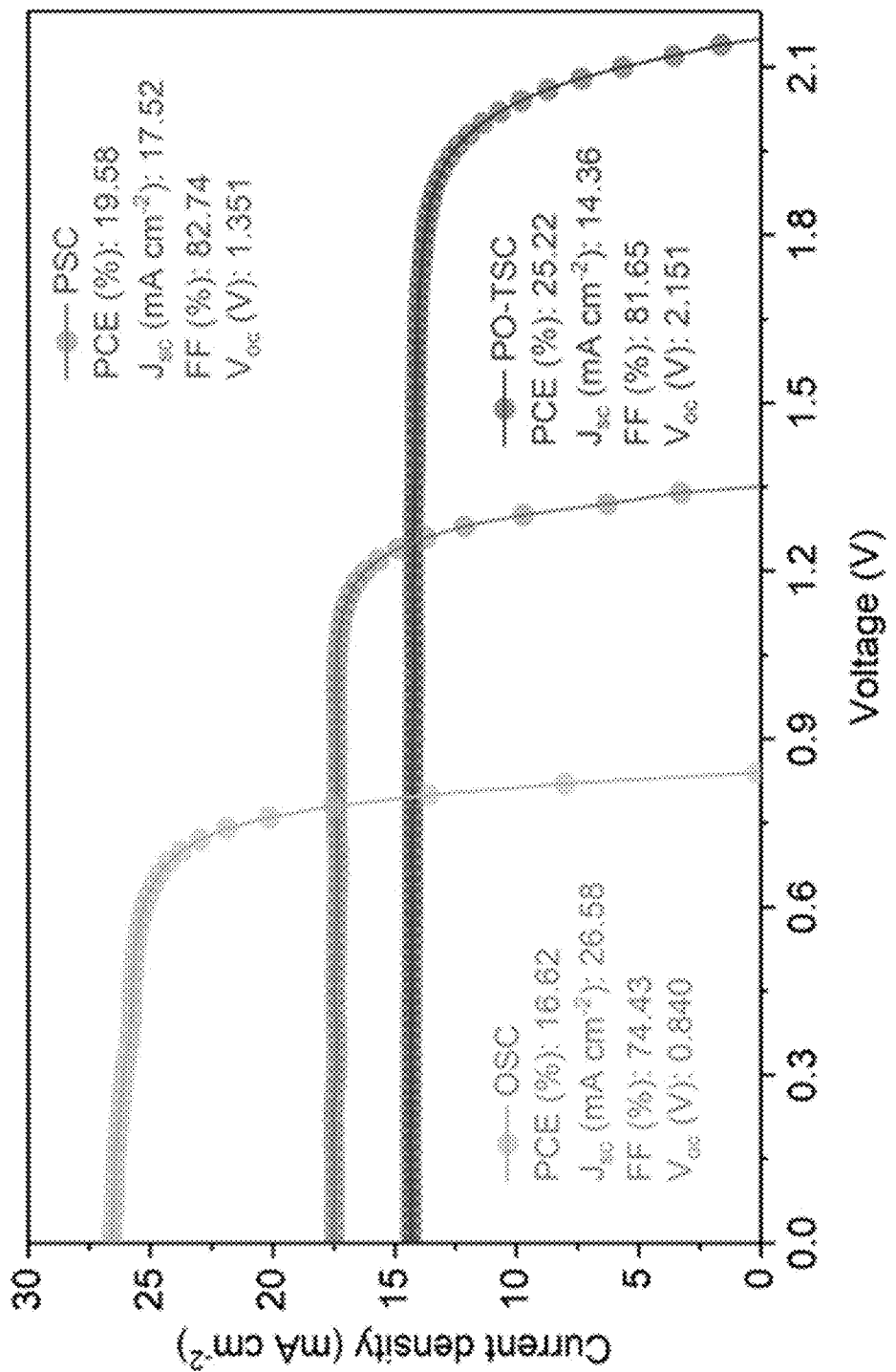
FIG. 47 shows the J-V curves of the PSC, OSC, and PO-TSC.
Figure 48:
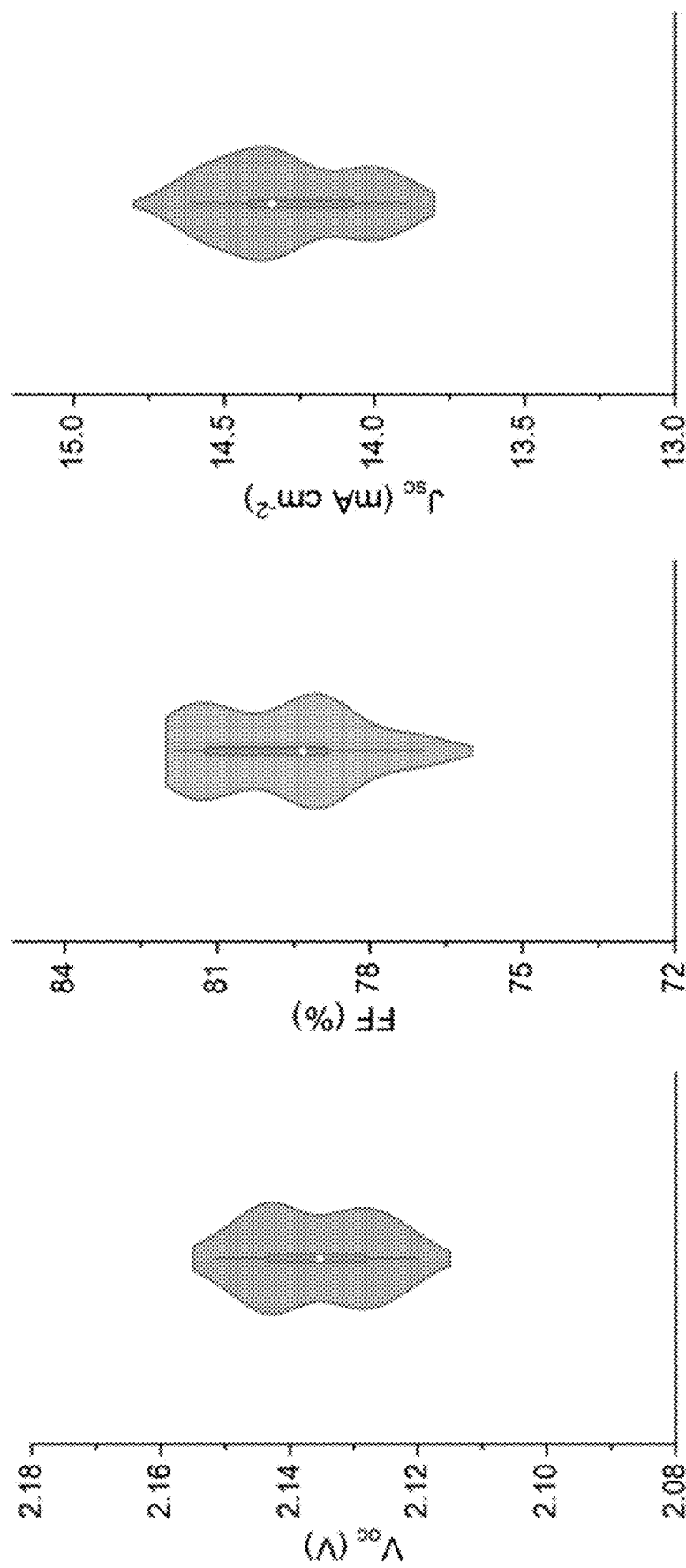
FIG. 48 shows the violin plots summarizing the photovoltaic parameters of PO-TSCs (25 devices fabricated from different batches)
Figure 49:
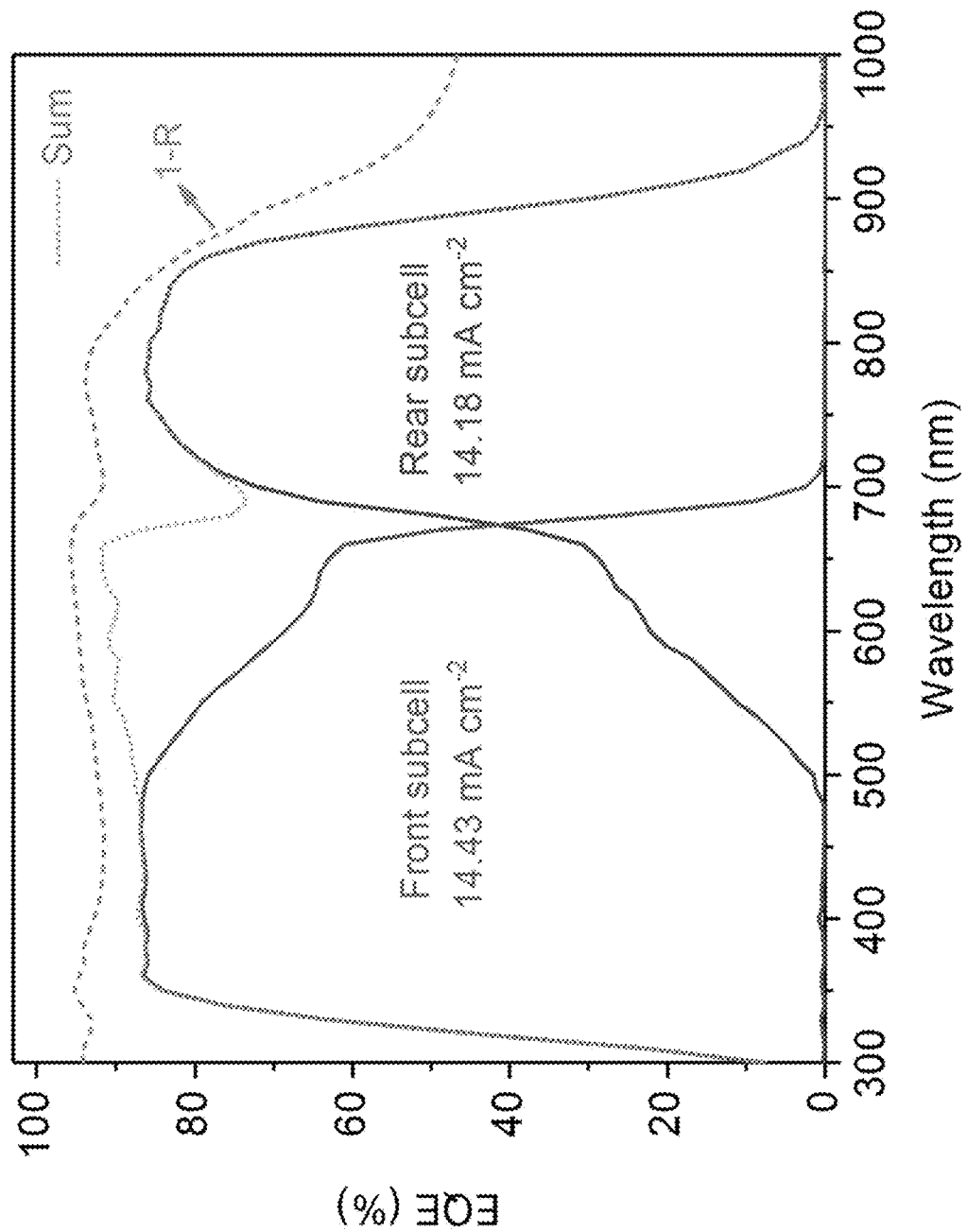
FIG. 49 shows the EQE spectra of the perovskite and organic subcell in the PO-TSC. The dotted line indicates the sum of EQE % of the front subcell and rear subcell at different wavelengths. The dash line 1-R indicates the sum of transmittance and parasitic absorption of the device, with R being to the reflection of the whole device (i.e., the PO-TSC), which is measured from the glass/ITO side in an integrated sphere.

Remarkably, the tandem solar cell achieved an impressive PCE of 25.22% with a high $V_{oc}$ of 2.151 V, $J_{sc}$ of 14.36 mA cm$^{-2}$, and fill factor (FF) of 81.65%, exhibiting negligible hysteresis and a stabilized power output (SPO) of 25.00%. (FIGS. 46A and 46B). Such high efficiency can be ascribed to the low voltage loss from the perovskite subcell and ICL (FIGS. 47 and 48). The tandem cell of this work also showed good current matching, where the $J_{sc}$ of 14.84 mA cm$^{-32}$ and 14.38 mA cm$^{-32}$ are integrated from the EQE spectrum of perovskite and organic subcells, respectively (FIG. 49).

Figure 50:
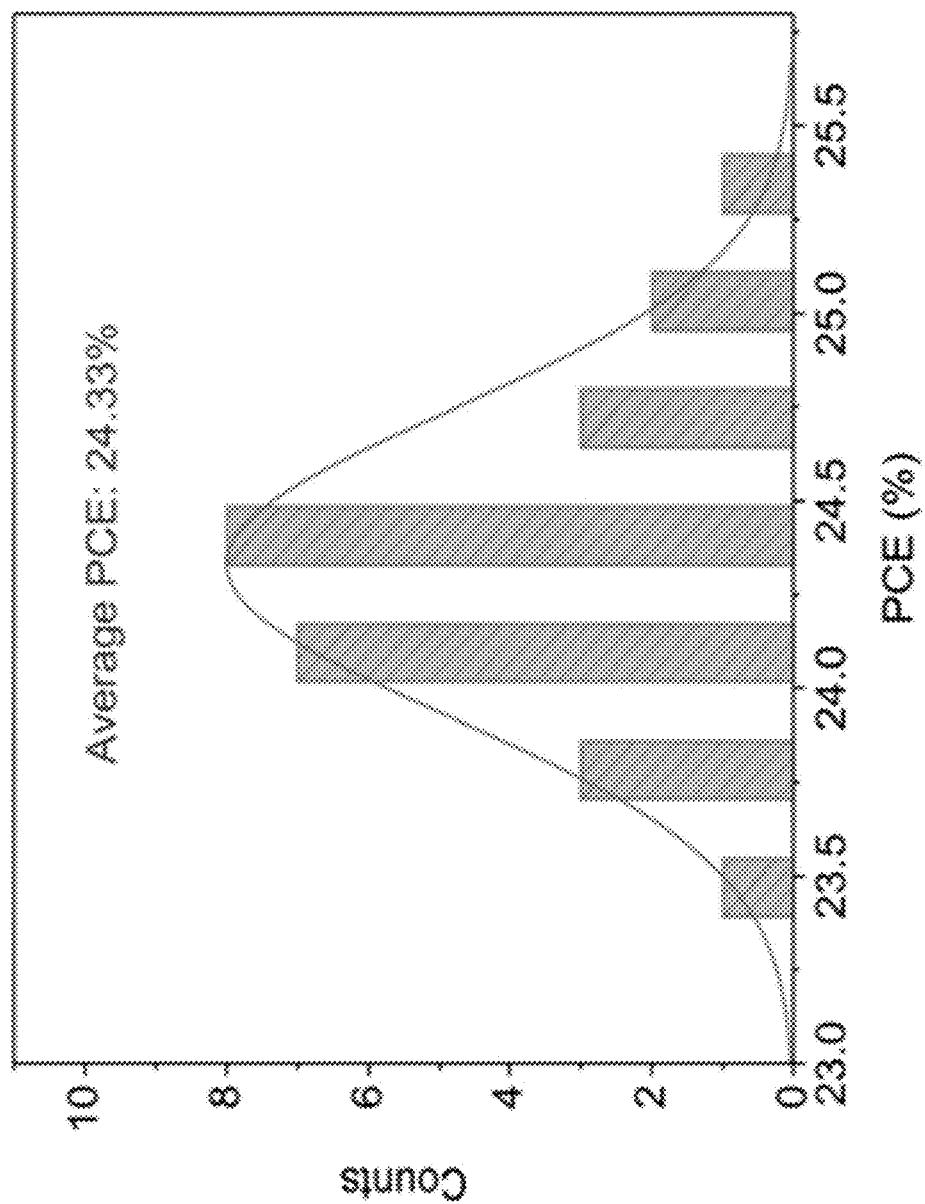
FIG. 50 shows the efficiency distribution of 25 individual tandem cells (from different batches)
Figure 51:
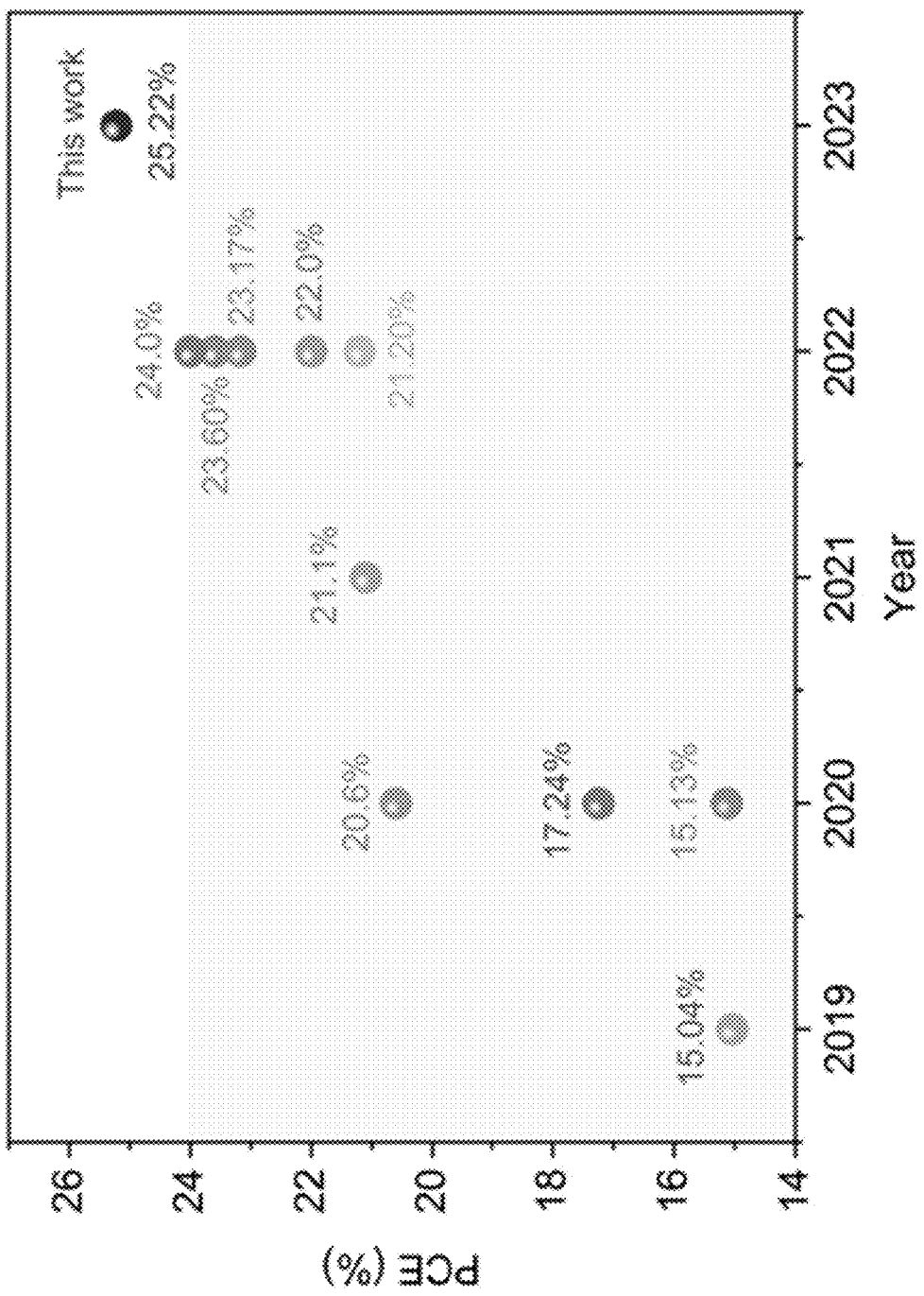
FIG. 51 shows the summary of the PCEs for the reported PO-TSCs.
Figure 52C:
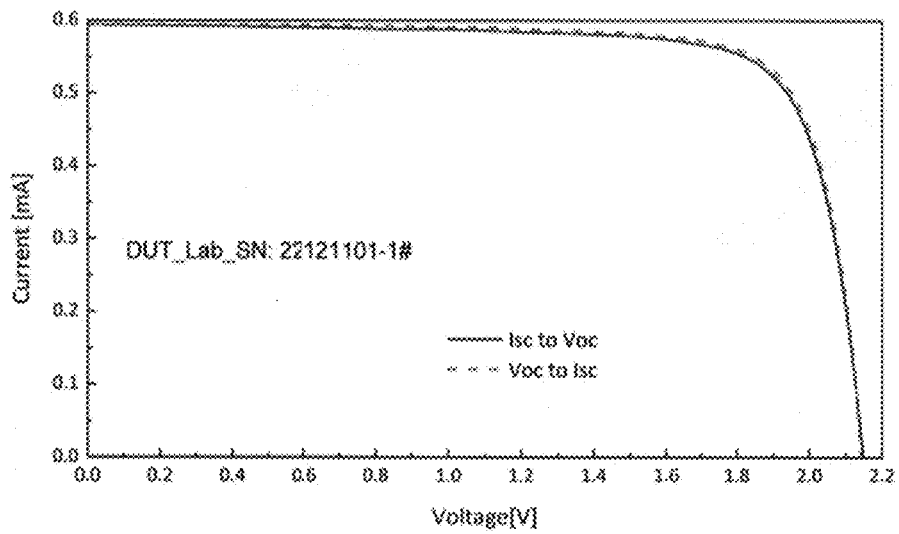
Figure 52D:
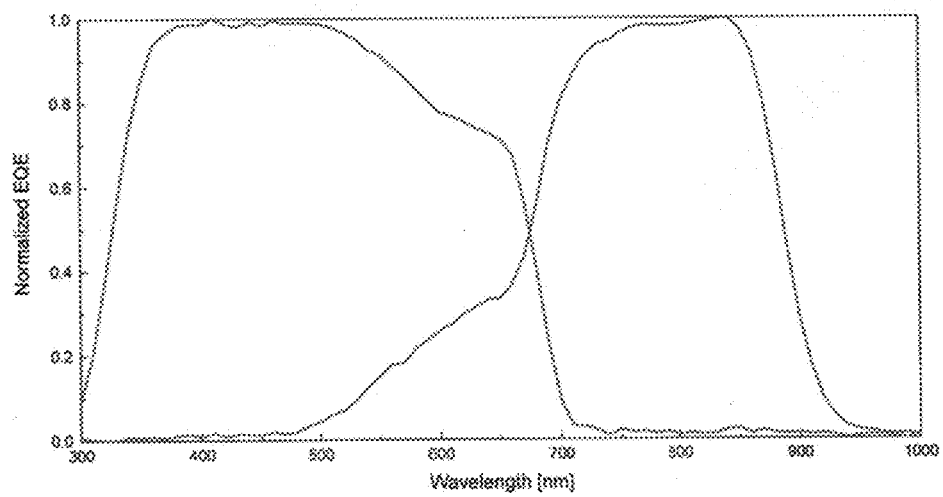
Figure 52E:
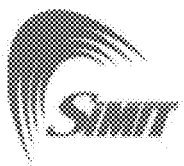
Figure 54:
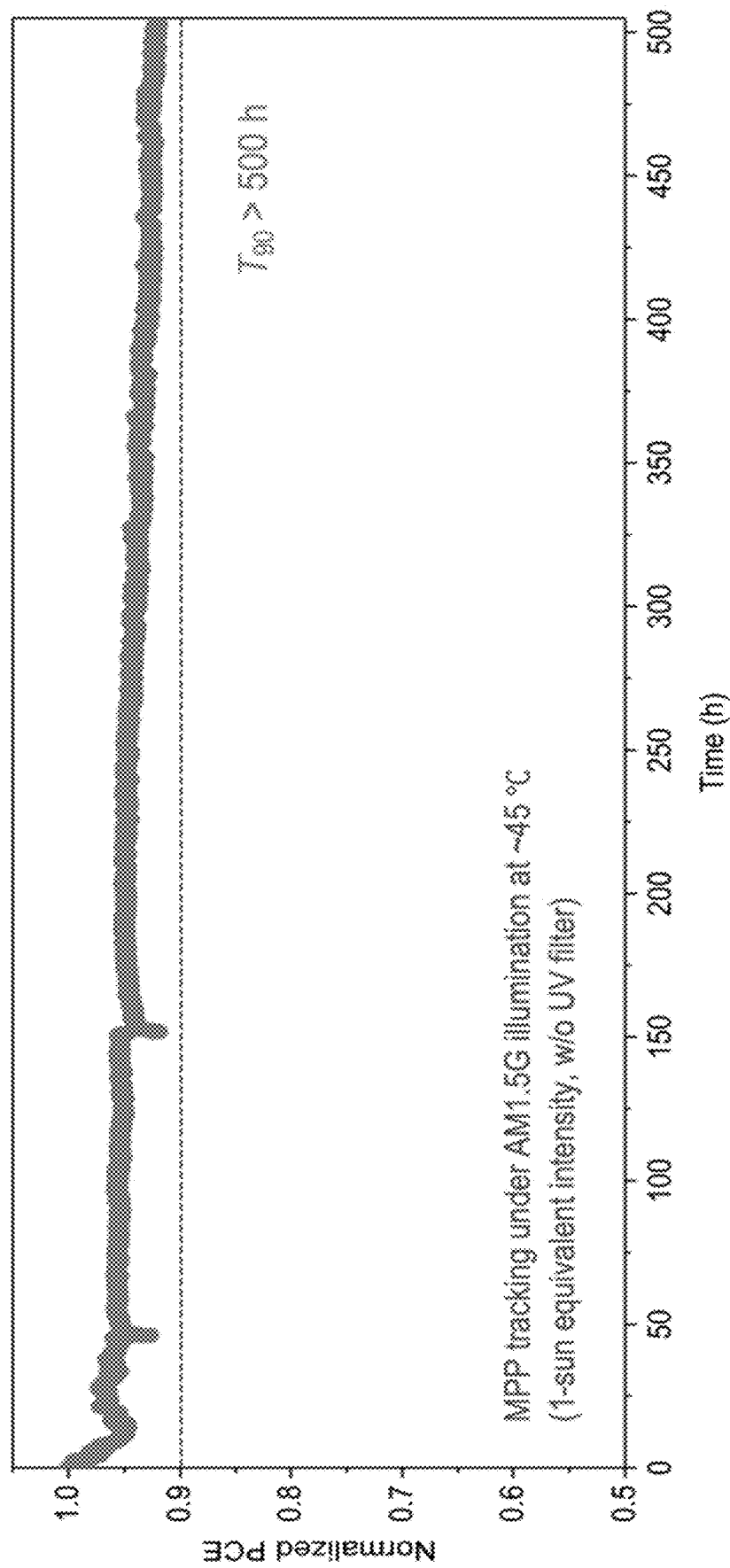
FIG. 54 shows the continuous MPP tracking of the encapsulated PO-TSC under simulated AM1.5G illumination (100 mW $cm^{-32}$, without UV filter) in an $N_2$-filled chamber without temperature control. The initial efficiency of the tandem cell is 24.67%.

The average PCE of 24.33% was calculated from 25 individual tandem cells that were fabricated from different batches, as shown in FIG. 50. An encapsulated tandem cell (with a fixed mask) was also sent to an independent photovoltaic calibration institute (SIMIT) for certification, realizing a certified efficiency of 24.27%. It is believed that this value represents the highest certified PCE among the reported PO-TSCs (FIGS. 51, 52A-52E, and 53). An encapsulated tandem cell was subjected to 1-sun illumination (AM 1.5G spectrum, without a UV filter) in an N$_2$-filled chamber, which retained 92% of its initial PCE after 500 hours of continuous operation at ~45° C. (FIG. 54).

The invention has been given by way of example only, and various other modifications of and/or alterations to the described embodiment may be made by persons skilled in the art without departing from the scope of the invention as specified in the appended claims.

The invention claimed is:

1. A perovskite layer for use in a solar cell comprising a mixture of a mixed-halide perovskite and a sulfonyl naphthoquinone-based compound with a structure of any one of Formula (II), (III), (IV), (V), (VI), or (VII):

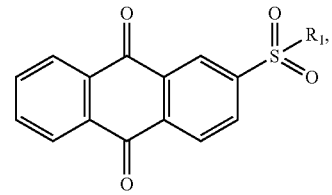
Formula (II)

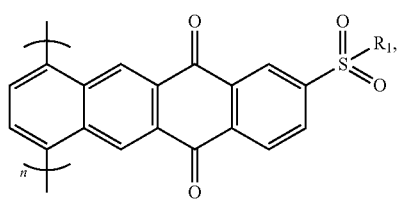
Formula (III)

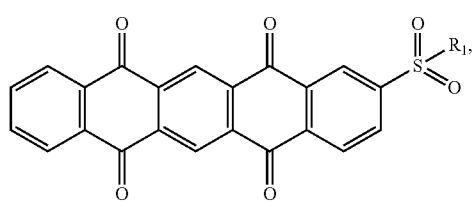
Formula (IV)

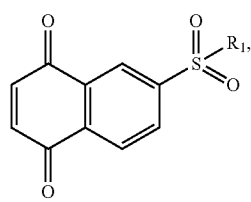
Formula (V)

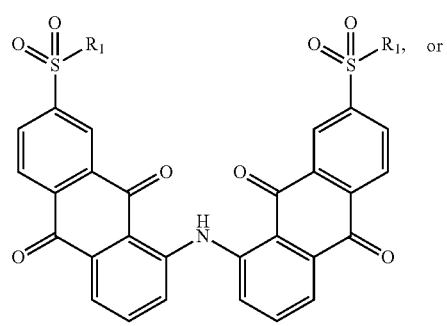
Formula (VI)

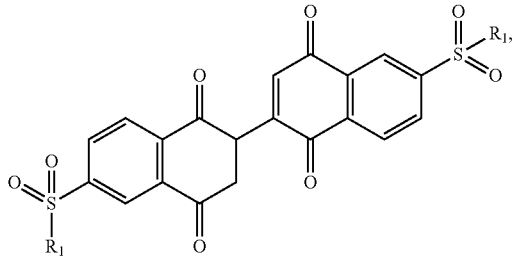
Formula (VII)

wherein:
R$_1$ is independently selected from one of OM, OR$_4$, and NR$_5$R$_6$, with M being a cation selected from the group consisting of H$^+$, Na$^+$, K$^+$, Cs$^+$, Rb$^+$, Sr$^{2+}$, Ca$^{2+}$, Ni$^{2+}$, Cu$^{2+}$, Co$^{2+}$, Zn$^{2+}$, Mg$^{2+}$, Ba$^{2+}$, Li$^+$, ammonium ion, and aminum ion;

R$_4$, R$_5$ and R$_6$ are independently selected from the group consisting of hydrogen, substituted or unsubstituted C1 to C4 alkyl, substituted or unsubstituted C2 to C6 alkenyl, substituted or unsubstituted C2 to C6 alkynyl, halogen, unsubstituted C6 to C10 aryl, —CN, —C(=O)OH, —C(=O)H, —C(=O)R$_7$, —OR$_7$, —SH, —SR$_7$, —NH$_2$, —NHR$_6$, —N(R$_7$)$_2$, —Si(R$_7$)$_3$, —OSi(R$_7$)$_3$, —S(O)OH and —P(O)(OH)$_2$ where R$_7$ is an alkyl or a phenyl, and n being 1-1000;

wherein the sulfonyl naphthoquinone-based compound does not include a porphyrin, and is arranged to suppress halide segregation in the mixed-halide perovskite.

2. The perovskite layer as claimed in claim 1, wherein the sulfonyl naphthoquinone-based compound of Formula (II) is selected from any one of Formula (VIII), Formula (IX), or Formula (X):

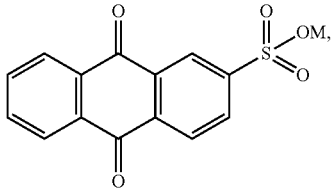
Formula (VIII)

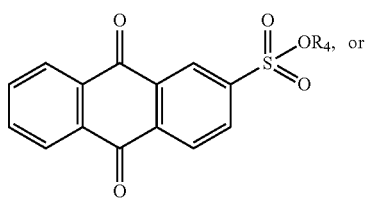
Formula (IX)

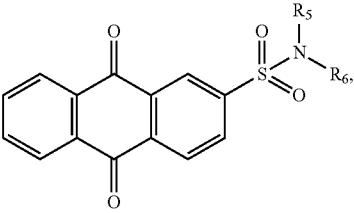
Formula (X)

with M being H$^+$, ammonium ion or aminum ion; R$_4$ being C1 to C4 alkyl; R$_5$ and R$_6$ being independently selected from hydrogen and C1 to C4 alkyl.

3. The perovskite layer as claimed in claim 2, wherein the sulfonyl naphthoquinone-based compound of Formula (VIII) is selected from any one of Formula (VIIIa), (VIIIb), and (VIIIc):

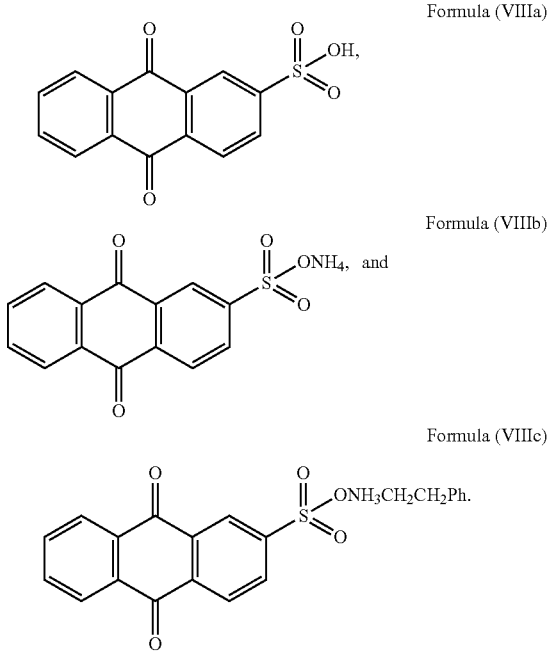

4. The perovskite layer as claimed in claim 2, wherein the sulfonyl naphthoquinone-based compound comprises a structure of Formula (IXa):

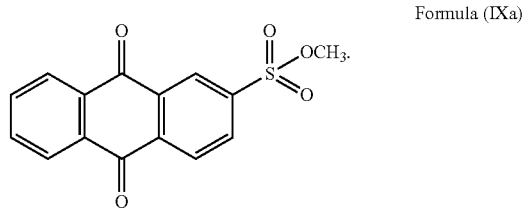 [SMILES: COS(=O)(=O)c1ccc2c(c1)C(=O)c1ccccc1C2=O]

5. The perovskite layer as claimed in claim 2, wherein the sulfonyl naphthoquinone-based compound comprises a structure of Formula (Xa):

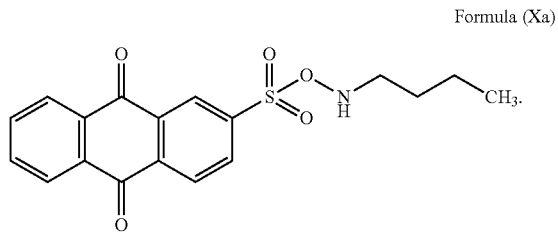 [SMILES: CCCCNOS(=O)(=O)c1ccc2c(c1)C(=O)c1ccccc1C2=O]

6. The perovskite layer as claimed in claim 1, wherein the mixed-halide perovskite comprises a crystal grain structure of $[A^{+1}B^{+2}X^{-1}_3]$, with $A^{+1}$ being an A-site monovalent cation, $B^{+2}$ being a B-site divalent cation, and $X^{-1}$ being a halide anion.

7. The perovskite layer as claimed in claim 6, wherein the A-site monovalent cation is selected from the group consisting of formamidinium ($FA^+$), methylammonium ($MA^+$), ethylammonium ($EA^+$), guanidinium ($GA^+$), $Cs^+$, $Rb^+$ and a combination thereof; the B-site divalent cation is selected from the group consisting of $Pb^{2+}$, $Sn^{2+}$, $Ge^{2+}$ and a combination thereof; and the halide anion is selected from the group consisting of $I^-$, $Br^-$, $Cl^-$ and a combination thereof.

8. The perovskite layer as claimed in claim 7, wherein the mixed-halide perovskite is selected from any one of $CsPb_{0.5}Sn_{0.5}I_3$, $FAPbI_3$, $MA_{0.25}FA_{0.75}PbI_{2.2}Br_{0.6}Cl_{0.2}$, $Cs_{0.02}FA_{0.96}MA_{0.02}PbI_{0.99}Cl_{0.01}$, $MAPb_{0.92}Sn_{0.08}I_3$, $(FA_{0.95}MA_{0.05})_{0.95}Cs_{0.05}Pb(I_{0.96}Br_{0.04})_3$, $Rb_{0.1}FA_{0.8}GA_{0.1}Pb_{0.6}Ge_{0.4}I_3$, and $(FA_{0.92}MA_{0.08})_{0.9}Cs_{0.1}Pb(I_{0.92}Br_{0.08})_3$, and $Cs_{0.2}FA_{0.8}Pb(I_{0.6}Br_{0.4})_3$.

9. The perovskite layer as claimed in claim 6, wherein the crystal grain structure of $[A^{+1}B^{+2}X^{-1}_3]$ includes grain boundaries at which the sulfonyl naphthoquinone-based compound accommodates.

10. The perovskite layer as claimed in claim 1 containing about 0.3 mol % to about 1 mol % of the sulfonyl naphthoquinone-based compound.

11. The perovskite layer as claimed in claim 1 further comprising about 3 mol % of $MAPbCl_3$ and 5 mol % of 4-guanidinobenzoic acid.

12. The perovskite layer as claimed in claim 1 having a thickness of about 260 nm.

13. A solar cell comprising:
    a first hole transport layer;
    a first electron transport layer; and
    a first active layer of the perovskite layer as claimed in claim 1 that is disposed between the first hole transport layer and the first electron transport layer.

14. The solar cell as claimed in claim 13, wherein the first active layer is in direct contact with the first hole transport layer and the first electron transport layer.

15. The solar cell as claimed in claim 14, wherein the first hole transport layer is disposed on a transparent conductive layer that is disposed on a transparent substrate and the first electron transport layer is disposed on a first blocking layer that is disposed on a first metal layer.

16. The solar cell as claimed in claim 15, wherein the first hole transport layer is in direct contact with a transparent conductive layer and the first electron transport layer is in direct contact with the first blocking layer.

17. The solar cell as claimed in claim 15, wherein the transparent substrate is selected from the group consisting of glass, polymethyl methacrylate (PMMA), polycarbonate (PC), general-purpose polystyrene (GPPS), polyethylene glycol terephthalate (PET), polyethylene naphthalate (PEN), polydimethylsiloxane (PDMS), styrene-ethylene-butylene-styrene (SEBS), ethylene terephthalateco-1,4-cylclohex-ylenedimethylene terephthalate (PETG), acrylonitrile butadiene styrene copolymers (ABS), polypropylene (PP), polyamide (PA), acrylonitrile-styrene copolymer (AS), and a combination thereof.

18. The solar cell as claimed in 15, wherein the transparent conductive layer is selected from the group consisting of Indium Tin Oxide (ITO), Aluminum Zinc Oxide (AZO), Fluorine Tin Oxide (FTO), graphene, poly(3,4-ethylenedioxythiophene):poly(styrene sulfonate) (PEDOT:PSS), Ag nanowire, Cu nanowire and a combination thereof.

19. The solar cell as claimed in claim 15, wherein first hole transport layer is selected from the group consisting of poly(triaryl amine) (PTAA), PEDOT:PSS, NiOx, 2,2',7,7'-

Tetrakis[N,N-di(4-methoxyphenyl)amino]-9,9'-spirobifluorene (Spiro-OMeTAD), DC-PA, $MoO_x$ and a combination thereof.

20. The solar cell as claimed in claim 15, wherein the first electron transport layer is selected from the group consisting of $PC_{61}BM$, $C_{60}$, $SnO_2$, PNDIT-F3N and a combination thereof.

21. The solar cell as claimed in claim 15, wherein the first blocking layer is selected from the group consisting of bathocuproine (BCP), bis-$C_{60}$, $SnO_x$, $Zr(acac)_2$, $MoO_x$ and a combination thereof.

22. The solar cell as claimed in claim 15, wherein the first metal layer is selected from the group consisting of Ag, Cu, Au, Al, W, Fe, Pt and a combination thereof.

23. The solar cell as claimed in claim 13 comprises a band gap of about 1.81 eV.

24. The solar cell as claimed in claim 13 comprises a power conversion efficiency of about 18.98% to about 19.58%.

25. The solar cell as claimed in claim 13 comprises a power conversion efficiency of 95% of its initial value upon AM1.5G illumination for 500 hours at about 45° C.

26. The solar cell as claimed in claim 15, further comprising a subcell disposed on and in direct contact with the first metal layer.

27. The solar cell as claimed in claim 26, further including an anti-reflection layer to which the transparent conductive layer and the transparent substrate are disposed on and in direct contact therewith.

28. The solar cell as claimed in claim 26, wherein the anti-reflection layer is selected from the group consisting of $MgF_2$, LiF, PDMS and a combination thereof.

29. The solar cell as claimed in claim 26, wherein the subcell comprises:
 a second hole transport layer;
 a second electron transport layer; and
 a second active layer that is disposed between the second hole transport layer and the second electron transport layer.

30. The solar cell as claimed in claim 29, wherein the second active layer is in direct contact with the second hole transport layer and the second electron transport layer.

31. The solar cell as claimed in claim 29, wherein the second active layer is selected from the group consisting of a perovskite photovoltaic material, a Si photovoltaic material, a CIGS photovoltaic material, a CdTe photovoltaic material, an organic photovoltaic material and a combination thereof.

32. The solar cell as claimed in claim 30, wherein the second hole transport layer is disposed on the first metal layer and the second electron transport layer is disposed on a second metal layer.

33. The solar cell as claimed in claim 29, wherein the second hole transport layer is in direct contact with the first metal layer and the second electron transport layer is in direct contact with the second metal layer.

34. The solar cell as claimed in claim 30, wherein the second hole transport layer is disposed on the first metal layer and the second electron transport layer is disposed on the second metal layer.

35. The solar cell as claimed in claim 29, wherein the second hole transport layer is in direct contact with the first metal layer and the second electron transport layer is in direct contact with the second blocking layer.

36. The solar cell as claimed in claim 32 comprises a perovskite-organic tandem solar cell.

37. The solar cell as claimed in claim 36, wherein the perovskite-organic tandem solar cell comprises the first active layer of $Cs_{0.2}FA_{0.8}Pb(I_{0.6}Br_{0.4})_3$ and the second active layer of PM6:Y6:$P_{71}$BM.

38. The solar cell as claimed in claim 36, wherein the perovskite-organic tandem solar cell has a power conversion efficiency of about 24.27% to about 25.22%.

39. The solar cell as claimed in claim 36, wherein the perovskite-organic tandem solar cell has a power conversion efficiency of 92% of its initial value upon AM1.5G illumination for 500 hours at about 45° C.

* * * * *